United States Patent
Lo et al.

(10) Patent No.: US 11,031,100 B2
(45) Date of Patent: *Jun. 8, 2021

(54) SIZE-BASED SEQUENCING ANALYSIS OF CELL-FREE TUMOR DNA FOR CLASSIFYING LEVEL OF CANCER

(71) Applicant: The Chinese University of Hong Kong, Shatin (HK)

(72) Inventors: Yuk Ming Dennis Lo, Hong Kong (CN); Wai Kwun Rossa Chiu, Hong Kong (CN); Kwan Chee Chan, Hong Kong (CN); Wenli Zheng, North Augusta, SC (US); Peiyong Jiang, Hong Kong (CN); Jiawei Liao, Hong Kong (CN)

(73) Assignee: The Chinese University of Hong Kong, Shatin (HK)

( * ) Notice: Subject to any disclaimer, the term of this patent is extended or adjusted under 35 U.S.C. 154(b) by 0 days.

This patent is subject to a terminal disclaimer.

(21) Appl. No.: 16/913,510

(22) Filed: Jun. 26, 2020

(65) Prior Publication Data

US 2020/0327960 A1 Oct. 15, 2020

Related U.S. Application Data

(60) Continuation of application No. 15/411,695, filed on Jan. 20, 2017, now Pat. No. 10,741,270, which is a division of application No. 13/789,553, filed on Mar. 7, 2013, now Pat. No. 9,892,230.

(60) Provisional application No. 61/621,451, filed on Apr. 6, 2012, provisional application No. 61/608,623, filed on Mar. 8, 2012.

(51) Int. Cl.
| | | |
|---|---|---|
| *G16B 30/00* | (2019.01) | |
| *C12Q 1/6869* | (2018.01) | |
| *G16H 50/30* | (2018.01) | |
| *G16H 50/20* | (2018.01) | |
| *G16H 10/40* | (2018.01) | |
| *G16B 20/00* | (2019.01) | |
| *C12Q 1/6809* | (2018.01) | |
| *C12Q 1/6827* | (2018.01) | |
| *C12Q 1/6816* | (2018.01) | |

(52) U.S. Cl.
CPC .......... *G16B 30/00* (2019.02); *C12Q 1/6809* (2013.01); *C12Q 1/6816* (2013.01); *C12Q 1/6827* (2013.01); *C12Q 1/6869* (2013.01); *G16B 20/00* (2019.02); *G16H 10/40* (2018.01); *G16H 50/20* (2018.01); *G16H 50/30* (2018.01)

(58) Field of Classification Search
None
See application file for complete search history.

(56) References Cited

U.S. PATENT DOCUMENTS

| | | |
|---|---|---|
| RE44,596 E | 11/2013 | Stroun et al. |
| 8,620,593 B2 | 12/2013 | Lo et al. |
| 8,712,697 B2 | 4/2014 | Struble et al. |
| 8,741,811 B2 | 6/2014 | Lo et al. |
| 9,121,069 B2 | 9/2015 | Lo et al. |
| 9,260,745 B2 | 2/2016 | Rava et al. |
| 9,361,426 B2 | 6/2016 | Akmaev et al. |
| 9,598,731 B2 | 3/2017 | Talasaz |
| 9,732,390 B2 | 8/2017 | Lo et al. |
| 9,758,814 B2 | 9/2017 | Fehr et al. |
| 9,834,822 B2 | 12/2017 | Talasaz |
| 9,840,743 B2 | 12/2017 | Talasaz |
| 9,892,230 B2 | 2/2018 | Lo et al. |
| 9,902,992 B2 | 2/2018 | Talasaz et al. |
| 9,982,300 B2 | 5/2018 | Lo et al. |
| 10,297,342 B2 | 5/2019 | Lo et al. |
| 10,364,467 B2 | 7/2019 | Lo et al. |
| 10,741,270 B2 | 8/2020 | Lo et al. |
| 2003/0180765 A1 | 9/2003 | Traverso et al. |
| 2005/0130176 A1 | 6/2005 | Vogelstein et al. |
| 2005/0164241 A1 | 7/2005 | Hahn et al. |
| 2005/0282213 A1 | 12/2005 | Halle |
| 2007/0122823 A1 | 5/2007 | Bianchi et al. |
| 2007/0122835 A1 | 5/2007 | Dhallan |
| 2007/0202525 A1 | 8/2007 | Quake et al. |
| 2011/0105353 A1 | 5/2011 | Lo et al. |
| 2011/0171741 A1 | 7/2011 | Wang et al. |

(Continued)

FOREIGN PATENT DOCUMENTS

| | | |
|---|---|---|
| CN | 1452665 | 10/2003 |
| CN | 1469932 | 1/2004 |

(Continued)

OTHER PUBLICATIONS

U.S. Appl. No. 13/789,553, Non-Final Office Action dated Feb. 12, 2016, 18 pages.

(Continued)

*Primary Examiner* — G Steven Vanni

(74) *Attorney, Agent, or Firm* — Kilpatrick Townsend & Stockton LLP

(57) ABSTRACT

A classification of a level of cancer in an organism is determined by analyzing a biological sample of the organism. The biological sample comprises clinically-relevant DNA and other DNA. At least some of the DNA is cell-free in the biological sample. An amount of a first set of DNA fragments from the biological sample corresponding to each of a plurality of sizes is measured. A first value of a first parameter is calculated based on the amounts of DNA fragments at the plurality of sizes. The first value is compared to a reference value. A classification of a level of cancer in the organism is determined based on the comparison.

22 Claims, 23 Drawing Sheets

(56) References Cited

U.S. PATENT DOCUMENTS

| | | |
|---|---|---|
| 2011/0230358 A1 | 9/2011 | Rava |
| 2011/0245085 A1 | 10/2011 | Rava et al. |
| 2011/0246083 A1 | 10/2011 | Fan et al. |
| 2013/0029852 A1 | 1/2013 | Rava et al. |
| 2013/0040824 A1 | 2/2013 | Lo et al. |
| 2013/0237431 A1 | 9/2013 | Lo et al. |
| 2013/0261984 A1 | 10/2013 | Eberle et al. |
| 2013/0288244 A1 | 10/2013 | Deciu et al. |
| 2014/0045181 A1 | 2/2014 | Lo et al. |
| 2014/0080715 A1 | 3/2014 | Lo et al. |
| 2014/0100121 A1 | 4/2014 | Lo et al. |
| 2014/0227699 A1 | 8/2014 | Lo et al. |
| 2014/0274740 A1 | 9/2014 | Srinivasan et al. |
| 2014/0274752 A1 | 9/2014 | Blume et al. |
| 2014/0364439 A1 | 12/2014 | Wu et al. |
| 2015/0104793 A1 | 4/2015 | Quake et al. |
| 2015/0197785 A1 | 7/2015 | Carter et al. |
| 2015/0211070 A1 | 7/2015 | Seligson et al. |
| 2015/0344970 A1 | 12/2015 | Vogelstein et al. |
| 2015/0376700 A1 | 12/2015 | Schnall-Levin et al. |
| 2016/0002739 A1 | 1/2016 | Schutz et al. |
| 2016/0017419 A1 | 1/2016 | Chiu et al. |
| 2016/0019338 A1 | 1/2016 | Chudova et al. |
| 2016/0032396 A1 | 2/2016 | Diehn et al. |
| 2016/0046979 A1 | 2/2016 | Leamon et al. |
| 2016/0232290 A1 | 8/2016 | Rava et al. |
| 2016/0239604 A1 | 8/2016 | Chudova et al. |
| 2016/0275239 A1 | 9/2016 | Devogelaere et al. |
| 2016/0281154 A1 | 9/2016 | So et al. |
| 2016/0304936 A1 | 10/2016 | Ji et al. |
| 2016/0333416 A1 | 11/2016 | Babiarz et al. |
| 2016/0333417 A1 | 11/2016 | Talasaz |
| 2017/0016054 A1 | 1/2017 | Southern et al. |
| 2017/0073774 A1 | 3/2017 | Lo et al. |
| 2017/0107576 A1 | 4/2017 | Babiarz et al. |
| 2017/0145516 A1 | 5/2017 | Kopetz et al. |
| 2017/0211143 A1 | 7/2017 | Shendure et al. |
| 2017/0211153 A1 | 7/2017 | Kohli et al. |
| 2017/0218459 A1 | 8/2017 | Talasaz et al. |
| 2017/0240973 A1 | 8/2017 | Eltoukhy et al. |
| 2017/0249421 A1 | 8/2017 | Eberle et al. |
| 2017/0260590 A1 | 9/2017 | Eltoukhy et al. |
| 2017/0326238 A1 | 11/2017 | Chang et al. |
| 2017/0342477 A1 | 11/2017 | Jensen et al. |
| 2017/0342500 A1 | 11/2017 | Marquard et al. |
| 2017/0362638 A1 | 12/2017 | Chudova et al. |
| 2018/0045727 A1 | 2/2018 | Spetzler et al. |

FOREIGN PATENT DOCUMENTS

| | | |
|---|---|---|
| CN | 1498276 | 5/2004 |
| CN | 1779688 | 5/2006 |
| CN | 1798974 | 7/2006 |
| CN | 1997757 | 7/2007 |
| CN | 101137760 | 3/2008 |
| CN | 101855363 | 10/2010 |
| CN | 102369299 | 3/2012 |
| CN | 103403182 | 11/2013 |
| EP | 1229135 | 8/2002 |
| EP | 1524321 | 4/2005 |
| EP | 2426217 | 3/2012 |
| EP | 2771483 | 9/2014 |
| EP | 3018213 | 5/2016 |
| EP | 3191628 | 7/2017 |
| EP | 3194612 | 7/2017 |
| EP | 3218523 | 9/2017 |
| JP | 2002272497 | 9/2002 |
| JP | 2007515947 | 6/2007 |
| JP | 2017063794 | 4/2017 |
| KR | 1020020064298 | 8/2002 |
| KR | 20040102024 | 12/2004 |
| RU | 2249820 | 4/2005 |
| WO | 3030823 | 4/2003 |
| WO | 3074723 | 9/2003 |
| WO | 2004016758 | 2/2004 |
| WO | 2004046370 | 6/2004 |
| WO | 2004078999 | 9/2004 |
| WO | 2004079011 | 9/2004 |
| WO | 2005035725 | 4/2005 |
| WO | 2005039389 | 5/2005 |
| WO | 2007028155 | 3/2007 |
| WO | 2007028155 | 6/2007 |
| WO | 2007100911 | 9/2007 |
| WO | 2008150368 | 12/2008 |
| WO | 2009013492 | 1/2009 |
| WO | 2009019455 | 2/2009 |
| WO | 2009037690 | 3/2009 |
| WO | 2009051842 | 4/2009 |
| WO | 2010112316 | 10/2010 |
| WO | 2011053790 | 5/2011 |
| WO | 2011054936 | 5/2011 |
| WO | 2011090556 | 7/2011 |
| WO | 2011103236 | 8/2011 |
| WO | 2012071621 | 6/2012 |
| WO | 2013052907 | 4/2013 |
| WO | 2013060762 | 5/2013 |
| WO | 2014039556 | 3/2014 |
| WO | 2014043763 | 3/2014 |
| WO | 2016015058 | 1/2016 |
| WO | 2016028316 | 2/2016 |
| WO | 2016040901 | 3/2016 |
| WO | 2016077709 | 5/2016 |
| WO | 2016116033 | 7/2016 |
| WO | 2016179049 | 11/2016 |
| WO | 2016179530 | 11/2016 |
| WO | 2016183106 | 11/2016 |
| WO | 2017009372 | 1/2017 |
| WO | 2017027391 | 2/2017 |
| WO | 2017062867 | 4/2017 |
| WO | 2017070497 | 4/2017 |
| WO | 2018081130 | 5/2018 |

OTHER PUBLICATIONS

U.S. Appl. No. 13/789,553, Non-Final Office Action dated Mar. 3, 2016, 19 pages.
U.S. Appl. No. 13/937,162, Non-Final Office Action dated Feb. 25, 2014, 11 pages.
U.S. Appl. No. 14/089,720, Final Office Action dated Jan. 26, 2017, 17 pages.
Australian Application No. 2008278839, First Examiner Report dated May 10, 2012, 3 pages.
Australian Application No. 2010317019, First Examination Report dated May 7, 2014, 3 pages.
Australian Application No. 2013200581, Second Examination Report dated Dec. 13, 2013, 5 pages.
Australian Application No. 2013202132, First Examination Report dated Jun. 5, 2014, 4 pages.
Australian Application No. 2013202141, First Examination Report dated Jun. 5, 2014, 12 pages.
Australian Application No. 2013202157, First Examination Report dated Jun. 5, 2014, 12 pages.
Australian Application No. 2013202160, First Examination Report dated Jun. 5, 2014, 13 pages.
Australian Application No. 2015200462, First Examination Report dated Aug. 10, 2016, 2 pages.
Australian Application No. 2015271883, First Examination Report dated Dec. 14, 2016, 4 pages.
Chen et al., Total Serum DNA and DNA Integrity: Diagnostic Value in Patients with Hepatitis B Virus-Related Hepatocellular Carcinoma, Pathology, vol. 44, No. 4, Jun. 2012, pp. 318-324.
Fan et al., Analysis of the Size Distribuiions of Fetal and Maternal Cell-Free ONA by Paired-End Sequencing, Clinical Chemistry, vol. 58, No. 8, Aug. 1, 2010, pp. 1279-1286.
Chinese Application No. 200880108126.3, Office Action dated May 28, 2013, 8 pages.
Chinese Application No. 201080059269.7, Office Action dated Aug. 26, 2014, 10 pages.
Chinese Application No. 201080059269.7, Office Action dated Jun. 25, 2013, 10 pages.

(56) References Cited

OTHER PUBLICATIONS

Chinese Application No. 201080059269.7, Office Action dated Jan. 22, 2014, 9 pages.
Dabney et al., Length and GC-Biases During Sequencing Library Amplification: A Comparison of Various Polymerase-Buffer Systems with Ancient and Modern DNA Sequencing Libraries, Bio Techniques, vol. 52, No. 2, Feb. 2012, 6 pages.
Ding et al., MS Analysis of Single-Nucleotide Differences in Circulating Nucleic Acids: Application to Noninvasive Prenatal Diagnosis, Proceedings of the National Academy of Sciences of the United States (PNAS), National Academy of Science US, vol. 101, No. 29, Jul. 20, 2004, pp. 10762-10767.
European Application No. 07763674.4, Extended European Search Report dated Jul. 31, 2009, 10 pages.
European Application No. 08776038.5, Office Action dated Aug. 3, 2010, 7 pages.
European Application No. 12173422.2, Extended European Search Report dated Nov. 23, 2012, 10 pages.
European Application No. 12175754.6, Extended European Search Report dated Nov. 23, 2012, 12 pages.
European Application No. 12180129.4, Extended European Search Report dated Sep. 9, 2014, 15 pages.
European Application No. 12180133.6, Extended European Search Report dated Jun. 25, 2014, 10 pages.
European Application No. 12180138.5, Partial European Search Report dated Dec. 10, 2014, 12 pages.
Hui, Noninvasive Prenatal Testing for Aneuploidy Using Cell-free DNA—New Implications for Maternal Health, Obstetric Medicine, vol. 9, No. 4, 2016, pp. 148-152.
Japanese Application No. Application no. 2010-517480, Office Action dated Jun. 25, 2013, 11 pages (6 pages of Original Document and 5 pages of English Translation).
Japanese Application No. Application No. 2015-090264, Office Action dated Mar. 15, 2016, 6 pages (2 pages of Original Document and 4 pages of English Translation).
Korean Application No. 10-2016-7021214, Office Action dated Nov. 21, 2016, 12 pages (6 pages of Original Document and 6 pages of English Translation).
Lo et al., Plasma Nucleic Acid Analysis by Massively Parallel Sequencing: Pathological Insights and Diagnostic Implications, Journal of Pathology, vol. 225, No. 3, 2011, pp. 318-323.
Marzese et al., Diagnostic and Prognostic Value of Circulating Tumor-Related DNA in Cancer Patients, Expert Review of Molecular Diagnostics, vol. 13, No. 8, Nov. 2013, pp. 827-844.
Mouliere et al., Circulating Tumor-Derived DNA is Shorter Than Somatic DNA in Plasma, Proceedings of the National Academy of Sciences, vol. 112, No. 11, Mar. 17, 2015, pp. 3178-3179.
International Application No. PCT/EP2010/066935, International Preliminary Report on Patentability dated May 18, 2012, 7 pages.
International Application No. PCT/GB2008/002524, International Search Report and Written Opinion dated Oct. 30, 2008, 28 pages.
International Application No. PCT/IB2012/000015, International Search Report and Written Opinion dated Apr. 27, 2012, 9 pages.
Wataganara et al., Debates on Fetal Fraction Measurement and DNA-Based Noninvasive Prenatal Screening: Time for Standardisation, BJOG, vol. 123, No. S3, 2016, pp. 31-35.
U.S. Appl. No. 13/789,553, Notice of Allowance dated Oct. 5, 2017, 10 pages.
U.S. Appl. No. 14/089,720, Non-Final Office Action dated Aug. 23, 2016, 15 pages.
U.S. Appl. No. 14/089,720, Non-Final Office Action dated Jun. 14, 2017, 18 pages.
U.S. Appl. No. 14/089,720, Notice of Allowance dated Mar. 30, 2018, 9 pages.
U.S. Appl. No. 15/587,662, Non-Final Office Action dated Jan. 25, 2018, 12 pages.
U.S. Appl. No. 15/587,662, Notice of Allowability dated Jul. 30, 2018, 8 pages.
U.S. Appl. No. 15/587,662, Notice of Allowance dated Jun. 20, 2018, 9 pages.
U.S. Appl. No. 15/587,662, Supplemental Notice of Allowability dated Oct. 17, 2018, 5 pages.
U.S. Appl. No. 15/411,695, Non-Final Office Action dated Sep. 19, 2019, 10 pages.
U.S. Appl. No. 15/411,695, Notice of Allowance dated Apr. 2, 2020, 7 pages.
Agarwal et al., Commercial Landscape of Noninvasive Prenatal Testing in the United States, Prenatal Diagnosis, vol. 33, Issue No. 6, Jun. 2013, pp. 521-531.
Australian Application No. AU2013229186, First Examination Report dated Dec. 1, 2015, 5 pages.
Australian Application No. AU2013229186, Notice of Acceptance dated Nov. 14, 2016, 3 pages.
Australian Application No. AU2017201258, First Examination Report dated May 11, 2018, 4 pages.
Australian Application No. AU2017201258, Notice of Acceptance dated Apr. 5, 2019, 3 pages.
Australian Application No. AU2017201258, Second Examination Report dated Sep. 3, 2018, 5 pages.
Bauer et al., A Prospective Analysis of Cell-Free Fetal DNA Concentration in Maternal Plasma as an Indicator for Adverse Pregnancy Outcome, Prenatal Diagnosis, vol. 26, No. 9, Jul. 11, 2006, pp. 831-836.
Bianchi et al., Large Amounts of Cell-Free Fetal DNA are Present in Amniotic Fluid, Clinical Chemistry, vol. 47, No. 10, Oct. 2001, pp. 1867-1869.
Canadian Application No. CA2,865,523, Notice of Allowance dated Jan. 4, 2018, 1 page.
Canadian Application No. CA2,865,523, Office Action dated Jan. 11, 2016, 5 pages.
Canadian Application No. CA2,973,025, Office Action dated Aug. 14, 2018, 4 pages.
Canadian Application No. CA2,973,025, Office Action dated Aug. 27, 2019, 9 pages.
Canadian Application No. CA3,010,254, Office Action dated Mar. 22, 2019, 4 pages.
Chan et al., Cancer Genome Scanning in Plasma: Detection of Tumor-Associated Copy Number Aberrations, Single-Nucleotide Variants, and Tumoral Heterogeneity by Massively Parallel Sequencina, Clinical Chemistry, vol. 59, No. 1, Jan. 2013, pp. 211-224.
Chan et al., Hypermethylated RASSF1A in Maternal Plasma: A Universal Fetal DNA Marker that Improves the Reliability of Noninvasive Prenatal Diagnosis, Clinical Chemistry, vol. 52, No. 12, Dec. 31, 2006, pp. 2211-2218.
Chan et al., Molecular Characterization of Circulating EBV DNA in the Plasma of Nasopharyngeal Carcinoma and Lymphoma Patients, Cancer Research, vol. 63, No. 9, May 1, 2003, pp. 2028-2032.
Chan et al., Persistent Aberrations in Circulating DNA Integrity after Radiotherapy are Associated with Poor Prognosis in Nasopharyngeal Carcinoma Patients, Imaging, Diagnosis, Prognosis, Clinical Cancer Research, vol. 14, Issue No. 13, Jul. 1, 2008, pp. 4141-4145.
Chan et al., Size Distributions of Maternal and Fetal DNA in Maternal Plasma, Clinical Chemistry, vol. 50, No. 1, Jan. 2004, pp. 88-92.
Chim et al., Detection of Placental Epigenetic Signature of Maspin Gene in Material Plasma, XP-002355638, PNAS, vol. 102, No. 41, Oct. 11, 2005, pp. 14753-14758.
Chiu et al., Application of Fetal DNA in Maternal Plasma for Noninvasive Prenatal Diagnosis, Expert Review of Molecular Diagnostics, vol. 2, No. 1, Jan. 2002, pp. 32-40.
Chiu et al., Non-Invasive Prenatal Assessment of Trisomy 21 by Multiplexed Maternal Plasma DNA Sequencing: Large Scale Validity Study, BMJ, vol. 342, No. c7401, Jan. 11, 2011, pp. 1-9.
Chiu et al., Non-Invasive Prenatal Diagnosis by Single Molecule Counting Technologies, Trends in Genetics, vol. 25, No. 7, Jun. 18, 2009, pp. 324-331.
Chiu et al., Noninvasive Prenatal Diagnosis of Fetal Chromosomal Aneuploidy by Massively Parallel Genomic Sequencing of DNA in Maternal Plasma, Proceedings of the National Academy of Sciences, vol. 105, No. 51, Dec. 23, 2008, pp. 20458-20463.

(56) References Cited

OTHER PUBLICATIONS

Fan et al., Analysis of the Size Distributions of Fetal and Maternal Cell-Free ONA by Paired-End Sequencing, Clinical Chemistry, vol. 56, No. 8, Aug. 1, 2010, pp. 1279-1286.
Chinese Application No. CN201380013054.5, Office Action dated Apr. 1, 2016, 21 pages. (9 pages for the original document and 12 pages for the English translation).
Chinese Application No. CN201380013054.5, Office Action dated Dec. 14, 2016, 24 pages. (10 pages for the original document and 14 pages for the English translation).
Della Ragione et al., Differential DNA Methylation as a Tool for Noninvasive Prenatal Diagnosis (NIPD) of X Chromosome Aneuploidies, the Journal of Molecular Diagnostics, vol. 12, No. 6, Nov. 1, 2010, pp. 797-807.
Devonshire et al., Towards Standardisation of Cell-Free DNA Measurement in Plasma: Controls for Extraction Efficiency, Fragment Size Bias and Quantification, Anal Bioanal Chem., vol. 406, Oct. 2014, pp. 6499-6512.
Diehl et al., Detection and Quantification of Mutations in the Plasma of Patients with Colorectal Tumors, Proceedings of the National Academy of Sciences, vol. 102, No. 45, Nov. 8, 2005, pp. 16368-16373.
Ding et al., Other Applications of Single Nucleotide Polymorphisms, Trends in Biotechnology, Elsevier Publications, Cambridge, vol. 25, No. 7, Jun. 14, 2007, pp. 279-283.
Ellinger et al., Cell-Free Circulating DNA: Diagnostic Value in Patients with Testicular Germ Cell Cancer, the Journal of Urology, vol. 181, No. 1, Jan. 2009, pp. 363-371.
Elshimali et al., The Clinical Utilization of Circulating Cell Free DNA (CCFDNA) in Blood of Cancer Patients, Int. J. Mol. Sci., vol. 14, No. 9, Sep. 13, 2013, pp. 18925-18958.
European Application No. EP13757943.9, Extended European Search Report dated Sep. 7, 2015, 7 pages.
European Application No. EP13757943.9, Interlocutory Decision in Opposition Proceedings dated May 29, 2020, 29 pages.
European Application No. EP13757943.9, Notice of Decision to Grant dated Dec. 7, 2017, 1 page.
European Application No. EP13757943.9, Notice of Opposition dated Oct. 12, 2018, 18 pages.
European Application No. EP13757943.9, Notice of Opposition dated Oct. 17, 2018, 2 pages.
European Application No. EP13757943.9, Office Action dated Sep. 9, 2016, 3 pages.
European Application No. EP13757943.9, Summons to Attend Oral Proceedings mailed on Sep. 10, 2019, 17 pages.
European Application No. EP14193706.0, Extended European Search Report dated Mar. 18, 2015, 5 pages.
European Application No. EP14193706.0, Notice of Decision to Grant dated Jan. 12, 2017, 1 page.
European Application No. EP14193706.0, Office Action dated Nov. 3, 2015, 4 pages.
European Application No. EP16737075.8, Extended European Search Report dated Jun. 4, 2018, 12 pages.
European Application No. EP17202838.3, Extended European Search Report dated Jan. 19, 2018, 5 pages.
European Application No. EP17202838.3, Notice of Decision to Grant dated Mar. 28, 2019, 2 pages.
European Application No. EP17209781.8, Extended European Search Report dated May 25, 2018, 5 pages.
European Application No. EP17209781.8, Notice of Decision to Grant dated Sep. 19, 2019, 2 pages.
European Application No. EP19170660.5, Extended European Search Report dated Oct. 15, 2019, 6 pages.
European Application No. EP19201127.8, Extended European Search Report dated Jan. 30, 2020, 7 pages.
Fan et al., Detection of Aneuploidy with Digital PCR, Department of Bioengineering, Stanford University and Howard Hughes Medical Institute, May 8, 2007, 14 pages.

Fan et al., Noninvasive Diagnosis of Fetal Aneuploidy by Shotgun Sequencing DNA from Maternal Blood, Proceedings National Academy of Sciences, vol. 105, No. 42, Oct. 21, 2008, pp. 16266-16271.
Fan et al., Sensitivity of Noninvasive Prenatal Detection of Fetal Aneuploidy from Maternal Plasma Using Shotgun Sequencing is Limited only by Counting Statistics, PLoS One, vol. 5, No. 5, Article e10439, Mar. 2010, pp. 1-7.
Gang et al., Prediction of Clear Cell Renal Cell Carcinoma by Integrity of Cell-Free DNA in Serum, Urology, vol. 75, Issue 2, Feb. 2010, pp. 262-265.
Giacona et al., Cell-Free DNA in Human Blood Plasma: Length Measurements in Patients with Pancreatic Cancer and Healthy Controls, Pancreas, vol. 17, No. 1, Jul. 1998, pp. 89-97.
Jahr et al., DNA Fragments in the Blood Plasma of Cancer Patients: Quantitations and Evidence for their Origin from Apoptotic and Necrotic Cells, Cancer Research, vol. 61, No. 4, Feb. 15, 2001, pp. 1659-1665.
Jiang et al., Increased Plasma DNA Integrity Index in Head and Neck Cancer Patients, International Journal of Cancer, vol. 119, No. 11, Dec. 1, 2006, pp. 2673-2676.
Jiang et al., Lengthening and Shortening of Plasma DNA in Hepatocellular Carcinoma Patients, PNAS, vol. 112, No. 11, Feb. 2, 2015, pp. E1317-E1325.
Japanese Application No. JP2014-560451, Office Action dated Feb. 23, 2016, 10 pages. (3 pages for the original document and 7 pages for the English translation).
Japanese Application No. JP2017-000134, Office Action dated Dec. 12, 2017, 6 pages. (2 pages for the original document and 4 pages for the English translation).
Japanese Application No. JP2017-536833, Office Action dated May 8, 2018, 5 pages. (2 pages for the original document and 3 pages for the English translation).
Japanese Application No. JP2018-156137, Office Action dated Sep. 3, 2019, 8 pages. (3 pages for the original document and 5 pages for the English translation).
Karoui et al., Getting More from Digital SNP Data, Statistics in Medicine, vol. 25, 2006, pp. 3124-3133.
Kohler et al., Levels of Plasma Circulating Cell Free Nuclear and Mitochondrial DNA as Potential Biomarkers for Breast Tumors, Molecular Cancer, vol. 8, No. 105, Nov. 17, 2009, pp. 1-8.
Korbel et al., Paired-End Mapping Reveals Extensive Structural Variation in the Human Genome, Science, vol. 318, No. 5849, Oct. 19, 2007, pp. 420-426.
Korean Application No. KR10-2017-7022238, Notice of Decision to Grant dated Oct. 25, 2018, 2 pages. (1 page for the original document and 1 page for the English translation).
Korean Application No. KR10-2017-7022238, Office Action dated Jun. 24, 2018, 6 pages. (3 pages for the original document and 3 pages for the English translation).
Landau et al., Evolution and Impact of Subclonal Mutations in Chronic Lymphocytic Leukemia, Cell, vol. 152, No. 4, Feb. 14, 2013, pp. 714-726.
Landau et al., Mutations Driving CLL and Their Evolution in Progression and Relapse, Nature, vol. 526, Oct. 22, 2015, pp. 525-530.
Lapaire et al., Cell-Free Fetal DNA in Amniotic Fluid: Unique Fragmentation Signatures in Euploid and Aneuploid Fetuses, Clinical Chemistry, vol. 53, No. 3, Mar. 2007, pp. 405-411.
Lapaire et al., Array-CGH Analysis of Cell-Free Fetal DNA in 10 mL of Amniotic Fluid Supernatant, Prenatal Diagnosis, vol. 27, No. 7, Jul. 2007, pp. 616-621.
Lapaire et al., Larger Columns and Change of Lysis Buffer Increase the Yield of Cell-Free DNA Extracted from Amniotic Fluid, Clinical Chemistry, vol. 52, No. 1, Jan. 2006, pp. 156-157.
Larrabee et al., Microarray Analysis of Cell-Free Fetal DNA in Amniotic Fluid: A Prenatal Molecular Karyotype, the American Society of Human Genetics, XP-002413186, vol. 75, No. 3, Sep. 1, 2004, pp. 485-491.
Leary et al., Detection of Chromosomal Alterations in the Circulation of Cancer Patients with Whole-Genome Sequencing, Science Translational Medicine, vol. 4, No. 162, Nov. 28, 2012, pp. 1-21.

(56) References Cited

OTHER PUBLICATIONS

Lecoeur, Nuclear Apoptosis Detection by Flow Cytometry: Influence of Endogenous Endonucleases, Experimental Cell Research, vol. 277, No. 1, Jul. 1, 2002, pp. 1-14.
Li et al., Size Separation of Circulatory DNA in Maternal Plasma Permits Ready Detection of Fetal DNA Polymorphisms, Clinical Chemistry, Molecular Diagnostics and Genetics, vol. 50, No. 6, Jun. 2004, pp. 1002-1011.
Liu et al., Decoding Circulating Nucleic Acids in Human Serum Using Microfluidic Single Molecule Spectroscopy, Journal of the American Chemical Society, vol. 132, No. 16, Apr. 5, 2010, pp. 5793-5798.
Lo et al., Digital PCR for the Molecular Detection of Fetal Chromosomal Aneuploidy, Proceedings of the National Academy of Sciences, vol. 104, No. 32, Aug. 7, 2007, pp. 13116-13121.
Lo et al., Maternal Plasma DNA Sequencing Reveals the Genome-Wide Genetic and Mutational Profile of the Fetus, Science Translation Medicine, vol. 2, No. 61, Dec. 8, 2010, pp. 1-13.
Lo et al., Presence of Fetal DNA in Maternal Plasma and Serum, the Lancet, vol. 350, No. 9076, Aug. 16, 1997, pp. 485-487.
Lo et al., Quantitative Analysis of Fetal DNA in Maternal Plasma and Serum: Implications for Noninvasive Prenatal Diagnosis, the American Journal of Human Genetics, vol. 62, No. 4, Apr. 1998, pp. 768-775.
Lun et al., Microfluidics Digital PCR Reveals a Higher than Expected Fraction of Fetal DNA in Maternal Plasma, Clinical Chemistry, vol. 54, No. 10, Oct. 2008, pp. 1664-1672.
Lun et al., Noninvasive Prenatal Diagnosis of Monogenic Diseases by Digital Size Selection and Relative Mutation Dosage on DNA in Maternal Plasma, Proceedings of the National Academy of Sciences of the United States of America, vol. 105, No. 50, Dec. 16, 2008, pp. 19920-19925.
Maron et al., Prenatal Diagnosis Using Cell-Free Nucleic Acids in Maternal Body Fluids: A Decade of Progress, American Journal of Medical Genetics Part C (Seminars in Medical Genetics), vol. 145C, Issue 1, Feb. 15, 2007, pp. 5-17.
Meyer et al., Analysis of the Transcriptional Complexity of *Arabidopsis thaliana* by Massively Parallel Signature Sequencing, Nature Biotechnology, vol. 22, No. 8, Aug. 2004, pp. 1006-1011.
Mouliere et al., High Fragmentation Characterizes Tumour-Derived Circulating DNA, PLOS One, vol. 6, No. 9, e23418, Sep. 2011, pp. 1-10.
Mouliere et al., The Importance of Examining the Proportion of Circulating Dna Originating from Tumor, Microenvironment and Normal Cells in Colorectal Cancer Patients, Journal, Expert Opinion on Biological Therapy, vol. 12, No. 1, Jun. 2012, pp. S209-S215.
Nygren et al., Quantification of Fetal DNA by Use of Methylation-Based DNA Discrimination, Clinical Chemistry, vol. 56, No. 10, Aug. 20, 2010, pp. 1627-1635.
Old et al., Candidate Epigenetic Biomarkers for Non-Invasive Prenatal Diagnosis of Down Syndrome, Reproductive BioMedicine Online, vol. 15, No. 2, Jun. 21, 2007, pp. 227-235.
Palomaki et al., DNA Sequencing of Maternal Plasma to Detect Down Syndrome: An International Clinical Validation Study, Genetics in Medicine, vol. 13, No. 11, Nov. 2011, pp. 913-920.
Panhard et al., Constructions of a Global Score Quantifying Allelic Imbalance Among Biallelic SIDP Markers in Bladder Cancer, Statistics in Medicine, vol. 22, Sep. 2003, pp. 3771-3779.
Papageorgiou et al., Fetal-Specific DNA Methylation Ratio Permits Noninvasive Prenatal Diagnosis of Trisomy 21, Nature Medicine, vol. 17, No. 4, Apr. 2011, pp. 510-513.
International Application No. PCT/CN2016/070785, International Search Report and Written Opinion dated Apr. 22, 2016, 7 pages.
International Application No. PCT/EP2010/066935, International Search Report and Written Opinion dated Feb. 23, 2011, 10 pages.
International Application No. PCT/IB2013/000312, International Preliminary Report on Patentability dated Sep. 18, 2014, 10 pages.
International Application No. PCT/IB2013/000312, International Search Report and Written Opinion dated Jun. 18, 2013, 13 pages.
International Application No. PCT/US2010/055655, International Search Report and Written Opinion dated Apr. 20, 2011, 20 pages.
Peter et al., Cell-Free DNA Fragmentation Patterns in Amniotic Fluid Identify Genetic Abnormalities and Changes Due to Storage, Diagnostic Molecular Pathology, vol. 17, No. 3, Sep. 2008, pp. 185-190.
Poon et al., Differential DNA Mehtylation between Fetus and Mother as a Strategy for Detecting Fetal DNA in Maternal Plasma, Clinical Chemistry, vol. 48, No. 1, Jan. 2002, pp. 35-41.
Reed et al., Non-Invasive Determination of the Paternal HLA Haplotype of a Fetus Using Kinetic PCR to Detect Fetal Microchimerism in Maternal Plasma, Bone Marrow Transplantation, vol. 29, No. 6, Mar. 2002, pp. 527-529.
Rubben et al., Somatic Deletion of the NFI Gene in a Neurofibromatosis Type I-Associated Malignant Melanoma Demonstrated by Digital PCR, Molecular Cancer, vol. 5, No. 36, Sep. 10, 2006, 9 pages.
Schwarzenbach et al., Cell-Free Nucleic Acids as Biomarkers in Cancer Patients, Nature Reviews Cancer, Advance Online Publication, vol. 11, No. 6, Jun. 2011, pp. 426-437.
Singaporean Application No. SG11201705685V, Notice of Decision to Grant dated Oct. 3, 2019, 3 pages.
Sozzi et al., Detection of Microsatellite Alterations in Plasma DNA of Non-Small Cell Lung Cancer Patients: A Prospect for Early Diagnosis, Clinical Cancer Research, vol. 5, Oct. 1999, pp. 2689-2692.
Sparks et al., Noninvasive Prenatal Detection and Selective Analysis of Cell-Free DNA Obtained from Maternal Blood: Evaluation for Trisomy 21 and Trisomy 18, American Journal of Obstetrics & Gynecology, vol. 206, No. 4, Apr. 2012, pp. 319.e1-319.e9.
Stolovitzky et al., Statistical Analysis of MPSS Measurements: Application to the Study of LPS-activated Macrophage Gene Expression, Proceedings of the National Academy of Sciences, vol. 102, No. 5, Feb. 1, 2005, pp. 1402-1407.
Swarup et al., Circulating (Cell-Free) Nucleic Acids—a Promising, Non-Invasive Tool for Early Detection of Several Human Diseases, FEBS Letters, vol. 581, Feb. 2, 2007, pp. 795-799.
Tong et al., Epigenetic-Genetic Chromosome Dosage Approach for Fetal Trisomy 21 Detection Using an Autosomal Genetic Reference Marker, PLOS One, vol. 5, No. 12, e15244, XP-002659895, Dec. 2010, 9 pages.
Tong et al., Noninvasive Prenatal Detection of Trisomy 21 by an Epigenetic-Genetic Chromosome-Dosage Approach, Clinical Chemistry, Molecular Diagnostics and Genetics, vol. 56, No. 1, Jan. 1, 2010, pp. 90-98.
Tsui et al., High Resolution Size Analysis of Fetal DNA in the Urine of Pregnant Women by Paired-End Massively Parallel Sequencing, PLoS One, vol. 7, No. 10, e48319, Oct. 31, 2012, pp. 1-7.
Tsui et al., Noninvasive Prenatal Diagnosis of Hemophilia by Microfluidics Digital PCR Analysis of Maternal Plasma DNA, Blood, vol. 117, No. 13, Mar. 31, 2011, pp. 3684-3691.
Wang et al., BRAF Mutations in Colon Cancer are Not Likely Attributable to Defective DNA Mismatch Repair, Cancer Research, vol. 62, Sep. 1, 2003, pp. 5209-5212.
Wang et al., Increased Plasma DNA Integrity in Cancer Patients, Cancer Research, vol. 63, Jul. 15, 2003, pp. 3966-3968.
Warren et al., Transcription Factor Profiling in Individual Hematopoietic Progenitors by Digital RT-PCR, PNAS, vol. 103, No. 47, Nov. 21, 2006, pp. 17807-17812.
Yu et al., Size-Based Molecular Diagnostics Using Plasma DNA for Noninvasive Prenatal Testing, Proceedings of the National Academy of Sciences, vol. 111, No. 23, Jun. 10, 2014, pp. 8583-8588.
Zheng et al., Nonhematopoietically Derived DNA is Shorter than Hematopoietically Derived DNA in Plasma: A Transplantation Model, Clinical Chemistry, vol. 58, No. 3, Mar. 2012, pp. 549-558.
Zhou et al., Counting Alleles Reveals a Connection Between Chromosome 18q Loss and Vascular Invasion, Nature Biotechnology, vol. 19, No. 1, Jan. 2001, pp. 78-81.
Communication of a notice of opposition dated Jul. 23, 2020 in EP Patent Application No. 17209781.8. 23 pages.
English translation of Office Action dated Aug. 25, 2020 in JP Patent Application No. 2020-105483. 5 pages.

2100
2110 — Measure amounts of DNA fragments corresponding to various sizes
2120 — Calculate a first value of a first parameter based on based on the amounts of DNA fragments at multiple sizes
2130 — Compare the first value to a reference value
2140 — Determine a classification of a level of cancer in the organism based on the comparison
FIG. 21

| | Gain | Loss | Reference |
|---|---|---|---|
| Colorectal | 7p, 7q, 8q, 11q, 13q,and 20q, | 5q, 8p, 17p, 18p, 18q and 20p, | (Nakao et al. Carcinogenesis 2004;25: 1345-1357.) (Tsafrir et al. Cancer Res 2006; 66: 2129-2137) |
| Breast | 1q, 6p, 8q, 11q, 16p, 17q, 19, and 20q | 6q, 13q, 16q, 17p, and 22q | (Tirkkonen et al. Gene Chromosome Canc 1998; 21: 177-184) (Richard et al. Int J Cancer 2000; 89: 305-310) (Pinkel et al. Nat Genet 1998; 20: 207-211) (Persson et al. Gene Chromosome Canc 1999; 25: 115-122) (Nishizaki et al. Int J Cancer 1997; 74: 513 - 517) |
| Lung | 1q, 3q, 5p,and 8q | 3p, 6q, 8p, 9p, 13q, and 17p | (Berrieman et al. Brit J Cancer 2004; 90: 900-905) (Luk et al. Cancer Genet Cytogen 2001; 125: 87 - 99) (Petersen et al. Cancer Res 1997; 57: 2331-2335) (Pei et al. Gene Chromosome Canc 2001; 31: 282-287) |
| HCC | 1q, 8q, 17q and 20q | 4q, 6q, 8p, 13q, 16q and 17p | (Kusano et al. Cancer 2002; 94: 746-751) (Laurent-Puig et al. Gastroenterology 2001; 120: 1763-1773) (Moinzadeh et al. Brit J Cancer 2005; 92: 935-941) |
| Ovarian | 20q, 3q, 1q, 8q, 12p, 11q, and 17q | Xp, 18q, 4q, 9p, and 13q | (Taetle et al. Gene Chromosome Canc 1999; 25: 290-300) (Schraml et al. Am J Pathol 2003; 163: 985 - 992) (Sonoda et al. Gene Chromosome Canc 1997; 20: 320-328) |

FIG. 22

SIZE-BASED SEQUENCING ANALYSIS OF CELL-FREE TUMOR DNA FOR CLASSIFYING LEVEL OF CANCER

CROSS-REFERENCES TO RELATED APPLICATION

This application is a continuation of U.S. patent application Ser. No. 15/411,695, entitled "SIZE-BASED ANALYSIS OF CELL-FREE TUMOR DNA FOR CLASSIFYING LEVEL OF CANCER," filed on Jan. 20, 2017, which is a divisional of U.S. patent application Ser. No. 13/789,553, entitled "SIZE-BASED ANALYSIS OF FETAL OR TUMOR DNA FRACTION IN PLASMA," filed on Mar. 7, 2013, now U.S. Pat. No. 9,892,230, which claims the benefit of U.S. Provisional Patent Application No. 61/608,623, entitled "SIZE-BASED ANALYSIS OF FETAL DNA FRACTION IN MATERNAL PLASMA," filed on Mar. 8, 2012, and U.S. Provisional Patent Application No. 61/621,451, entitled "SIZE-BASED ANALYSIS OF FETAL DNA FRACTION IN MATERNAL PLASMA," filed on Apr. 6, 2012, which are herein incorporated by reference in their entirety for all purposes.

BACKGROUND

The discovery of cell-free fetal DNA in maternal plasma has opened up new possibilities for noninvasive prenatal diagnosis (Lo Y M D et al. *Lancet* 1997; 350:485-487). The mean/median fractional fetal DNA concentration has been reported to be approximately 3% to 10% (Lo Y M D et al. *Am J Hum Genet* 1998; 62:768-775; Lun F M F et al. *Cin Chem* 2008; 54:1664-1672). The fractional fetal DNA concentration is an important parameter which affects the performance of noninvasive prenatal diagnostic tests using maternal plasma DNA. For example, for the noninvasive prenatal diagnosis of fetal chromosomal aneuploidies (e.g. trisomy 21, trisomy 18 or trisomy 13), the higher the fractional fetal DNA concentration is, the higher will be the overrepresentation of DNA sequences derived from the aneuploid chromosome in maternal plasma. Indeed, it has been demonstrated that for every two times reduction in the fractional fetal DNA concentration in maternal plasma, the number of molecules that one would need to count to achieve aneuploidy detection would be four times (Lo Y M D et al. *Proc Natl Acad Sci USA* 2007; 104:13116-13121).

For the noninvasive prenatal detection of fetal trisomy by random massively parallel sequencing, the fractional fetal DNA concentration of a sample would affect the amount of sequencing that one would need to perform to achieve a robust detection (Fan H C and Quake S R. *PLoS One* 2010; 5:e10439). Indeed, a number of groups have included a quality control step in which the fractional fetal DNA concentration is first measured and only samples that contain more than a minimum fractional fetal DNA concentration would be eligible to generate a diagnostic result (Palomaki G E et al. *Genet Med* 2011; 13:913-920). Other groups have included the fractional fetal DNA concentration in their diagnostic algorithm for estimating the risk that a particular maternal plasma sample is obtained from an aneuploid pregnancy (Sparks A B et al. *Am J Obstet Gynecol* 2012; 206: 319.e1-9).

In addition to aneuploidy detection, the fractional fetal DNA concentration also similarly affects noninvasive prenatal diagnostic tests conducted using maternal plasma DNA for detecting monogenic diseases, e.g. the hemoglobinopathies (Lun F M F et al. *Proc Natl Acad Sci USA* 2008; 105:19920-19925) and hemophilia (Tsui N B Y et al. *Blood* 2011; 117:3684-3691). The fractional fetal DNA concentration also affects the depth of sequencing that one would need to perform for constructing a fetal genomewide genetic and mutational map, as well as fetal whole genome sequencing (Lo Y M D et al. *Sci Transl Med* 2010; 2:61ra91 and U.S. Patent Application 2011/0105353).

A number of methods have been described for measuring the fractional fetal DNA concentration. One approach is to measure the concentration of a fetal-specific, paternally-inherited sequence that is absent from the maternal genome. Examples of such sequences include the sequences on the Y chromosome that are present in male fetuses and sequences from the RHD gene in a Rhesus D positive fetus carried by a Rhesus D negative pregnant woman. One could also measure the total maternal plasma DNA using sequences that are present in both the mother and the fetus. To arrive at a fractional fetal DNA concentration, one could then calculate the ratio of the concentration of the fetal-specific, paternally-inherited sequence over the concentration of the total maternal plasma DNA.

Another example of sequences that one could use includes the use of single nucleotide polymorphisms (Lo Y M D et al. *Sci Transl Med* 2010; 2:61ra91). A disadvantage of using genetic markers for the measurement of the fractional fetal DNA concentration is that no single set of genetic markers would be informative for all fetus-mother pair. Yet another method that one could employ is the use of DNA sequences that exhibit fetal or placental-specific DNA methylation patterns in maternal plasma (Nygren A O et al. *Cin Chem* 2010; 56:1627-1635). The potential disadvantage of the use of DNA methylation markers is that there may be inter-individual variation in the level of DNA methylation. Furthermore, methods that are used for the detection of DNA methylation markers are typically complex, including the use of methylation-sensitive restriction enzyme digestion (Chan K C A et al. *Cin Chem* 2008; 52:2211-2218) or bisulfite conversion (Chim S S C et al. *Proc Natl Acad Sci USA* 2005; 102:14753-14758) or methylated DNA immunoprecipitation (MeDIP) (Papageorgiou E A et al. *Nat Med* 2011; 17: 510-513).

Since the fractional fetal DNA concentration is an important value, it is desirable to have additional methods and systems for determining the value.

BRIEF SUMMARY

Embodiments can provide methods and systems for estimating a fractional concentration of clinically-relevant DNA in a mixture of DNA from a biological sample based amounts of DNA fragments at various sizes. For example, the fractional concentration of fetal DNA in maternal plasma or tumor DNA in a patient's plasma can be determined. The size of DNA fragments is shown to be correlated with a proportion of fetal DNA and a proportion of tumor DNA. Calibration data points (e.g., as a calibration function) indicate a correspondence between values of a size parameter and the fractional concentration of the clinically-relevant DNA. For a given sample, a first value of a size parameter can be determined from the sizes of DNA fragments in a sample. A comparison of the first value to the calibration data points provides the estimate of the fractional concentration of the clinically-relevant DNA.

According to one embodiment, a method estimates a fractional concentration of clinically-relevant DNA in a biological sample, the biological sample including the clinically-relevant DNA and other DNA. For each size of a plurality of sizes, an amount of a plurality of DNA fragments from the biological sample corresponding to the size is measured. A computer system calculates a first value of a first parameter based on the amounts of DNA fragments at multiple sizes. The first parameter provides a statistical measure of a size profile of DNA fragments in the biological sample. One or more first calibration data points are obtained. Each first calibration data point specifies a fractional concentration of clinically-relevant DNA corresponding to a calibration value of the first parameter. The one or more calibration data points are determined from a plurality of calibration samples. The first value is compared to a calibration value of at least one calibration data point. The fractional concentration of the clinically-relevant DNA in the biological sample is estimated based on the comparison.

According to another embodiment, a method analyzes a biological sample of an organism. The biological sample includes DNA originating from normal cells and potentially from cells associated with cancer. At least some of the DNA is cell-free in the biological sample. For each size of a plurality of sizes, an amount of a plurality of DNA fragments from the biological sample corresponding to the size is measured. A computer system calculates a first value of a first parameter based on the amounts of DNA fragments at multiple sizes. The first parameter provides a statistical measure of a size profile of DNA fragments in the biological sample. The first value is compared to a reference value. A classification of a level of cancer in the organism is determined based on the comparison.

Other embodiments are directed to systems, portable consumer devices, and computer readable media associated with methods described herein.

A better understanding of the nature and advantages of the present invention may be gained with reference to the following detailed description and the accompanying drawings.

BRIEF DESCRIPTION OF THE DRAWINGS

FIG. 21 is a flowchart illustrating a method 2100 for analyzing a biological sample of an organism to determine a classification of a level of cancer according to embodiments of the present invention.

FIG. 22 is a table 2200 showing some common chromosomal aberrations seen in various types of cancers.

DEFINITIONS

Figure 1:
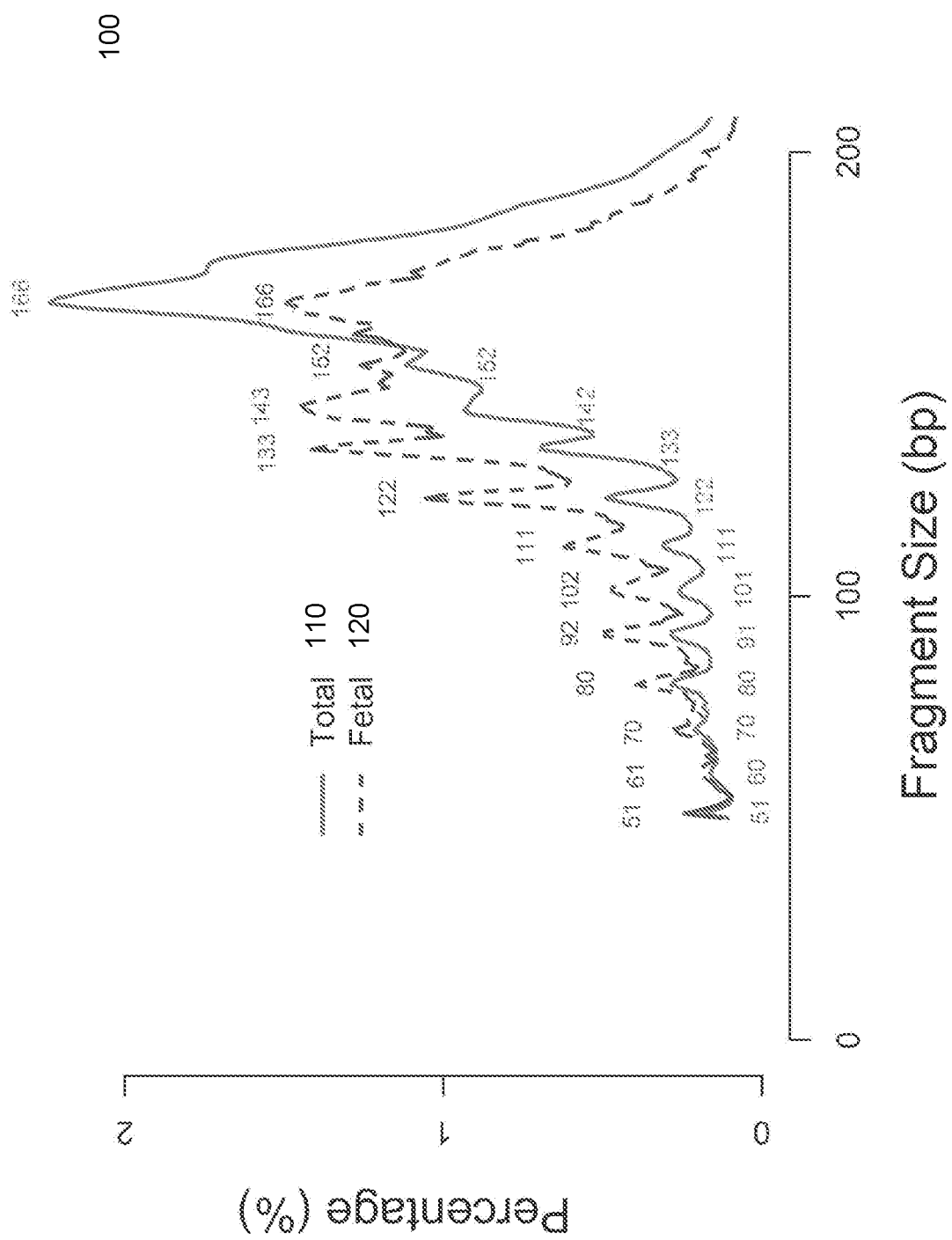
FIG. 1 shows a plot 100 of a size distribution of circulating cell-free DNA in maternal plasma according to embodiments of the present invention.

The term "biological sample" as used herein refers to any sample that is taken from a subject (e.g., a human, such as a pregnant woman) and contains one or more nucleic acid molecule(s) of interest. Examples include plasma, saliva, pleural fluid, sweat, ascitic fluid, bile, urine, serum, pancreatic juice, stool and cervical smear samples. The biological sample may be obtained from a human, an animal, or other suitable organism. A "calibration sample" corresponds to a biological sample whose clinically-relevant DNA fraction is known or determined via a calibration method, e.g., using an allele specific to the clinically relevant DNA. Examples of clinically-relevant DNA are fetal DNA in maternal plasma or tumor DNA in a patient's plasma.

As used herein, the term "locus" or its plural form "loci" is a location or address of any length of nucleotides (or base pairs) which has a variation across genomes. The term "sequence read" refers to a sequence obtained from all or part of a nucleic acid molecule, e.g., a DNA fragment. In one embodiment, just one end of the fragment is sequenced. Alternatively, both ends (e.g., about 30 bp from each end) of the fragment can be sequenced to generate two sequence reads. The paired sequence reads can then be aligned to a reference genome, which can provide a length of the fragment. In yet another embodiment, a linear DNA fragment can be circularized, e.g., by ligation, and the part spanning the ligation site can be sequenced.

The term "universal sequencing" refers to sequencing where adapters are added to the end of a fragment, and the primers for sequencing attached to the adapters. Thus, any fragment can be sequenced with the same primer, and thus the sequencing can be random.

The term fractional fetal DNA concentration is used interchangeably with the terms fetal DNA proportion and fetal DNA fraction, and refers to the proportion of fetal DNA molecules that are present in a biological sample (e.g., maternal plasma or serum sample) that is derived from the fetus (Lo Y M D et al. *Am J Hum Genet* 1998; 62:768-775; Lun F M F et al. *Clin Chem* 2008; 54:1664-1672). Similarly, the terms fractional tumor DNA concentration may be used interchangeably with the terms tumor DNA proportion and tumor DNA fraction, and refers to the proportion of tumor DNA molecules that are present in a biological sample.

The term "size profile" generally relates to the sizes of DNA fragments in a biological sample. A size profile may be a histogram that provides a distribution of an amount of DNA fragments at a variety of sizes. Various statistical parameters (also referred to as size parameters or just parameter) can be used to distinguish one size profile to another. One parameter is the percentage of DNA fragment of a particular size or range of sizes relative to all DNA fragments or relative to DNA fragments of another size or range.

Examples of "clinically-relevant" DNA include fetal DNA in maternal plasma and tumor DNA in the patient's plasma. Another example include the measurement of the amount of graft-associated DNA in the plasma of a transplant patient. A further example include the measurement of the relative amounts of hematopoietic and nonhematopoietic DNA in the plasma of a subject. This latter embodiment can be used for detecting or monitoring or prognosticating pathological processes or injuries involving hematopoietic and/or nonhematopoietic tissues.

A "calibration data point" includes a "calibration value" and a measured or known fractional concentration of the DNA of interest (i.e., the clinically-relevant DNA). The calibration value is a value of a size parameter as determined for a calibration sample, for which the fractional concentration of the clinically-relevant DNA is known. The calibration data points may be defined in a variety of ways, e.g., as discrete points or as a calibration function (also called a calibration curve or calibrations surface).

The term "level of cancer" can refer to whether cancer exists, a stage of a cancer, a size of tumor, how many deletions or amplifications of a chromosomal region are involved (e.g. duplicated or tripled), and/or other measure of a severity of a cancer. The level of cancer could be a number or other characters. The level could be zero. The level of cancer also includes premalignant or precancerous conditions associated with deletions or amplifications.

DETAILED DESCRIPTION

It is known that cell-free fetal DNA molecules in maternal plasma are generally shorter than the maternally-derived ones (Chan K C A et al. *Clin Chem* 2004; 50:88-92; Lo Y M D et al. *Sci Transl Med* 2010; 2:61ra91). The presence of fetal DNA results in a shift in the overall size distribution of maternal plasma DNA and the degree of shifting is associated with the fractional concentration of fetal DNA. By measuring particular values of the size profile of maternal plasma DNA, embodiments can obtain the fractional fetal DNA concentration in maternal plasma.

Apart from applications in noninvasive prenatal diagnosis, embodiments can also be used for measuring the fractional concentration of clinically useful nucleic acid species of different sizes in biological fluids, which can be useful for cancer detection, transplantation, and medical monitoring. It has previously been shown that tumor-derived DNA is shorter than the non-cancer-derived DNA in a cancer patient's plasma (Diehl F et al. *Proc Natl Acad Sci USA* 2005; 102:16368-16373). In the transplantation context, it has been shown hematopoietic-derived DNA is shorter than non-hematopoietic DNA (Zheng Y W et al. *Clin Chem* 2012; 58:549-558). For example, if a patient receives a liver from a donor, then the DNA derived from the liver (a nonhematopoietic organ in the adult) will be shorter than hematopoietic-derived DNA in the plasma (Zheng Y W et al. *Clin Chem* 2012; 58:549-558). Similarly, in a patient with myocardial infarction or stroke, the DNA released by the damaged nonhematopoietic organs (i.e. the heart and brain, respectively) would be expected to result in a shift in the size profile of plasma DNA towards the shorter spectrum.

I. Size Distribution

To demonstrate embodiments, we show in the following examples that one can measure the size profile, for example, by paired-end massively parallel sequencing or by electrophoresis (e.g. using a Bioanalyzer). The latter example is particularly useful because electrophoresis using a Bioanalyzer is a quick and relatively cheap procedure. This would allow one to rapidly perform this analysis as a quality control measure before one would subject a plasma DNA sample to the relatively expensive sequencing process.

FIG. 1 shows a plot 100 of a size distribution of circulating cell-free DNA in maternal plasma according to embodiments of the present invention. A size distribution can be obtained by measuring a size of DNA fragments and then counting the number of DNA fragments at various sizes, e.g., within the range of 50 bases to about 220 bases. Plot 100 shows two distributions. Distribution 110 is for all of the DNA fragments in the maternal plasma sample, and distribution 120 is only for DNA that is from the fetus. The horizontal axis is the size in base pairs (bp) of the DNA fragments. The vertical axis is the percentage of measured DNA fragments In FIG. 1, the size distribution of fetal-derived DNA in maternal plasma has been shown to be shorter than that of the maternally derived ones (Chan K C et al. *ClinChem* 2004; 50:88-92.) Recently, we have used paired-end massively parallel sequencing analysis to determine the high-resolution size distribution of the fetal-specific DNA and total DNA (mainly derived from the mother) in a pregnant woman. We showed that a main difference between the two species of DNA is that there is a reduction in the fraction of 166 bp DNA fragments and an increase proportion of shorter DNA of below 150 bp for the fetal-derived DNA (Lo Y M et al. *Sci Transl Med* 2010 2:61ra91).

Herein, we outline how an analysis of a size distribution of total DNA fragments in a maternal plasma sample (an example of a biological sample) would be useful for determining the fractional concentration of fetal DNA in maternal plasma. The increased fractional concentration of fetal DNA in maternal plasma would result in the shortening of the overall size distribution of the total DNA. In one embodiment, the relative abundance (an example of a parameter) of DNA fragments of approximately 144 bp and DNA fragments of approximately 166 bp could be used to reflect the fractional concentration of fetal DNA. In another embodiment, other parameters or combination of parameters regarding a size profile can be used to reflect the size distribution of plasma DNA.

Figure 2A:
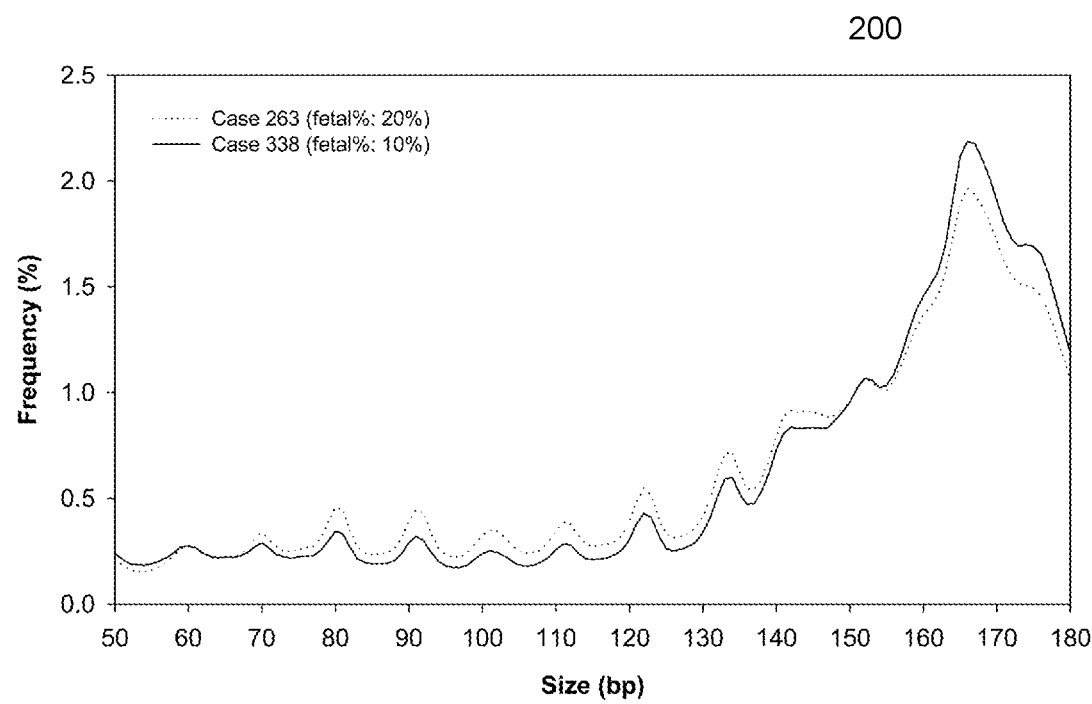
FIG. 2A shows a plot 200 of size distributions of fetal DNA in two maternal plasma samples ($1^{st}$ trimester pregnancies) with different fractional fetal DNA concentrations according to embodiments of the present invention.

FIG. 2A shows a plot 200 of size distributions of fetal DNA in two maternal plasma samples ($1^{st}$ trimester pregnancies) with different fractional fetal DNA concentrations according to embodiments of the present invention. Both of these two pregnant women were carrying male fetuses. The fractional fetal DNA concentrations were determined from the proportion of sequences from the Y chromosome among the total sequenced DNA fragments. Both samples were taken from pregnant women during the first trimester of their pregnancies. Case 338 (solid line, fractional fetal DNA concentration 10%) had a lower fractional fetal DNA concentration than Case 263 (dotted line, fractional fetal DNA concentration 20%). When compared with Case 263, Case 338 had a higher peak at 166 bp but the peaks for size below 150 bp were lower. In other words, DNA fragments shorter than 150 bp were more abundant in Case 263 whereas the fragments of approximately 166 bp were more abundant in Case 338. These observations are consistent with the hypothesis that the relative amounts of short and long DNA may be correlated to the fractional fetal DNA concentration.

Figure 2B:
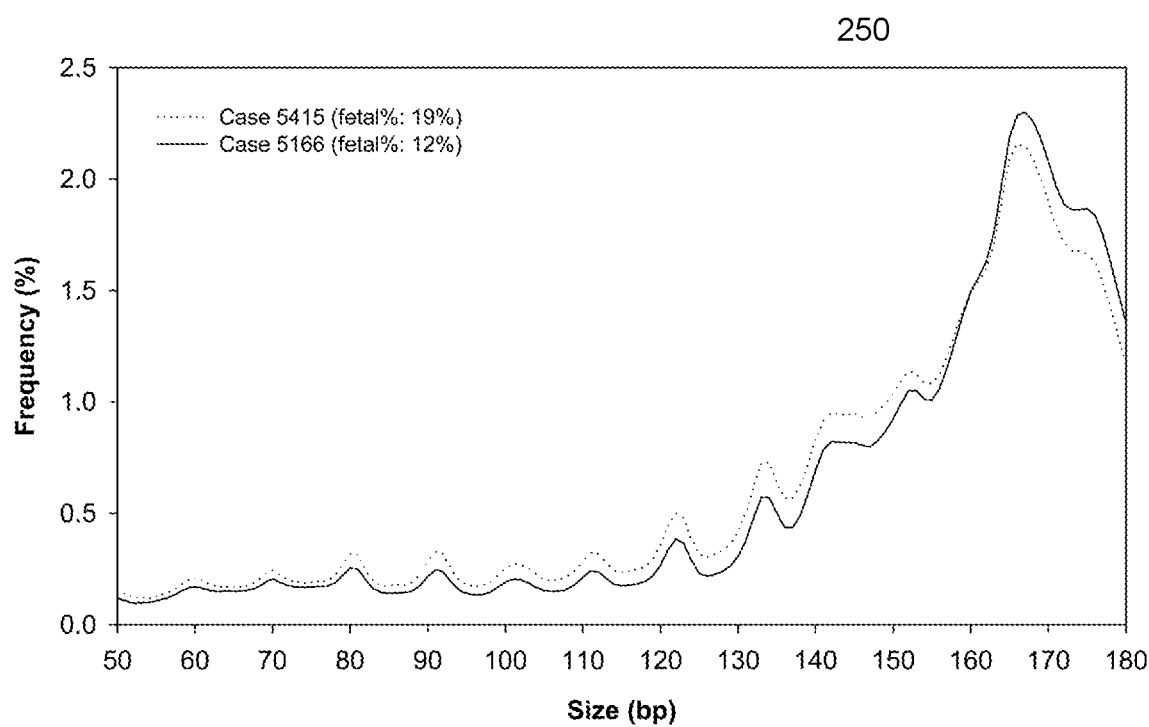
FIG. 2B shows a plot 250 of size distributions of DNA fragments in two maternal plasma samples ($2^{nd}$ trimester pregnancies) with different fractional fetal DNA concentrations according to embodiments of the present invention.

FIG. 2B shows a plot 250 of size distributions of DNA fragments in two maternal plasma samples ($2^{nd}$ trimester pregnancies) with different fractional fetal DNA concentrations according to embodiments of the present invention. Both samples were taken from pregnant women during the second trimester. Both of these two pregnant women were carrying male fetuses. The fractional fetal DNA concentrations were determined from the proportion of sequences from the Y chromosome among the total sequenced DNA fragments. Similar to the previous example, case 5415 (dotted line, with higher fractional fetal DNA concentration 19%) had higher peaks for sizes below 150 bp whereas case 5166 (solid line, with lower fractional fetal DNA concentration 12%) had a higher peak at 166 bp.

The correlation of different values of a size parameter to values of fractional fetal DNA concentration is shown in data plots below. Additionally, the size of fragments of tumor DNA is correlated to the percentage of tumor DNA fragments in a sample with tumor DNA fragments and DNA fragments from normal cells. Thus, the size of tumor fragments can also be used to determine the percentage of tumor fragments in the sample.

II. Method

Since the size of DNA fragments is correlated to a fractional concentration (also referred to as a percentage), embodiments can use this correlation to determine a fractional concentration of a particular type of DNA (e.g., fetal DNA or DNA from a tumor) in a sample. The particular type of DNA is clinically-relevant as that is the fractional concentration being estimated. Accordingly, a method can estimate a fractional concentration of clinically-relevant DNA in a biological sample based on a measured size of the DNA fragments.

Figure 3:
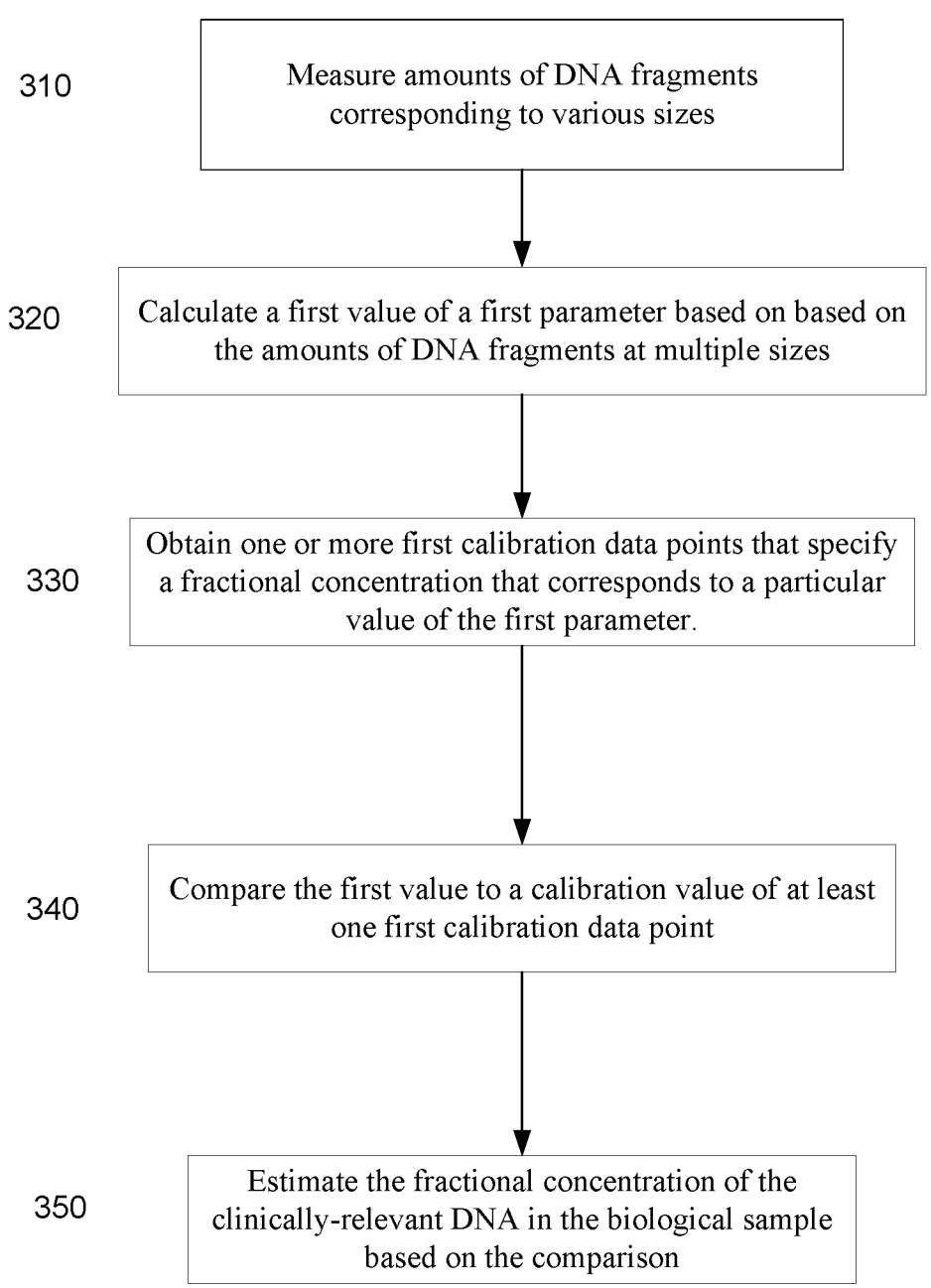
FIG. 3 is a flowchart of a method 300 illustrating a method of estimating a fractional concentration of clinically-relevant DNA in a biological sample according to embodiments of the present invention.

FIG. 3 is a flowchart of a method 300 illustrating a method of estimating a fractional concentration of clinically-relevant DNA in a biological sample according to embodiments of the present invention. The biological sample includes the clinically-relevant DNA and other DNA. The biological sample may be obtained from a patient, e.g., a female subject pregnant with a fetus. In another embodiment, the patient may have or be suspected of having a tumor. In one implementation, the biological sample may be received at a machine, e.g., a sequencing machine, which outputs measurement data (e.g., sequence reads) that can be used to determine sizes of the DNA fragments. Method 300 may be performed wholly or partially with a computer system, as can other methods described herein.

At block 310, amounts of DNA fragments corresponding to various sizes are measured. For each size of a plurality of sizes, an amount of a plurality of DNA fragments from the biological sample corresponding to the size can be measured. For instance, the number of DNA fragments having a length of 140 bases may be measured. The amounts may be saved as a histogram. In one embodiment, a size of each of the plurality of nucleic acids from the biological sample is measured, which may be done on an individual basis (e.g., by single molecule sequencing) or on a group basis (e.g., via electrophoresis). The sizes may correspond to a range. Thus, an amount can be for DNA fragments that have a size within a particular range.

The plurality of DNA fragments may be chosen at random or preferentially selected from one or more predetermined regions of a genome. For example, targeted enrichment may be performed, as described above. In another embodiment, DNA fragments may be randomly sequenced (e.g., using universal sequencing), and the resulting sequence reads can be aligned to a genome corresponding to the subject (e.g., a reference human genome). Then, only DNA fragments whose sequence reads align to the one or more predetermined regions may be used to determine the size.

In various embodiments, the size can be mass, length, or other suitable size measures. The measurement can be performed in various ways, as described herein. For example, paired-end sequencing and alignment of DNA fragments may be performed, or electrophoresis may be used. A statistically significant number of DNA fragments can be measured to provide an accurate size profile of the biological sample. Examples of a statistically significant number of DNA fragments include greater than 100,000; 1,000,000; 2,000,000, or other suitable values, which may depend on the precision required.

In one embodiment, the data obtained from a physical measurement, such as paired-end sequencing or electrophoresis, can be received at a computer and analyzed to accomplish the measurement of the sizes of the DNA fragments. For instance, the sequence reads from the paired-end sequencing can be analyzed (e.g., by alignment) to determine the sizes. As another example, the electropherogram resulting from electrophoresis can be analyzed to determines the sizes. In one implementation, the analyzing of the DNA fragments does include the actual process of sequencing or subjecting DNA fragments to electrophoresis, while other implementations can just perform an analysis of the resulting data.

At block 320, a first value of a first parameter is calculated based on the amounts of DNA fragments at multiple sizes. In one aspect, the first parameter provides a statistical measure of a size profile (e.g., a histogram) of DNA fragments in the biological sample. The parameter may be referred to as a size parameter since it is determined from the sizes of the plurality of DNA fragments.

The first parameter can be of various forms. Such a parameter is a number of DNA fragments at a particular size divided by the total number of fragments, which may be obtained from a histogram (any data structure providing absolute or relative counts of fragments at particular sizes). As another example, a parameter could be a number of fragments at a particular size or within a particular range divided by a number of fragments of another size or range. The division can act as a normalization to account for a different number of DNA fragments being analyzed for different samples. A normalization can be accomplished by analyzing a same number of DNA fragments for each sample, which effectively provides a same result as dividing by a total number fragments analyzed. Other examples of parameters are described herein.

At block 330, one or more first calibration data points are obtained. Each first calibration data point can specify a fractional concentration of clinically-relevant DNA corresponding to a particular value (a calibration value) of the first parameter. The fractional concentration can be specified as a particular concentration or a range of concentrations. A calibration value may correspond to a value of the first parameter (i.e., a particular size parameter) as determined from a plurality of calibration samples. The calibration data points can be determined from calibration samples with known fractional concentrations, which may be measured via various techniques described herein. At least some of the calibration samples would have a different fractional concentration, but some calibration samples may have a same fractional concentration In various embodiments, one or more calibration points may be defined as one discrete point, a set of discrete points, as a function, as one discrete point and a function, or any other combination of discrete or continuous sets of values. As an example, a calibration data point could be determined from one calibration value of a size parameter (e.g., number of fragments in a particular size or size range) for a sample with a particular fractional concentration. A plurality of histograms can be used, with a different histogram for each calibration sample, where some of the calibration samples may have the same fractional concentration.

In one embodiment, measured values of a same size parameter from multiple samples at the same fractional concentration could be combined to determine a calibration data point for a particular fractional concentration. For example, an average of the values of the size parameter may be obtained from the size data of samples at the same fractional concentration to determine a particular calibration data point (or provide a range that corresponds to the calibration data point). In another embodiment, multiple data points with the same calibration value can be used to determine an average fractional concentration.

In one implementation, the sizes of DNA fragments are measured for many calibration samples. A calibration value of the same size parameter is determined for each calibration sample, where the size parameter may be plotted against the known fractional concentration of the sample. A function may then be fit to the data points of the plot, where the functional fit defines the calibration data points to be used in determining the fractional concentration for a new sample.

At block 340, the first value is compared to a calibration value of at least one calibration data point. The comparison can be performed in a variety of ways. For example, the comparison can be whether the first value is higher or lower than the calibration value. The comparison can involve comparing to a calibration curve (composed of the calibration data points), and thus the comparison can identify the point on the curve having the first value of the first parameter. For example, a calculated value X of the first parameter (as determined from the measured sizes of DNA in the new sample) can be used as input into a function F(X), where F is the calibration function (curve). The output of F(X) is the fractional concentration. An error range can be provided, which may be different for each X value, thereby providing a range of values as an output of F(X).

In step 350, the fractional concentration of the clinically-relevant DNA in the biological sample is estimated based on the comparison. In one embodiment, one can determine if the first value of the first parameter is above or below a threshold calibration value, and thereby determine if the estimated fractional concentration of the instant sample is above or below the fractional concentration corresponding to the threshold calibration value. For example, if the calculated first value $X_1$ for the biological is above a calibration value $X_C$ then the fractional concentration $FC_1$ of the biological sample can be determined as being above the fractional concentration $FC_C$ corresponding to $X_C$. This comparison can be used to determine if a sufficient fractional concentration exists in the biological sample to perform other tests, e.g., testing for a fetal aneuploidy. This relationship of above and below can depend on how the parameter is defined. In such an embodiment, only one calibration data point may be needed.

In another embodiment, the comparison is accomplished by inputting the first value into a calibration function. The calibration function can effectively compare the first value to calibration values by identifying the point on a curve corresponding to the first value. The estimated fractional concentration is then provided as the output value of the calibration function.

In one embodiment, the value of more than one parameter can be determined for the biological sample. For example, a second value can be determined for a second parameter, which corresponds to a different statistical measure of the size profile of DNA fragments in the biological sample. The second value can be determined using the same size measurements of the DNA fragments, or different size measurements. Each parameter can correspond to a different calibration curve. In one implementation, the different values can be compared independently to different calibration curves to obtain a plurality of estimated fractional concentrations, which may then be averaged or used to provide a range as an output.

In another implementation, a multidimensional calibration curve can be used, where the different values of the parameters can be effectively be input to a single calibration function that outputs the fractional concentration. The single calibration function can result from a functional fit of all of the data points obtained from the calibration samples. Thus, in one embodiment, the first calibration data points and the second calibration data points can be points on a multidimensional curve, where the comparison includes identifying the multidimensional point having coordinates corresponding to the first value and the one or more second values.

III. Determining Size

The size distribution of plasma DNA can be determined, for example, but not limited to, using real-time PCR, electrophoresis and mass spectrometry analysis. In various embodiments, the measured size is a length, a molecular mass, or a measured parameter that is proportional to the length or mass, such as the mobility in a electrophoretogram and the time required to travel a fixed distance in electrophoresis or mass spectrometer. In another example, one can stain the DNA with an intercalating fluorescence dye, e.g. ethidium bromide or SYBR Green, where the amount of dye bound will be proportional to the length of the DNA molecule. One can determine the amount of dye bound by the intensity of the emitted fluorescence when UV light is shone on the sample. Some examples for measuring size and resulting data are described below.

A. First Fetal Sample Set Using Sequencing

Table 1 shows sample information and sequencing analyses for an example involving a fetal DNA fraction. Plasma samples were collected from 80 pregnant women, each carrying a single male fetus. Among these 80 pregnant women, 39 were carrying a euploid fetus, 18 were carrying a trisomy 21 (T21) fetus, 10 were carrying a trisomy 18 (T18) fetus, and 13 were carrying a trisomy 13 (T13) fetus. A size distribution of plasma DNA was determined using paired-end massively parallel sequencing. Sequencing libraries of maternal plasma DNA were constructed as previously described (Lo Y M et al. *Sci Transl Med* 2010; 2:61ra91), except that a 6-base barcode was introduced to the DNA molecules of each plasma sample through a triple-primer PCR amplification.

Two samples were introduced into one sequencing lane (i.e. 2-plex sequencing). In other embodiments, more than two samples can be introduced into one sequencing lane, e.g. 6, or 12, or 20, or more than 20. All libraries were sequenced by a Genome Analyzer IIx (Illumina) using the 36-bp×2 PE format. An additional 7 cycles of sequencing were performed to decode the index sequence on each sequenced plasma DNA molecule. The 36-bp sequence reads were aligned to the non-repeat-masked human reference genome (Hg18) (genome.ucsc.edu), using the Short Oligonucleotide Alignment Program 2 (SOAP2) (soap.genomics.org.cn). Paired end (PE) reads with individual members sequenced on the same cluster position on the flow cell and uniquely aligned to a single location in the human genome with the correct orientation and without any nucleotide mismatch were identified. In other embodiments, alignment may not be unique and mismatches may be allowed.

Only the PE reads that demonstrated an insert size 600 bp were retrieved for analysis. With these criteria, the size of the analyzed plasma DNA fragments in these experiments ranged from 36 bp to 600 bp. The size of each sequenced DNA fragment was inferred from the coordinates of the outermost nucleotides at each end of the sequenced fragments.

| Case type | No. of cases | Gestational age (weeks) median (range) | No. of PE reads (millions) median (range) | Fetal DNA fraction (%) median (range) |
|---|---|---|---|---|
| Euploid | 39 | 13.2 (11.3-15.1) | 4.7 (1.8-12.0) | 15.7 (5.9-25.7) |
| T21 | 18 | 13.0 (12.1-17.9) | 5.2 (2.5-8.9) | 13.8 (7.4-27.2) |
| T18 | 10 | 13.3 (12.1-14.2) | 4.9 (3.6-6.2) | 7.2 (4.8-16.7) |
| T13 | 13 | 12.4 (11.5-16.4) | 5.3 (2.7-7.7) | 7.5 (3.2-14.1) |
| All | 80 | 13.1 (11.3-17.9) | 4.9 (1.8-12.0) | 13.7 (3.2-27.2) |

Table 1 shows data for samples of various aneuploidy status. The data includes the number of cases, gestational age median and range, along with number of paired-end reads median and range and the fetal DNA fraction.

The fractional concentrations of fetal DNA in the maternal plasma samples were deduced from the amount of sequences aligning to chromosome Y as previously described (Chiu R W et al. *BMJ* 2011; 342:c7401). This technique is an example of a calibration method. Thus, the measured fetal DNA fraction in Table 1 can be used in calibration data points to estimate a fetal DNA fraction in a new sample. The samples used to collect the data in Table 1 may be considered calibration samples.

B. Second Fetal Sample Set Using Targeted Sequencing

Table 2 shows sample information and targeted enrichment of maternal plasma DNA according to embodiments of the present invention. Plasma samples were collected from 48 pregnant women, each carrying a single fetus. Among Only the PE reads that demonstrated an insert size 600 bp were retrieved for analysis. With these criteria, the size of the analyzed plasma DNA fragments in the current study ranged from 36 bp to 600 bp. The size of each sequenced DNA fragment was inferred from the coordinates of the outermost nucleotides at each end of the sequenced fragments. The fractional concentrations of fetal DNA in the maternal plasma samples were estimated from the ratio of fragments carrying the fetal-specific alleles and the alleles shared with the respective mothers.

| Case type | No. of cases | Gestational age (weeks) median (range) | No. of PE reads (millions) median (range) | Fetal DNA fraction (%) median (range) |
|---|---|---|---|---|
| Euploid | 21 | 13.0 (12.0-13.3) | 2.2 (1.7-3.0) | 13.5 (8.4-22.0) |
| T21 | 17 | 13.6 (12.6-20.9) | 2.1 (1.5-2.7) | 15.4 (8.7-22.7) |
| T18 | 9 | 12.7 (11.9-13.7) | 1.9 (1.7-3.1) | 10.5 (7.2-16.3) |
| T13 | 1 | 13 | 1.6 | 9.2 |
| All | 48 | 13.1 (11.9-20.9) | 2.1 (1.5-3.1) | 13.4 (7.2-22.7) | these 48 pregnant women, 21 were carrying a euploid fetus, 17 were carrying a trisomy 21 (T21) fetus, 9 were carrying a trisomy 18 (T18) fetus, and 1 was carrying a trisomy 13 (T13) fetus. These data, along with examples below, illustrate that embodiments can use targeted techniques. The size distribution of plasma DNA can be determined using paired-end massively parallel sequencing. In other embodiments, the size distribution of plasma DNA can be determined for example by not limited to using real-time PCR, electrophoresis and mass spectrometry analysis.

To obtain high-fold sequencing coverage of the target regions, the Agilent SureSelect Target Enrichment System was employed in one embodiment to design probes to capture DNA molecules from chr7 (0.9 Mb region), chr13 (1.1 Mb region), chr18 (1.2 Mb region) and chr21 (1.3 Mb region). In the probe design, exons on chr7, chr13, chr18, and the Down syndrome critical region on chr21 (21q22.1-q22.3) were first selected as target regions. Because chr13, chr18 and chr21 have less exonic regions than chr7, additional non-exonic regions on chr13, chr18, and the Down syndrome critical region on chr21 were introduced to balance the total length of the targeted region among the above four chromosomes. The selected non-exonic regions were 120 bp in length, uniquely mappable, with GC content close to 0.5 and evenly distributed over the targeted chromosomes Coordinates of all of the above exonic and non-exonic regions were submitted to the Agilent eArray platform for probe design. 500 ng of each maternal plasma DNA library was incubated with the capture probes for 24 h at 65° C. After hybridization, the targeted DNA molecules were eluted and amplified by a 12-cycle PCR according to manufacturer's instructions. Libraries with target enrichment were indexed and sequenced on a GA Ix (Illumina) using the 50-bp×2 PE format. An additional 7 cycles of sequencing were performed to decode the index sequence on each sequenced plasma DNA molecule. The 50-bp sequence reads were aligned to the non-repeat-masked human reference genome (Hg18) (genome.ucsc.edu), using the Short Oligonucleotide Alignment Program 2 (SOAP2) (soap.genomics.org.cn). PE reads with individual members were sequenced on the same cluster position on the flow cell and uniquely aligned to a single location in the human genome with the correct orientation. Two mismatches were allowed; complexity of the sequencing library was significantly reduced after target enrichment.

Table 2 shows data from targeted sequencing for samples of various aneuploidy status.

C. Electrophoresis for Fetal Sample

In addition to using massively parallel sequencing, the analysis of the size distribution of plasma DNA can be achieved by electrophoresis. Electrophoresis measures a time for a fragment to move through a medium. Particles of different sizes take different times to move through the medium. Thus, in one embodiment, microfluidic electrophoresis of sequencing library of maternal plasma DNA can be performed to determine the size distribution of the maternal plasma DNA.

Figure 4:
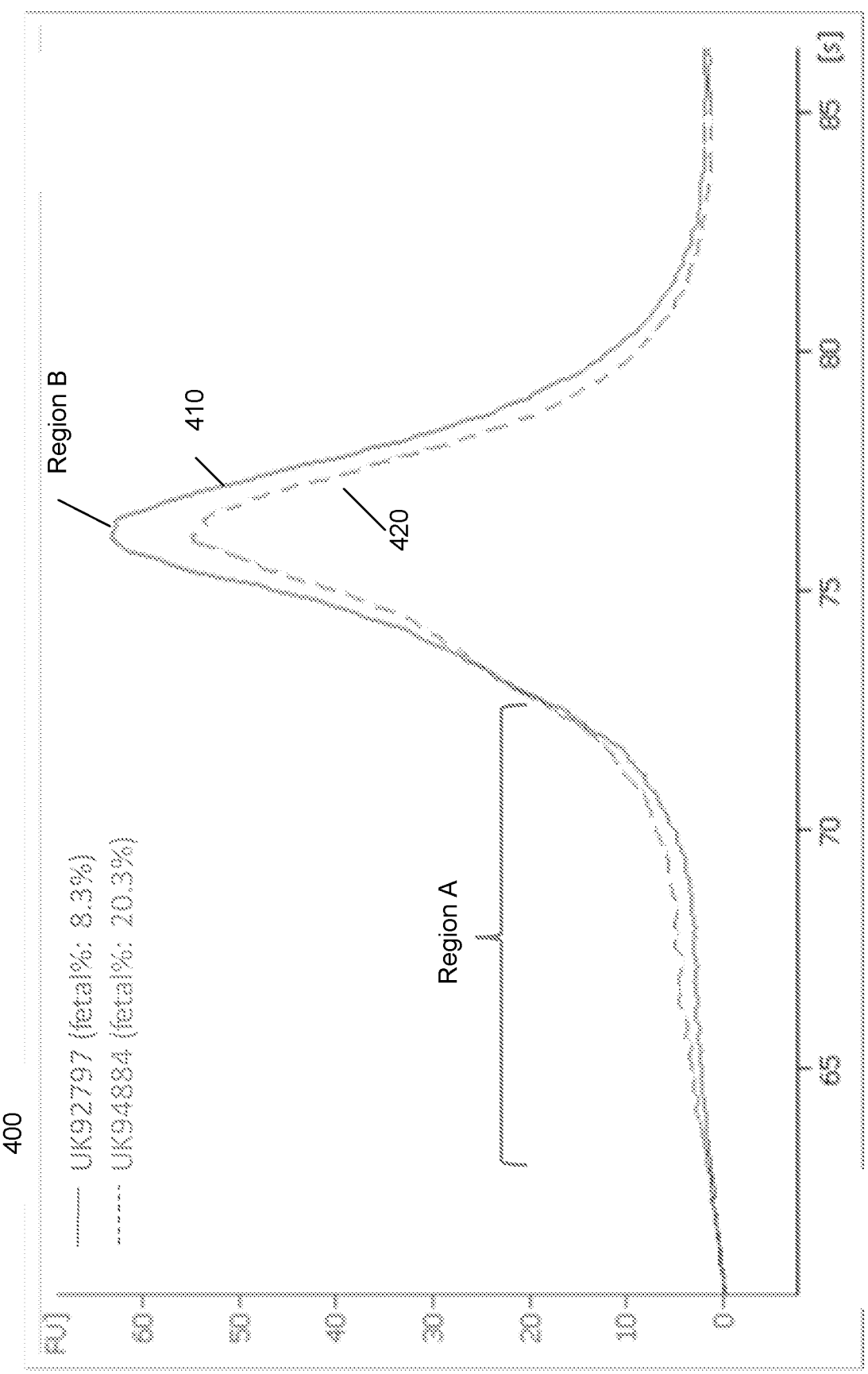
FIG. 4 is a plot 400 showing a size distribution (electropherogram) of maternal plasma DNA obtained using electrophoresis according to embodiments of the present invention.

FIG. 4 is a plot 400 showing a size distribution (electropherogram) of maternal plasma DNA obtained using electrophoresis according to embodiments of the present invention. The microfluidic electrophoresis was performed using the Agilent 2100 Bioanalyzer. The electropherograms of the sequencing libraries of two samples are shown in plot 400. The X-axis represents the time duration the DNA taken to reach the sensor and corresponds to the size of the DNA fragments. The Y-axis represents the fluorescence units (FU) of the DNA fragments passing through the sensor at a particular time.

The time duration a DNA fragment takes to reach the sensor is positively correlated with the size of the DNA fragment. The Bioanalyzer can automatically convert the time duration to fragment size by comparing the running time of the test sample to those of a mixture of DNA fragments with known lengths (i.e., a DNA ladder). The DNA sequencing libraries were subsequently sequenced using massively parallel sequencing and the fraction of chromosome Y sequences were used to determine the fractional fetal DNA concentrations of these samples.

In plot 400, the solid line 410 represents the sample UK92797 which had a fractional fetal DNA concentration of 8.3% and the dashed line 420 represents the sample UK94884 which had a fractional fetal DNA concentration of 20.3%. Comparing with sample UK92797, sample UK94884 (the sample with the higher fractional fetal DNA) had a relatively higher amount of DNA at electrophoretic time interval from 63 seconds to 73 seconds (region A) which corresponds to DNA size from 200 bp to 267 bp and a relatively lower amount of DNA at electrophoretic time of 76 s (region B), corresponding to a DNA size of ~292 bp According the manufacturer's protocol, DNA adaptors and primer sets which had a total size of 122 bp were introduced to the plasma DNA for sequencing library construction. Therefore, the region A corresponds to plasma DNA fragments approximately from 78 bp to 145 bp, and region B corresponds to plasma DNA fragments of approximately 170 bp. Such deduction can be adapted to different protocols for DNA library construction. For example, during the Illumina single-read sequencing library preparation, a total size of 92 bp from adapter/primer sets would be introduced, while this size would be 119 bp for the standard paired-end sequencing library preparation.

In another embodiment, the plasma DNA can be amplified by a whole genome amplification system known to those skilled in the art, e.g. the Rubicon Genomics PlasmaPlex WGA kit (www.rubicongenomics.com/products). The amplified products can then analyzed by the Bioanalyzer. In yet other embodiments, the amplified products can be analyzed by a electrophoretic system from e.g. Caliper (www.caliperls.com/products/labchip-systems). In yet other embodiments, the size distribution of plasma DNA can be analyzed directly, without amplification, using for example, a nanopore-based sequencer (e.g. from Oxford Nanopore Technologies (www.nanoporetech.com)), or a Helico DNA sequencer (www.helicosbio.com).

IV. Size Parameters

As mentioned above, various parameters can provide a statistical measure of a size profile of DNA fragments in the biological sample. A parameter can be defined using the sizes of all of the DNA fragments analyzed, or just a portion. In one embodiment, a parameter provides a relative abundance of short and long DNA fragments, where the short and long DNA may correspond to specific sizes or ranges of sizes.

To investigate if the overall size distribution of maternal plasma DNA can be used for reflecting the fractional fetal DNA concentration, we have used different parameters to quantify the relative abundance of short and long DNA, and determined the correlation between these parameters and fractional fetal DNA concentrations. The results of these investigations are provided in sections below. Parameters that we used, for illustration purposes, for reflecting the relative abundance of short DNA include:

i. Proportion of DNA fragments of 150 bp or below, which is labeled CF (size≤150). CF refers to cumulative frequency. Thus, CF (size≤150) refers to the cumulative frequency of fragments less than or equal to 150 bp;

ii. Ratio of the amounts of DNA fragments of ≤150 bp and DNA from 163 bp to 169 bp, which is labeled (CF (size≤150)/size(163-169));

iii. Ratio of the amounts of DNA fragments from 140 bp to 146 bp and DNA from 163 bp to 169 bp, which is labeled (size(140-146)/size(163-169));

iv. Ratio of the amounts of DNA fragments from 140 bp to 154 bp and DNA from 163 bp to 169 bp, which is labeled (size(140-154)/size(163-169)); and v. Ratio of the amounts of DNA fragments from 100 bp to 150 bp and DNA from 163 bp to 169 bp, which is labeled (size(100-150)/size(163-169)).

Other examples of parameters are the frequency counters of a histogram. In one embodiment, multiple parameters may be used. For example, the value of each parameter may give a difference percentage and then an average percentage can be determined. In another embodiment, each parameter corresponds to a different dimension of a multidimensional calibration function, where the values of the parameters for a new sample corresponds to a coordinate on the corresponding multidimensional surface.

V. Correlation of Size to Fractional Concentration

The two samples sets using sequencing are used to illustrate the correlation of various size parameters to fractional concentration. An analysis of the size of repeat elements is also provided. The electrophoresis data also shows a correlation between size parameters and fractional concentration.

A. First Sample Set

Figure 5A:
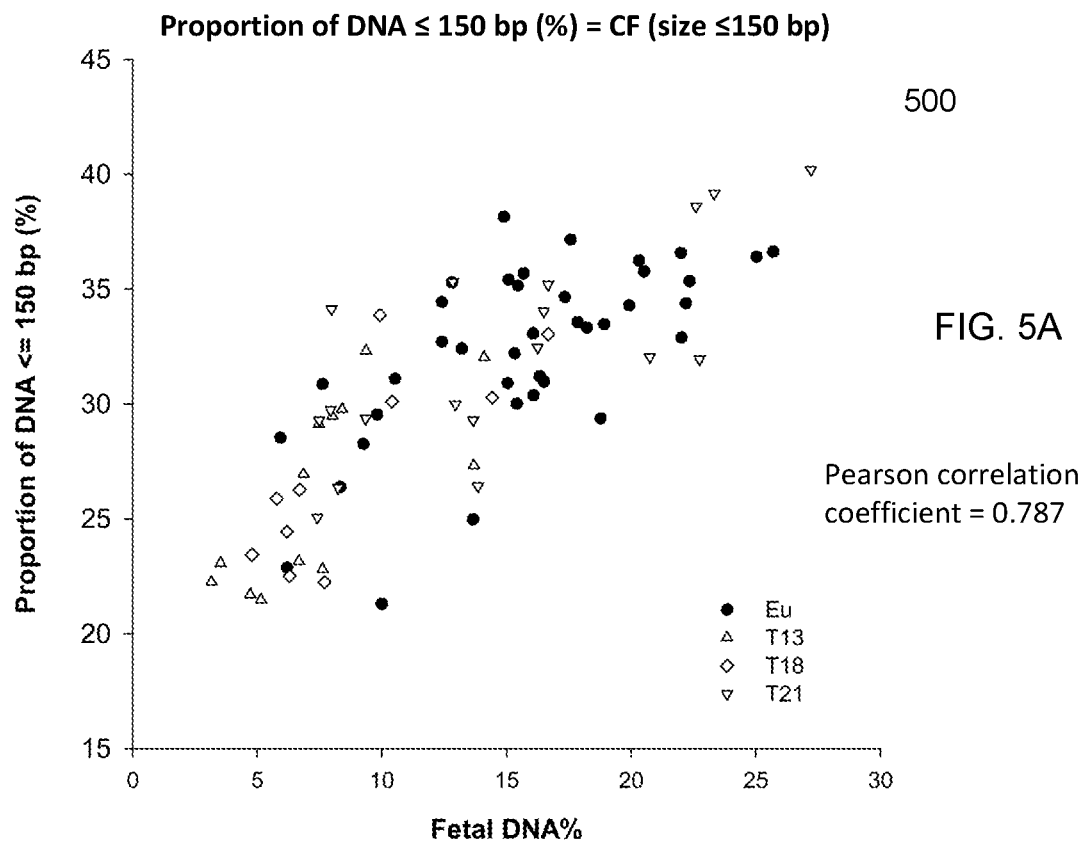
FIG. 5A is a plot 500 showing a proportion of DNA fragments that are 150 bp or below for samples having various fetal DNA percentage in maternal plasma according to embodiments of the present invention.

FIG. 5A is a plot 500 showing a proportion of DNA fragments that are 150 bp or below for samples having various fetal DNA percentage in maternal plasma according to embodiments of the present invention. The proportion of DNA ≤150 bp is plotted against the fractional fetal DNA concentration for the 80 maternal plasma samples. The euploid samples are represented by filled circles. The trisomy 13 (T13) samples are represented by unfilled triangles. The trisomy 18 (T18) samples are represented by unfilled rhombus and the trisomy 21 (T21) samples are represented by inverted unfilled triangles.

There is a positive relationship between the fractional fetal DNA concentration and the proportion of DNA ≤150 bp for all samples (Pearson correlation coefficient=0.787). The positive correlation between the size parameter and the fractional fetal DNA concentration appears to be consistent across samples with different fetal chromosomal status. These results suggest that the analysis of the size parameter is useful for estimating the fractional fetal DNA concentration in a maternal plasma sample. Accordingly, the data points in FIG. 5 can be used as the calibration data points of method 300. Then, if the parameter CF(size≤150) is determined to be 30 for a new sample, the fetal DNA percentage can be estimated as being between about 7% and 16%. The data points in FIG. 5 can also be used to determine a calibration function that fits the raw data points shown.

Figure 5B:
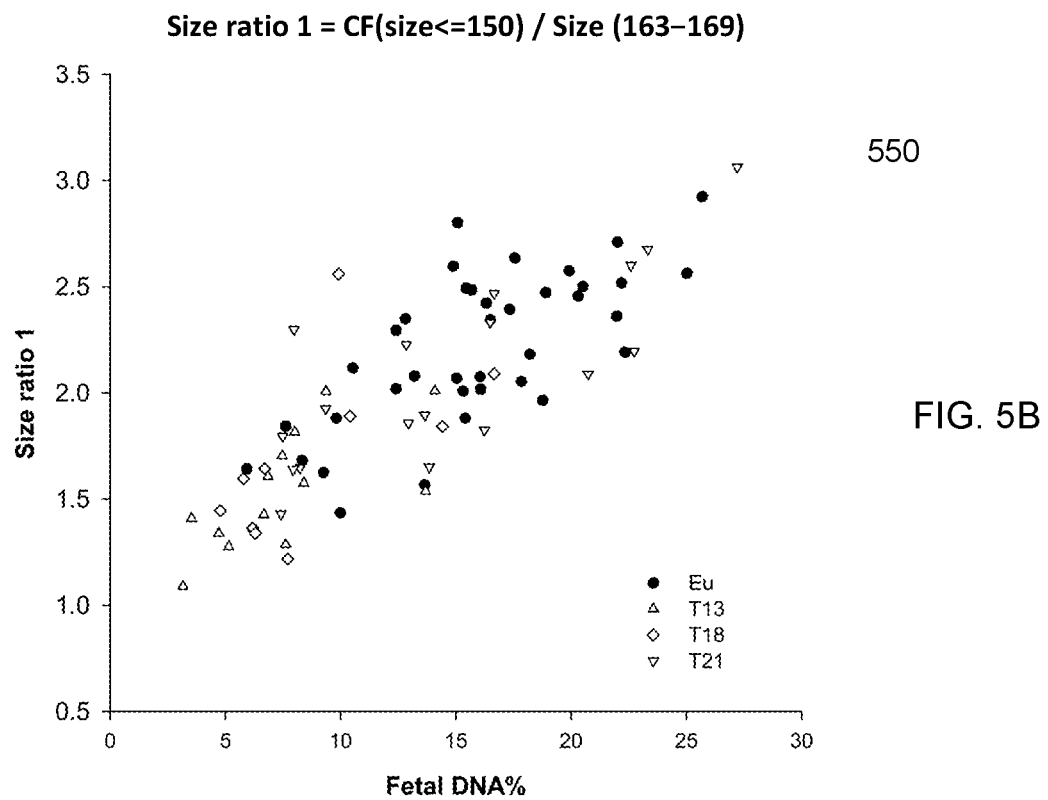
FIG. 5B is a plot 550 showing a size ratio of the amounts of DNA fragments of ≤150 bp and DNA from 163 bp to 169 bp, which labeled as (CF(size≤150)/size(163-169)).

FIG. 5B is a plot 550 showing a size ratio of the amounts of DNA fragments of ≤150 bp and DNA from 163 bp to 169 bp, which is labeled as (CF(size≤150)/size(163-169)). The CF(size≤150)/size(163-169) ratio is plotted against the fractional fetal DNA concentration for the 80 maternal plasma samples. There is a positive relationship between the fractional fetal DNA concentration and the CF(size≤150)/size (163-169) ratio for all samples (Pearson correlation coefficient=0.815). The positive correlation between the size parameter and the fractional fetal DNA concentration is consistent across samples with different fetal chromosomal ploidy status.

Figure 6A:
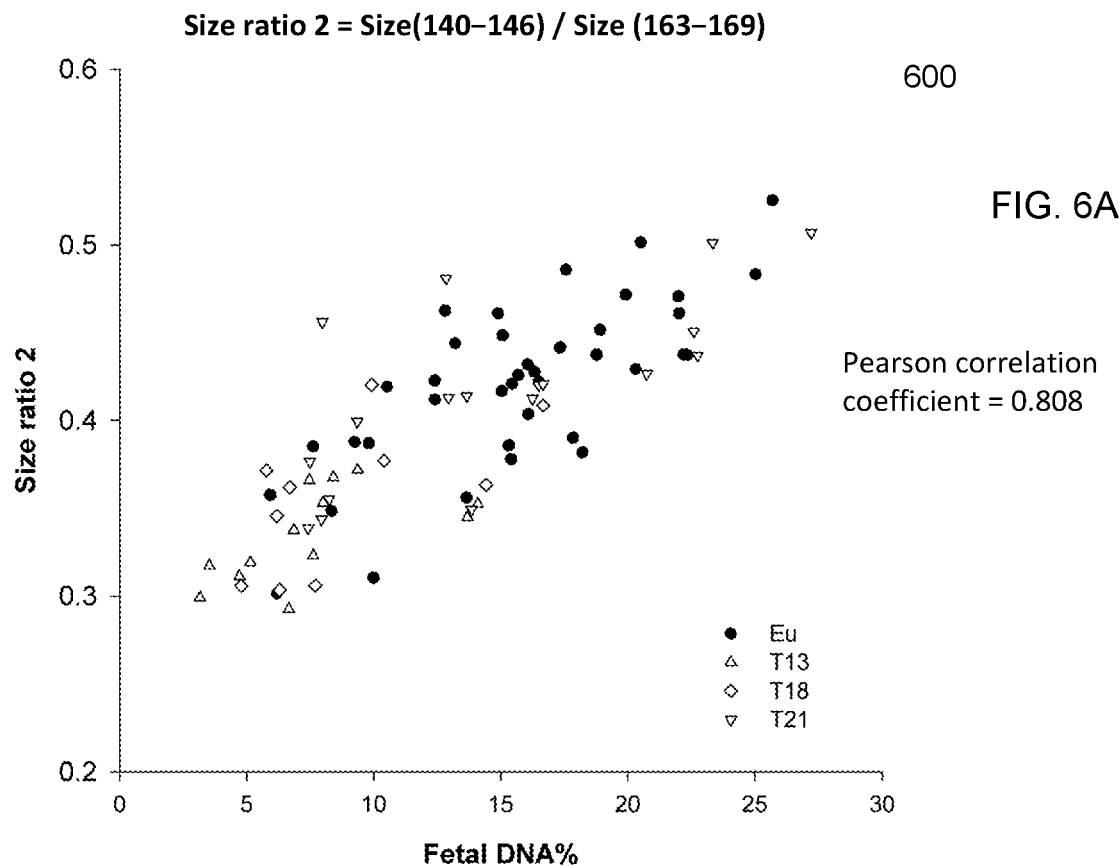
FIG. 6A is a plot 600 showing a size ratio of the amounts of DNA fragments from 140 bp to 146 bp and DNA from 163 bp to 169 bp, which is labeled as (size(140-146)/size(163-169)).

FIG. 6A is a plot 600 showing a size ratio of the amounts of DNA fragments from 140 bp to 146 bp and DNA from 163 bp to 169 bp, which is labeled as (size(140-146)/size (163-169)). The size(140-146)/size(163-169) ratio is plotted against the fractional fetal DNA concentration for the 80 maternal plasma samples. There is a positive relationship between the fractional fetal DNA concentration and the size(140-146)/size(163-169) ratio for all samples (Pearson correlation coefficient=0.808). The positive correlation between the size parameter and the fractional fetal DNA concentration is consistent across samples with different fetal chromosomal ploidy status.

Figure 6B:
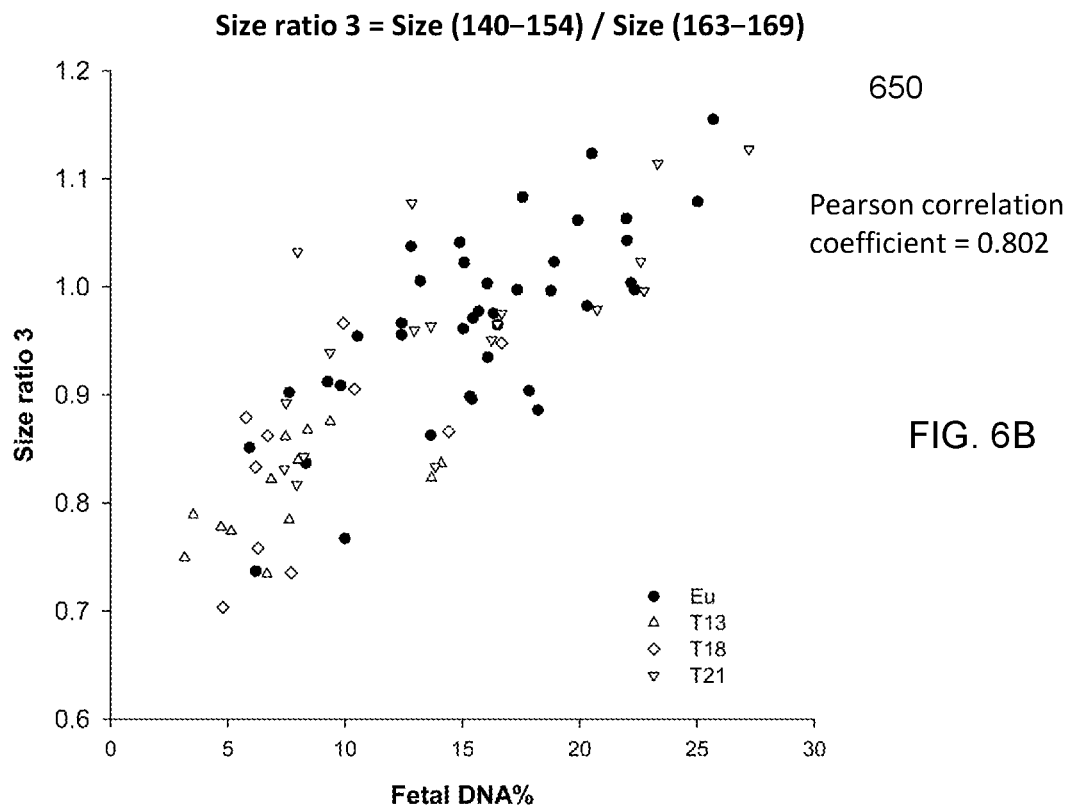
FIG. 6B is a plot 650 showing a size ratio of the amounts of DNA fragments from 140 bp to 154 bp and DNA from 163 bp to 169 bp, which is labeled as (size(140-154)/size(163-169)).

FIG. 6B is a plot 650 showing a size ratio of the amounts of DNA fragments from 140 bp to 154 bp and DNA from 163 bp to 169 bp, which is labeled as (size(140-154)/size (163-169)). The size(140-154)/size(163-169) ratio is plotted against the fractional fetal DNA concentration for the 80 maternal plasma samples. There is a positive relationship between the fractional fetal DNA concentration and the size(140-154)/size(163-169) ratio for all samples (Pearson correlation coefficient=0.802). The positive correlation between the size parameter and the fractional fetal DNA concentration appears to be consistent across samples with different fetal chromosomal ploidy status.

Figure 7:
FIG. 7 is a plot 700 showing a size ratio of the amounts of DNA fragments from 100 bp to 150 bp and DNA from 163 bp to 169 bp, which is labeled as (size(100-150)/size(163-169)).

FIG. 7 is a plot 700 showing a size ratio of the amounts of DNA fragments from 100 bp to 150 bp and DNA from 163 bp to 169 bp, which is labeled (size(100-150)/size(163-169)). The size(100-150)/size(163-169) ratio is plotted against the fractional fetal DNA concentration for the 80 maternal plasma samples. There is a positive relationship between the fractional fetal DNA concentration and the size(100-150)/size(163-169) ratio for all samples (Pearson correlation coefficient=0.831). The positive correlation between the size parameter and the fractional fetal DNA concentration is consistent across samples with different fetal chromosomal ploidy status.

B. Second Sample Set

Figure 8:
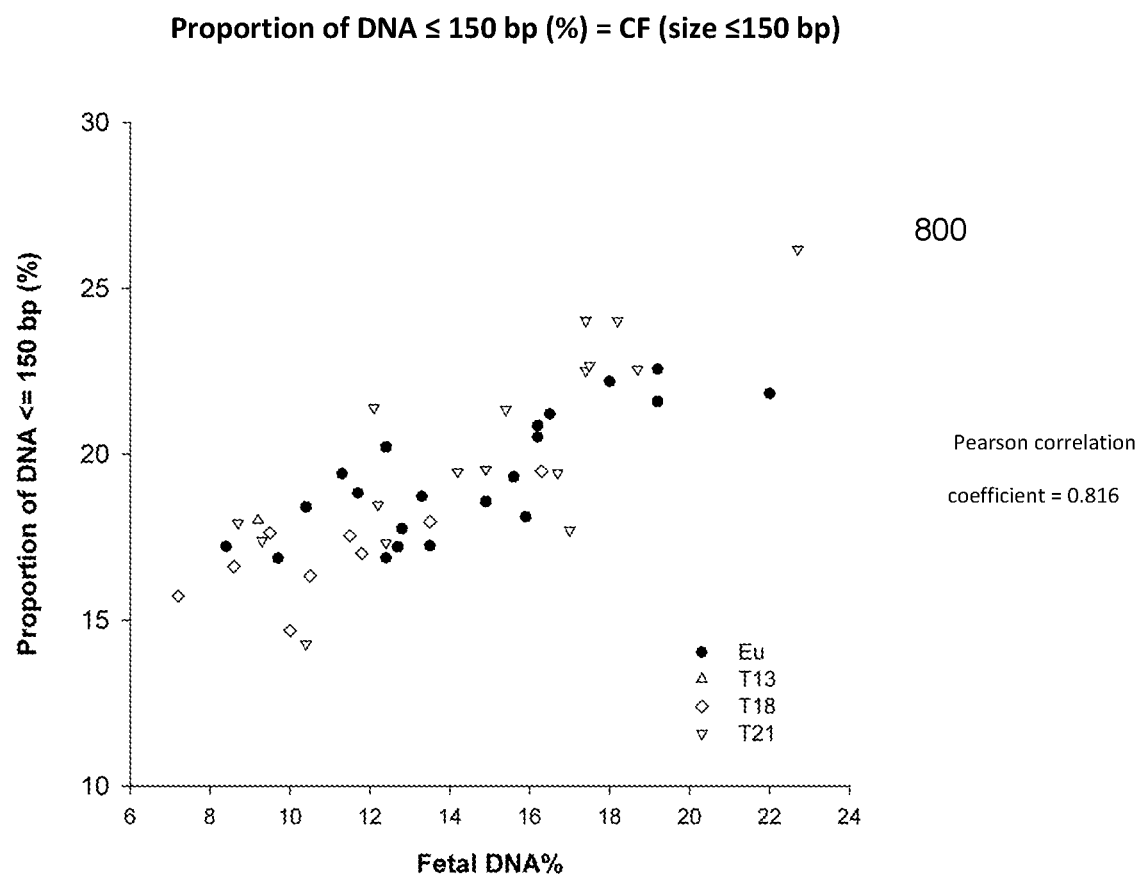
FIG. 8 is a plot 800 showing a proportion of DNA fragments of 150 bp or below for samples having various fetal DNA percentages in maternal plasma according to embodiments of the present invention.

FIG. 8 is a plot 800 showing a proportion of DNA fragments of 150 bp or below for samples having various fetal DNA percentage in maternal plasma according to embodiments of the present invention. The proportion of DNA ≤150 bp is plotted against the fractional fetal DNA concentration for the 48 maternal plasma samples which were massively parallel paired-end sequenced after target enrichment. The euploid samples are represented by filled circles. The trisomy 13 (T13) samples are represented by unfilled triangles. The trisomy 18 (T18) samples are represented by unfilled rhombus and the trisomy 21 (T21) samples are represented by inverted unfilled triangles. There is a positive relationship between the fractional fetal DNA concentration and the proportion of DNA ≤150 bp for all samples (Pearson correlation coefficient=0.816). The positive correlation between the size parameter and the fractional fetal DNA concentration is consistent across samples with different fetal chromosomal status. These results suggest that the analysis of the size parameter is useful for estimating the fractional fetal DNA concentration in a maternal plasma sample.

Figure 9A:
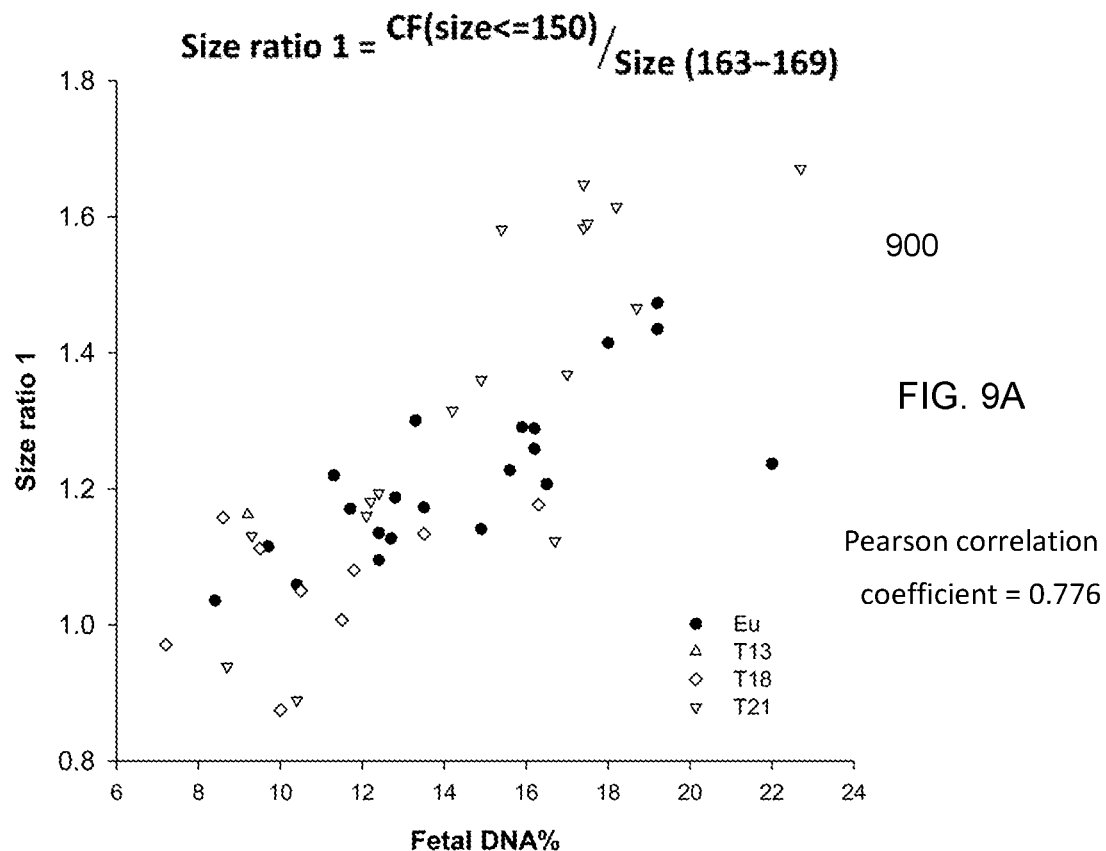
FIG. 9A is a plot 900 showing a size ratio of the amounts of DNA fragments of ≤150 bp and DNA from 163 bp to 169 bp, which is labeled as (CF(size≤150)/size(163-169)).

FIG. 9A is a plot 900 showing a size ratio of the amounts of DNA fragments of ≤150 bp and DNA from 163 bp to 169 bp, which is labeled as (CF(size≤150)/size(163-169)). The CF(size≤150)/size(163-169) ratio is plotted against the fractional fetal DNA concentration for the 48 maternal plasma samples. There is a positive relationship between the fractional fetal DNA concentration and the CF(size≤150)/size (163-169) ratio for all samples (Pearson correlation coefficient=0.776). The positive correlation between the size parameter and the fractional fetal DNA concentration is consistent across samples with different fetal chromosomal ploidy status.

Figure 9B:
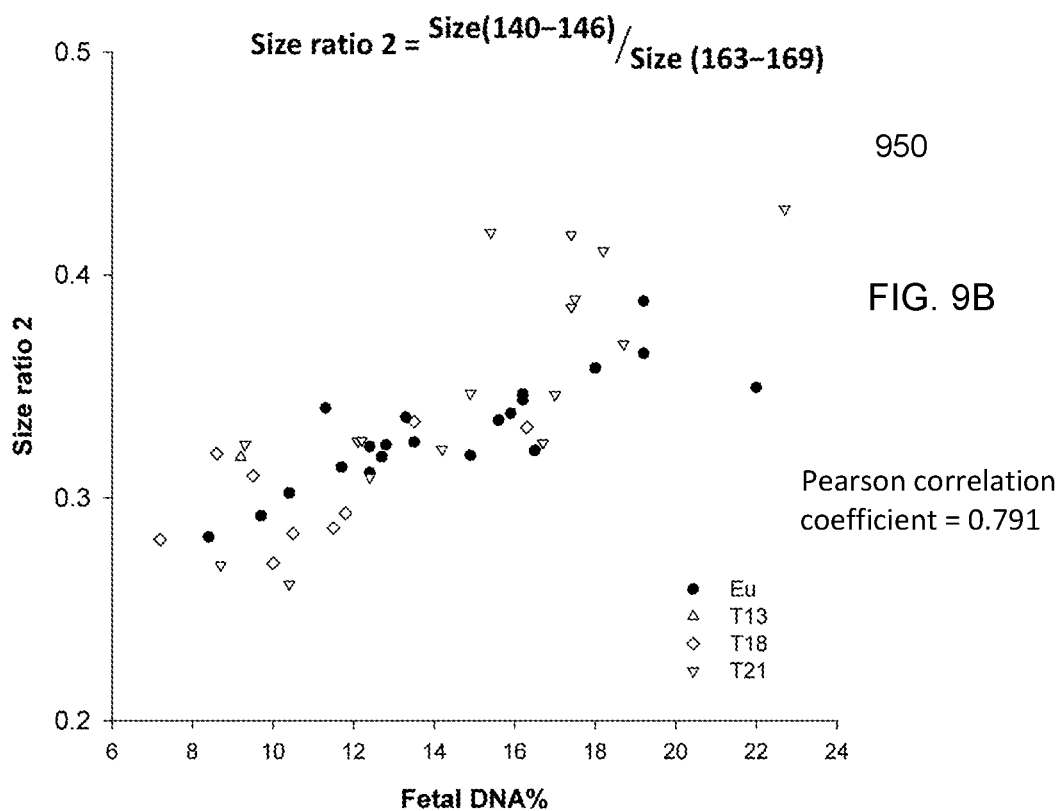
FIG. 9B is a plot 950 showing a size ratio of the amounts of DNA fragments from 140 bp to 146 bp and DNA from 163 bp to 169 bp, which is labeled as (size(140-146)/size(163-169)).

FIG. 9B is a plot 950 showing a size ratio of the amounts of DNA fragments from 140 bp to 146 bp and DNA from 163 bp to 169 bp, which is labeled as (size(140-146)/size (163-169)). The size(140-146)/size(163-169) ratio is plotted against the fractional fetal DNA concentration for the 48 maternal plasma samples. There is a positive relationship between the fractional fetal DNA concentration and the size(140-146)/size(163-169) ratio for all samples (Pearson correlation coefficient=0.790). The positive correlation between the size parameter and the fractional fetal DNA concentration is consistent across samples with different fetal chromosomal ploidy status.

Figure 10A:
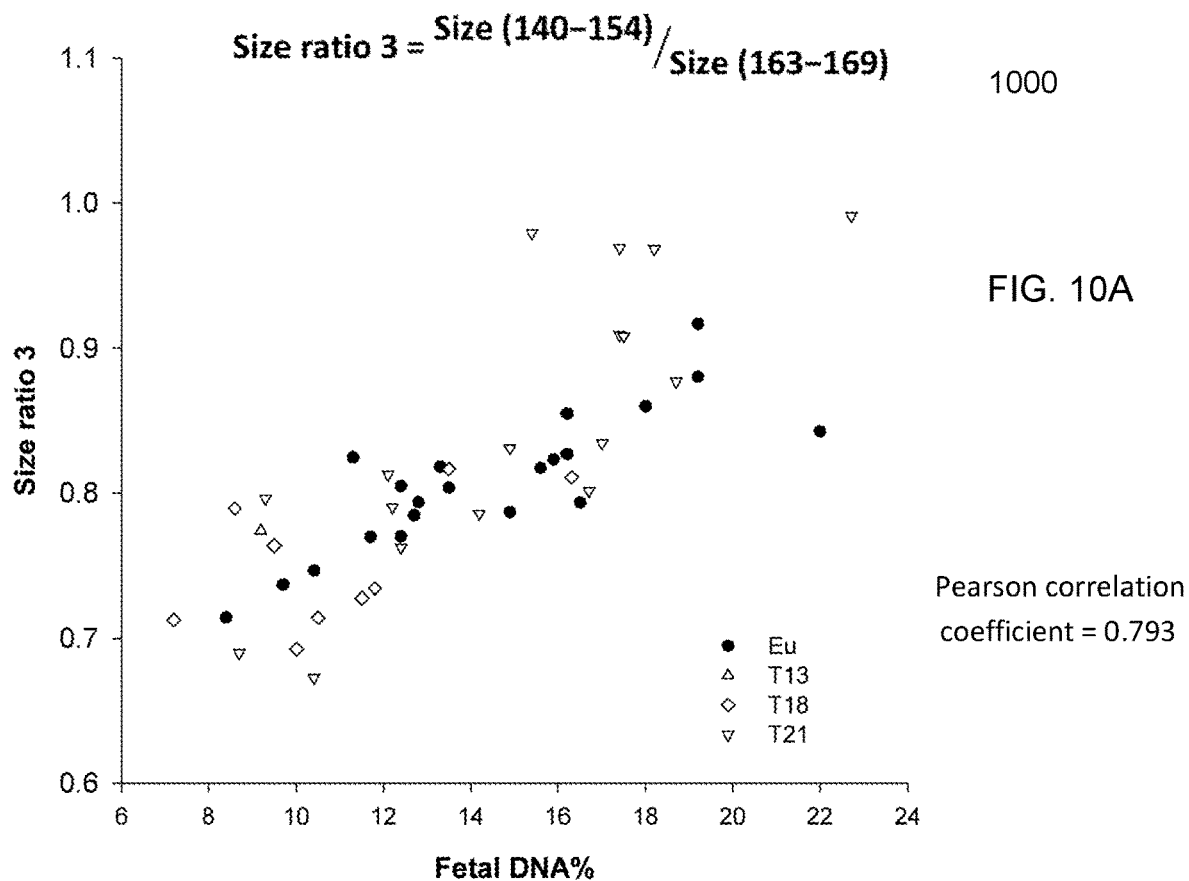
FIG. 10A is a plot 1000 showing a size ratio of the amounts of DNA fragments from 140 bp to 154 bp and DNA from 163 bp to 169 bp, which is labeled as (size(140-154)/size(163-169)).

FIG. 10A is a plot 1000 showing a size ratio of the amounts of DNA fragments from 140 bp to 154 bp and DNA from 163 bp to 169 bp, which is labeled as (size(140-154)/size(163-169)). The size(140-154)/size(163-169) ratio is plotted against the fractional fetal DNA concentration for the 48 maternal plasma samples. There is a positive relationship between the fractional fetal DNA concentration and the size(140-154)/size(163-169) ratio for all samples (Pearson correlation coefficient=0.793). The positive correlation between the size parameter and the fractional fetal DNA concentration is consistent across samples with different fetal chromosomal ploidy status.

Figure 10B:
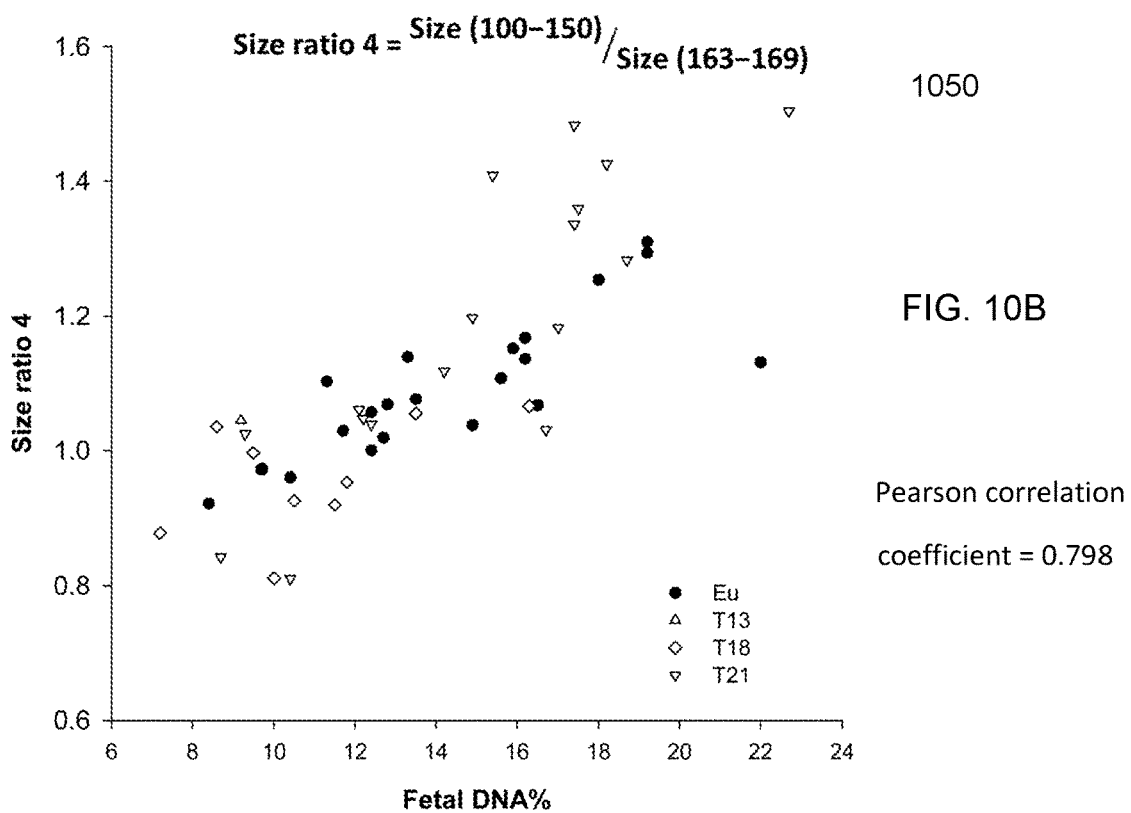
FIG. 10B is a plot 1005 showing a size ratio of the amounts of DNA fragments from 100 bp to 150 bp and DNA from 163 bp to 169 bp, which is labeled as (size(100-150)/size(163-169)).

FIG. 10B is a plot 1005 showing a size ratio of the amounts of DNA fragments from 100 bp to 150 bp and DNA from 163 bp to 169 bp, which is labeled as (size(100-150)/size(163-169)). The size(100-150)/size(163-169) ratio is plotted against the fractional fetal DNA concentration for the 48 maternal plasma samples. There is a positive relationship between the fractional fetal DNA concentration and the size(100-150)/size(163-169) ratio for all samples (Pearson correlation coefficient=0.798). The positive correlation between the size parameter and the fractional fetal DNA concentration is consistent across samples with different fetal chromosomal ploidy status C. Repeats Above, we have demonstrated that the size of all mappable DNA fragments in the maternal plasma is correlated with the fractional fetal DNA concentration. In this section, we investigate if the analysis of the size of the repeat elements in the genome can also be used for the estimation of fractional fetal DNA concentration in plasma. In the current example, we analyzed the size distribution of the DNA fragments mapping to the Alu repeats of the genome.

Figure 11:
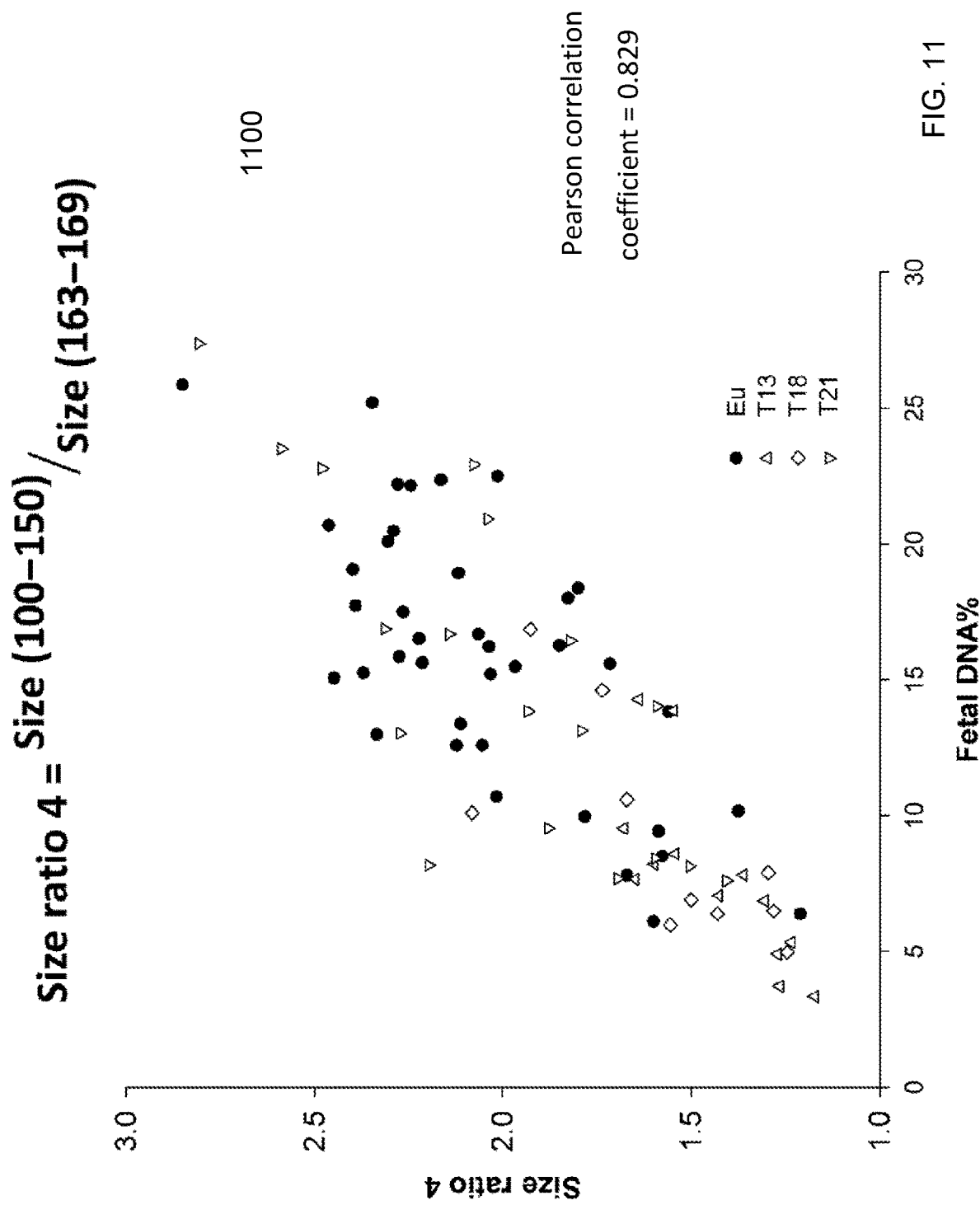
FIG. 11 is a plot showing a size ratio plotted vs. fetal DNA percentage for the size of repeat elements according to embodiments of the present invention.

FIG. 11 is a plot showing a size ratio plotted vs. fetal DNA percentage for the size of repeat elements according to embodiments of the present invention. This example uses the ratio of the amounts of DNA fragments from 100 bp to 150 bp and DNA from 163 bp to 169 bp (size(100-150)/size(163-169)) to reflect the alteration in the size distribution vs. fetal DNA percentage. There is a positive correlation between the size ratio and the fractional fetal DNA concentration (Pearson correlation coefficient=0.829). This result suggests that the size analysis of the repeat elements can also be used to determine the fractional fetal DNA concentration in a maternal sample.

In addition to using massively parallel sequencing, other methods, e.g. PCR, real-time PCR and mass spectrometry analysis can also be used to determine the size distribution of the repeat elements (e.g., Alu repeats) in maternal plasma. In one embodiment, the DNA in a maternal plasma sample can be ligated to a linker. Then, PCR can be performed using one primer specific to the Alu sequences and the other primer specific to the linker. Following PCR, the PCR products could be analyzed for their sizes, e.g. by electrophoresis, mass spectrometry, or massively parallel sequencing. This would allow a readout of the sizes of sequences derived from the Alu repeats in maternal plasma. This strategy can be used for other target sequence or sequence family. Furthermore, the PCR can be followed by a nested PCR involving another Alu-specific primer, in combination with either the same linker-specific primer or a nested primer within the linker. Such nested PCR would have the advantage of increasing the specificity of the amplification towards the sequence of interest (in this case being the Alu sequences).

One advantage of using repeat elements is that they have a relatively high copy number and so they may be easier to analyze. For example, one may be able to use fewer cycles of amplification. Also, with a higher copy number, the analytical precision is potentially higher. A potential disadvantage is that certain classes of repeat elements may have copy numbers that vary from individual to individual.

D. Electrophoresis

Figure 12A:
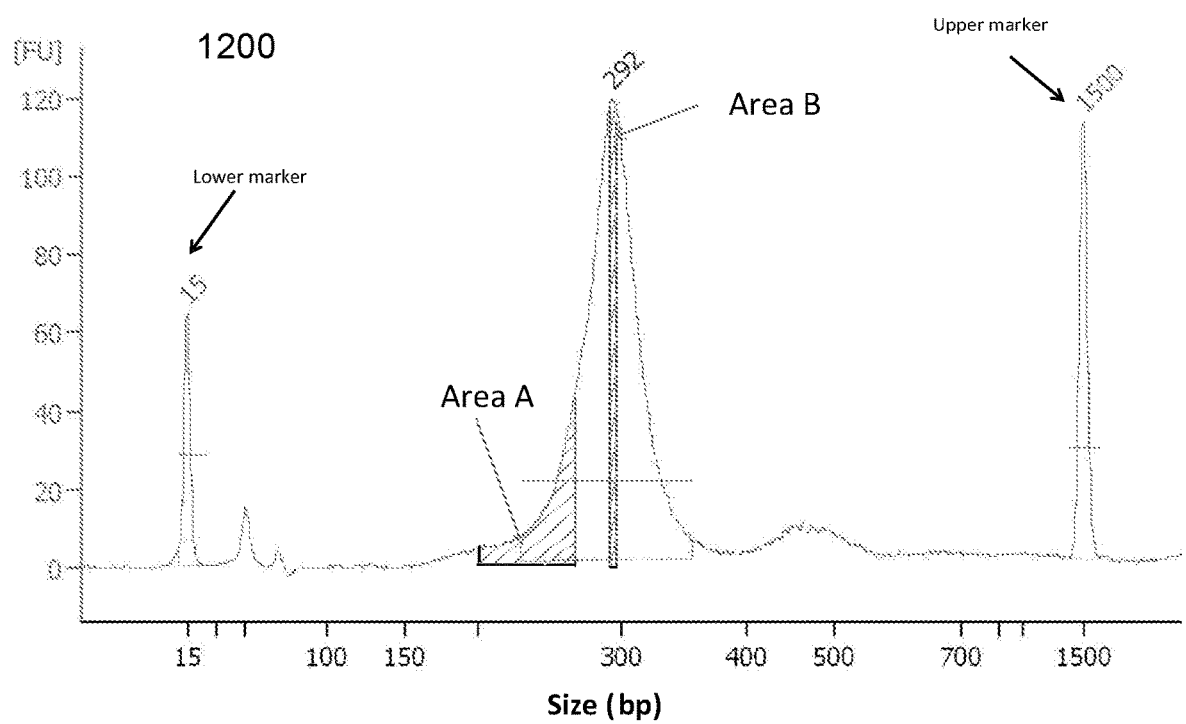
FIG. 12A is an electropherogram 1200 that may be used to determine a size ratio according to embodiments of the present invention.

FIG. 12A is an electropherogram 1200 that may be used to determine a size ratio according to embodiments of the present invention. For all of the analyzed DNA libraries, there was a sharp peak at approximately 292 bp, followed by a secondary peak ranging from 300 bp to 400 bp. As the area under curve for a size range can represent the relative amount of DNA fragments from that region, we used the ratio of the area of regions A (from 200 bp to 267 bp) and B (from 290 bp to 294 bp) to quantify the relative abundance of short and long DNA fragments. We first manually adjusted the baseline of fluorescence units (FU) to 0 and then generated the area for the selected region.

Figure 12B:
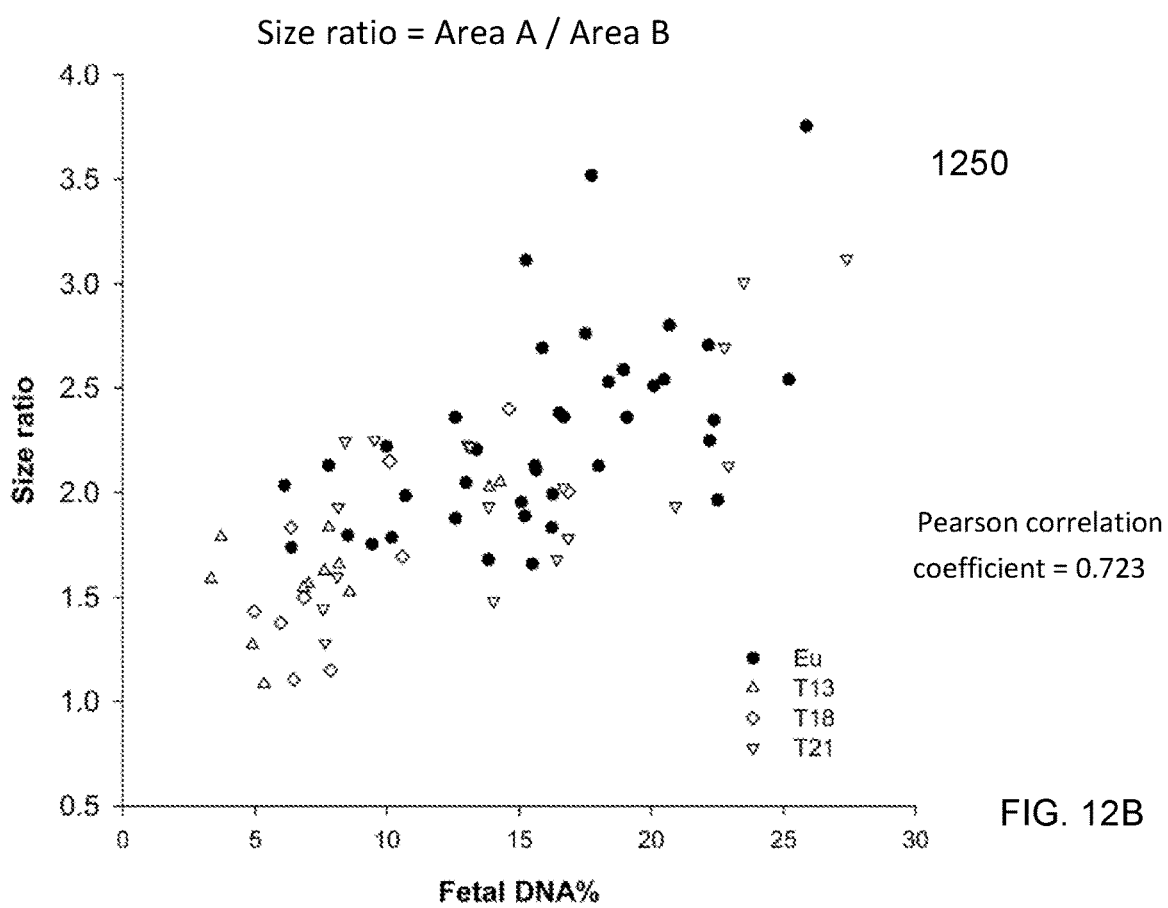
FIG. 12B is a plot 1250 showing a size ratio of the amounts of DNA fragments from 200 bp to 267 bp and DNA from 290 bp to 294 bp for samples having various fetal DNA percentage in maternal plasma according to embodiments of the present invention.

FIG. 12B is a plot 1250 showing a size ratio of the amounts of DNA fragments from 200 bp to 267 bp and DNA from 290 bp to 294 bp (i.e., the ratio of the areas of region A and B shown on the electropherogram) for samples having various fetal DNA percentages in maternal plasma according to embodiments of the present invention. There was one T13 case showing a low 292-bp peak with the FU value of 6.1, whereas all other cases showed a FU value ≥20 FUs. As the low FU value would make the area measurement imprecise, this case was ignored from the analysis. The ratio of the areas of region A and B is plotted against the fractional fetal DNA concentration for the all other 79 maternal plasma samples. There is a positive relationship between the fractional fetal DNA concentration and the area A and B ratio for these samples (Pearson correlation coefficient=0.723).

VI. Determining Calibration Data Points

As mentioned above, the calibration data points may be defined in a variety of ways. Additionally, the calibration data points may be obtained in a variety of ways. For example, the calibration data points may simply be read from memory as a series of calibration values of a parameter along with the corresponding fractional concentration. Also, a calibration function can be read from memory (e.g., a linear or non-linear function with a predetermined functional form), where the function defines the calibration data points. In some embodiments, the calibration data points can be calculated from data measured from calibration samples.

A. Method

Figure 13:
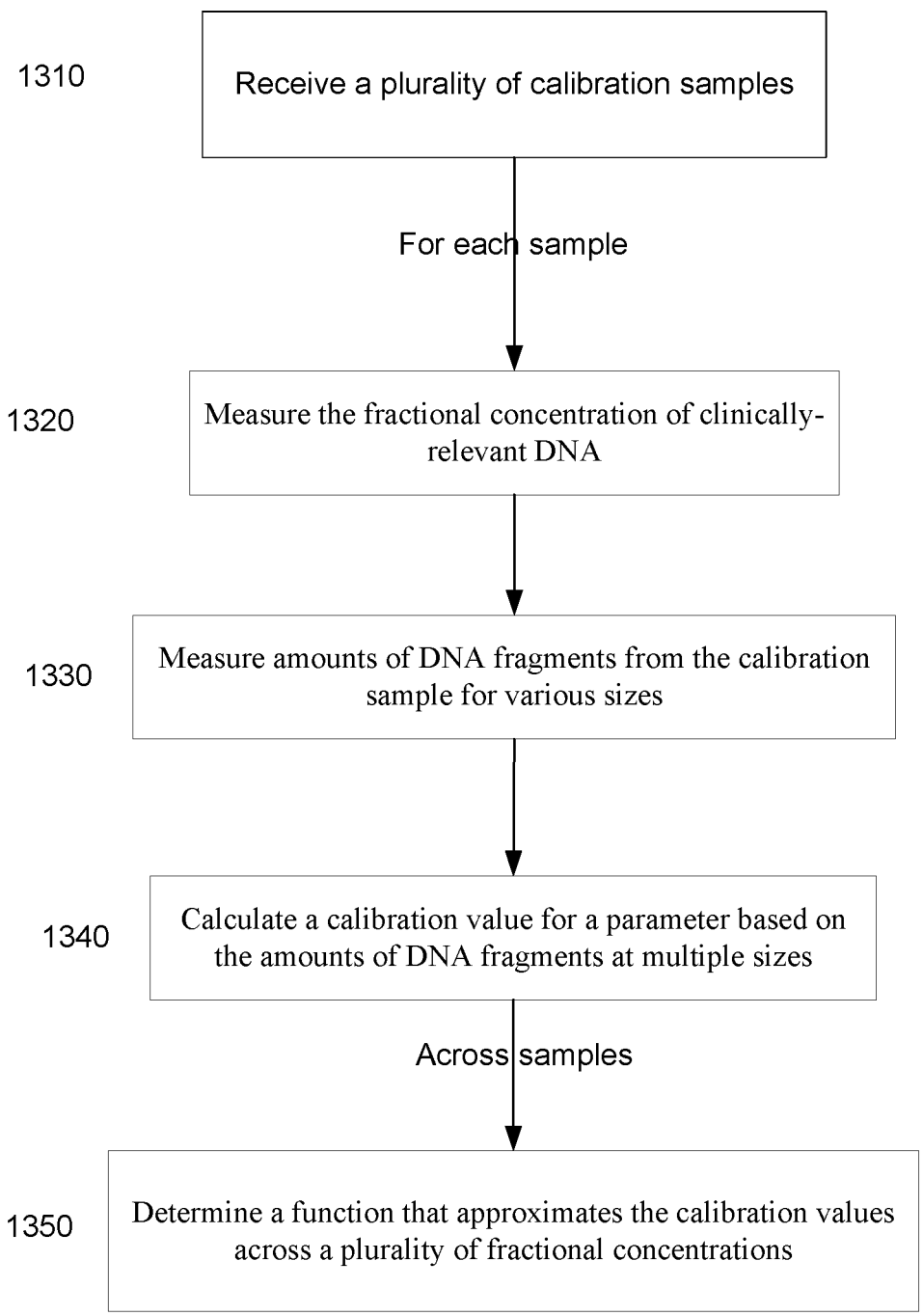
FIG. 13 is a flowchart of a method 1300 for determining calibration data points from measurements made from calibration samples according to embodiments of the present invention.

FIG. 13 is a flowchart of a method 1300 for determining calibration data points from measurements made from calibration samples according to embodiments of the present invention. The calibration samples include the clinically-relevant DNA and other DNA.

At block 1310, a plurality of calibration samples are received. The calibration samples may be obtained as described herein. Each sample can be analyzed separately via separate experiments or via some identification means (e.g., tagging a DNA fragment with a bar code) to identify which sample a molecule was from. For example, a calibration sample may be received at a machine, e.g., a sequencing machine, which outputs measurement data (e.g., sequence reads) that can be used to determine sizes of the DNA fragments, or is received at an electrophoresis machine.

At block 1320, the fractional concentration of clinically-relevant DNA is measured in each of the plurality of calibration samples. In various embodiments measuring a fetal DNA concentration, a paternally-inherited sequence or a fetal-specific epigenetic markers may be used. For example, a paternally-inherited allele would be absent from a genome of the pregnant female and can be detected in maternal plasma at a percentage that is proportional to the fractional fetal DNA concentration. Fetal-specific epigenetic markers can include DNA sequences that exhibit fetal or placental-specific DNA methylation patterns in maternal plasma.

At block 1330, amounts of DNA fragments from each calibration sample are measured for various sizes. The sizes may be measured as described herein. The sizes may be counted, plotted, used to create a histogram, or other sorting procedure to obtain data regarding a size profile of the calibration sample.

At block 1340, a calibration value is calculated for a parameter based on the amounts of DNA fragments at multiple sizes. A calibration value can be calculated for each calibration sample. In one embodiment, the same parameter is used for each calibration value. However, embodiments may use multiple parameters as described herein. For example, the cumulative fraction of DNA fragments less than 150 bases may be used as the parameter, and samples with different fractional concentration would likely have different calibration values. A calibration data point may be determined for each sample, where the calibration data point includes the calibration value and the measured fractional concentration for the sample. These calibration data points can be used in method 300, or can be used to determine the final calibration data points (e.g., as defined via a functional fit).

At block 1350, a function that approximates the calibration values across a plurality of fractional concentrations is determined. For example, a linear function could be fit to the calibration values as a function of fractional concentration. The linear function can define the calibration data points to be used in method 300.

In some embodiments, calibration values for multiple parameters can be calculated for each sample. The calibration values for a sample can define a multidimensional coordinate (where each dimension is for each parameter) that along with the fractional concentration can provide a data point. Thus, in one implementation, a multidimensional function can be fit to all of the multidimensional data points. Accordingly, a multidimensional calibration curve can be used, where the different values of the parameters can effectively be input to a single calibration function that outputs the fractional concentration. And, the single calibration function can result from a functional fit of all of the data points obtained from the calibration samples.

B. Measuring Tumoral DNA concentration

As mentioned, embodiments can also be applied to concentration of tumor DNA in a biological sample. An example involving determining the fractional concentration of tumoral DNA follows.

We collected the plasma samples from two patients suffering from hepatocellular carcinoma (HCC) before and after surgical resection of the tumors. The size analysis was performed using paired-end (PE) massively parallel sequencing. Sequencing libraries of maternal plasma DNA were constructed as previously described (Lo Y M et al. *Sci Transl Med* 2010; 2:61ra91). All libraries were sequenced by a HiSeq 2000 (Illumina) using the 50-bp×2 PE format. The 50-bp sequence reads were aligned to the non-repeat-masked human reference genome (Hg18) (http://genome.ucsc.edu), using the Short Oligonucleotide Alignment Program 2 (SOAP2) (soap.genomics.org.cn). The size of each sequenced fragments was inferred from the coordinates of the outermost nucleotides at each end of the aligned fragments.

We genotyped the DNA extracted from the blood cells and the tumor sample of the HCC patients using the Affymetrix SNP6.0 microarray system. For each case, the regions demonstrating loss of heterozygosity (LOH) in the tumor tissue were identified using the Affymetrix Genotyping Console v4.0 based on the intensities of the different alleles of the SNP loci. The fractional concentrations of tumor-derived DNA (F) were estimated from the difference in amounts of sequences carrying the deleted and non-deleted alleles at the LOH regions using the following formula: F=(A−B)/A×100%, where A is the number of sequence reads carrying the non-deleted alleles at the heterozygous SNPs in the LOH regions, and B is the number of sequence reads carrying the deleted alleles for the heterozygous SNPs in the LOH regions. Table 3 shows the results.

| Case No. | Sampling time | No. of sequenced reads | Fractional concentration of tumor DNA in plasma (%) |
|---|---|---|---|
| 1 | before tumor resection | 448M | 51.60 |
|   | after tumor resection | 486M | 0.90 |
| 2 | before tumor resection | 479M | 5.60 |
|   | after tumor resection | 542M | 0.90 |

Table 3 shows sequencing information and measured fractional concentration of tumor DNA in the plasma samples.

In another embodiment, a locus that exhibits duplication can be used. For example, a tumor can exhibit a gain of one copy of one of the two homologous chromosomes such that an allele is duplicated. Then, one can determine a first amount A of sequence reads having a non-duplicated allele at the one or more heterozygous loci (e.g., SNPs) and a second amount B of sequence reads having a duplicated allele at the heterozygous loci. The fractional concentration F of clinically-relevant DNA can be calculated as a ratio of the first amount and the second amount using a ratio (B−A)/A.

In another embodiment, one or more homozygous loci may be used. For example, one can identify one or more loci where the patient is homozygous and where a single nucleotide mutation is present in the tumor tissue. Then, a first amount A of sequence reads having a wildtype allele at the one or more homozygous loci can be determined. And, a second amount B of sequence reads having a mutant allele at one or more homozygous loci can be determined. The fractional concentration F of clinically-relevant DNA can be calculated as a ratio of the first amount and the second amount using a ratio 2B/(A+B).

C. Example of Functional Fit to Data Points

An example of performing a functional fit to the parameter values determined from calibration samples is now described. Plasma samples from 80 pregnant women each carrying a singleton male fetus were analyzed. Among these 80 pregnant women, 39 were carrying euploid fetuses, 13 were carrying trisomy 13 (T13) fetuses, 10 were carrying trisomy 18 (T18 fetuses) and 18 were carrying trisomy 21 (T21) fetuses. The median gestational age of the pregnant women was 13 weeks and 1 day. DNA was extracted from the plasma samples and sequenced using the Illumina HiSeq2000 platform as described (Zheng Y W et al. *Clin Chem.* 2012; 58:549-58.) except that the sequencing was performed in an 8-plex format. For each DNA molecule, 50 nucleotides were sequenced from each of the two ends and aligned to a reference genome (hg18).

The size of each sequenced molecule was then deduced from the coordinates of the outermost nucleotides at both ends. For each sample, a median of 11.1 million fragments were sequenced and aligned uniquely to the reference genome. A ratio was calculated by dividing the proportion of DNA molecules with size 100 bp to 150 bp by the proportion of DNA molecules with size 163 bp to 169 bp and this ratio is termed the size ratio. As all the 80 pregnancies were carrying a male fetus, the proportion of sequence reads that were uniquely aligned to the chromosome Y was used to determine the fractional concentration of fetal DNA in each plasma DNA sample.

The samples were randomly divided into two sets, namely the training set and validation set. The relationship between the fractional fetal DNA concentration and the size ratio was established based the samples in the training set using linear regression. Then, the size ratio was used to deduce the fractional fetal DNA concentration for the validation set using the linear regression formula. The validation is discussed in the next section.

Figure 14A:
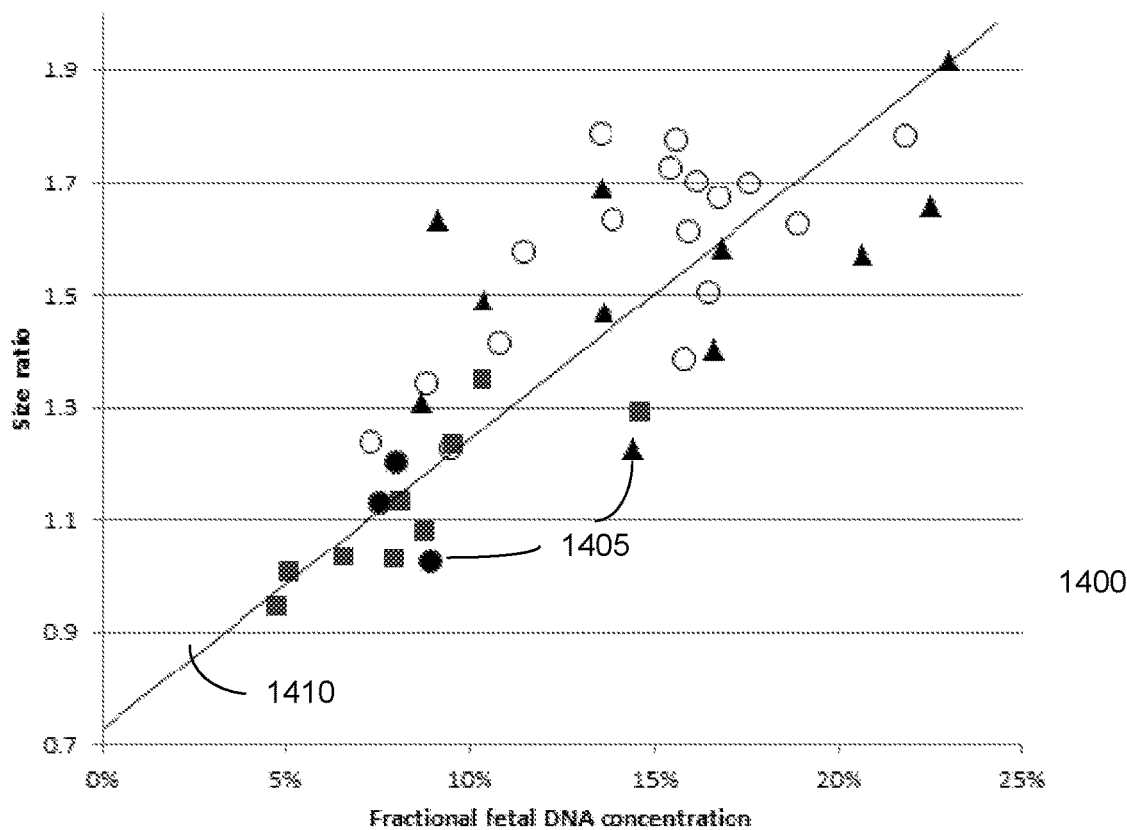
FIG. 14A is a plot 1400 of a size ratio against the fractional concentration of fetal DNA for the training set according to embodiments of the present invention.

FIG. 14A is a plot 1400 of a size ratio against the fractional concentration of fetal DNA for the training set according to embodiments of the present invention. As mentioned above, the size ratio is calculated by dividing the proportion of DNA molecules with size 100 bp to 150 bp by the proportion of DNA molecules with size 163 bp to 169 bp. The size ratio is plotted against the fractional concentration of fetal DNA, as shown by data points 1405. The unfilled circles represent the euploid cases. The filled symbols represent the aneuploidy cases (square for T13, circle for T18 and triangle for T21). The linear regression line 1410 results from the functional fit to the data points. The functional fit can be performed via any suitable techniques, e.g., least squares. The line 1410 can be used to estimate values of parameters measured for other samples, not in the training set. Each part of line 1410 can be considered a calibration data point.

VII. Comparison to Calibration Data Points

As mentioned above, the calibration data points can be used to determine the fractional concentration of the clinically relevant DNA. For example, the raw data points 1405 in FIG. 14A may be used to provide a range of fractional DNA concentration for a particular calibration value (labeled size ratio in FIG. 14A), where the range can be used to determine if the fractional concentration is above a threshold amount. Instead of a range, an average of the fractional concentrations at a particular size ratio can be used. For example, the fractional concentration corresponding to a measurement of 1.3 as the size ratio in a new sample can be determined as the average concentration calculated from the two data points at 1.3. In one embodiment, a functional fit (e.g., line 1410) may be used.

Figure 14B:
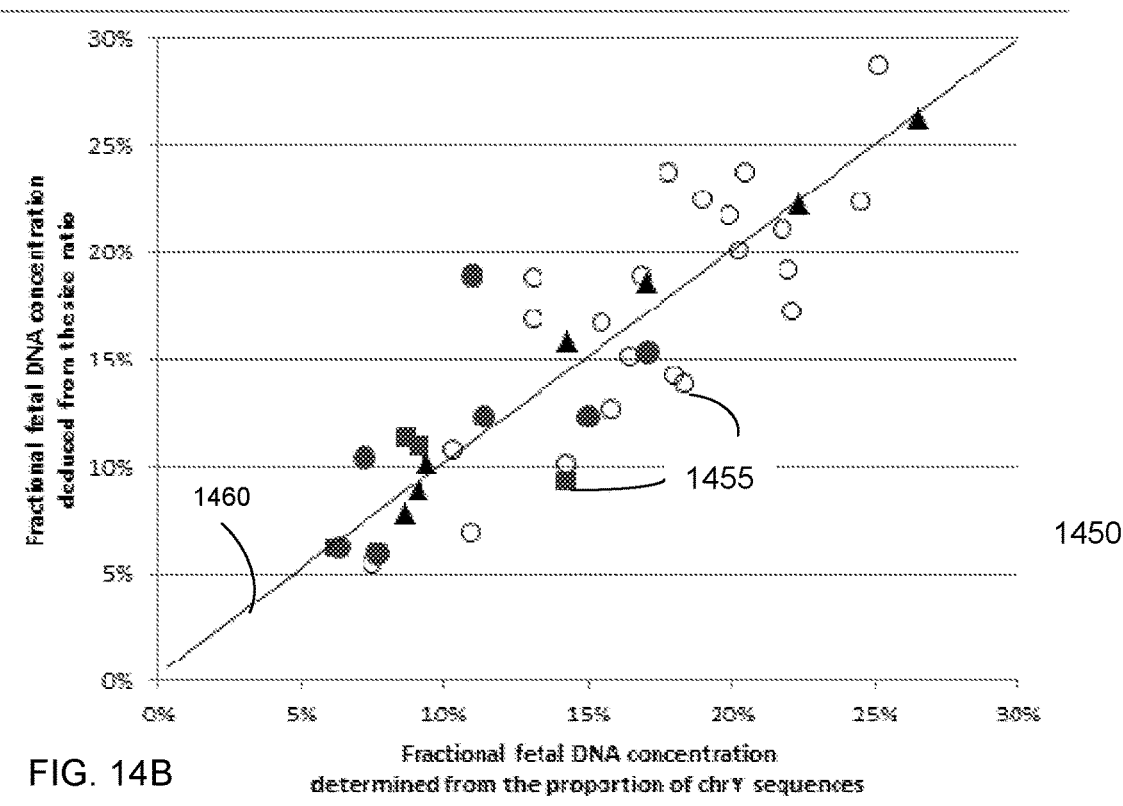
FIG. 14B is a plot 1450 of fractional concentrations deduced (estimated) from linear function 1410 of FIG. 14A against the fractional concentrations measured using fetal-specific sequences according to embodiments of the present invention.

FIG. 14B is a plot 1450 of fractional concentrations deduced (estimated) from linear function 1410 of FIG. 14A against the fractional concentrations measured using fetal-specific sequences according to embodiments of the present invention. Using the regression equation (i.e., line 1410) determined based on the data of the training set, the size ratio determined for a validation sample was used to deduce the fractional concentration of fetal DNA for the samples of the validation set. The measured fractional concentrations correspond to the proportion of chromosome Y sequences in the plasma DNA sample (i.e., proportion of sequence reads aligning to the chromosome Y).

The line 1460 represents the perfect correlation between the two sets of values. The deviation of a data point 1455 indicates how accurate the estimate was, with points on line 1460 being perfectly accurate. As noted herein, the estimate does not have to be perfectly accurate, as the desired test may simply be to determine whether a sufficient percentage of clinically-relevant DNA is in the biological sample. The unfilled circles represent the euploid cases. The filled symbols represent the aneuploidy cases (square for T13, circle for T18 and triangle for T21). The median difference between the fractional fetal DNA concentration deduced from the size ratio and that measured from the proportion of chromosome Y sequences was 2.1%. The difference was less than 4.9% in 90% of the samples.

Samples with different ploidy status were used in both the calibration set and the validation set. As shown in FIG. 14A, the relationship between the size ratio and the fractional fetal DNA concentration were consistent across samples with different ploidy status. As a result, the fractional fetal DNA concentration can be deduced from the size ratio of the sample without a prior knowledge of the ploidy status of the sample as illustrated in FIG. 14B. One calibration curve was used for samples with different ploidy status and, hence, we do not need to know the ploidy status of the sample before using embodiments to determine the fractional fetal DNA concentration.

VIII. Cancer

As described herein, embodiments can be used to estimate the fractional concentration of tumor DNA in a biological sample. As with the fetal examples, calibration samples can be used to determine correlation data points, e.g., by fitting a function (e.g., a linear function) to data points showing a correlation between a value of a size parameter and a measured fractional concentration.

A. Correlation of Size to Tumoral DNA Concentration

Figure 15A:
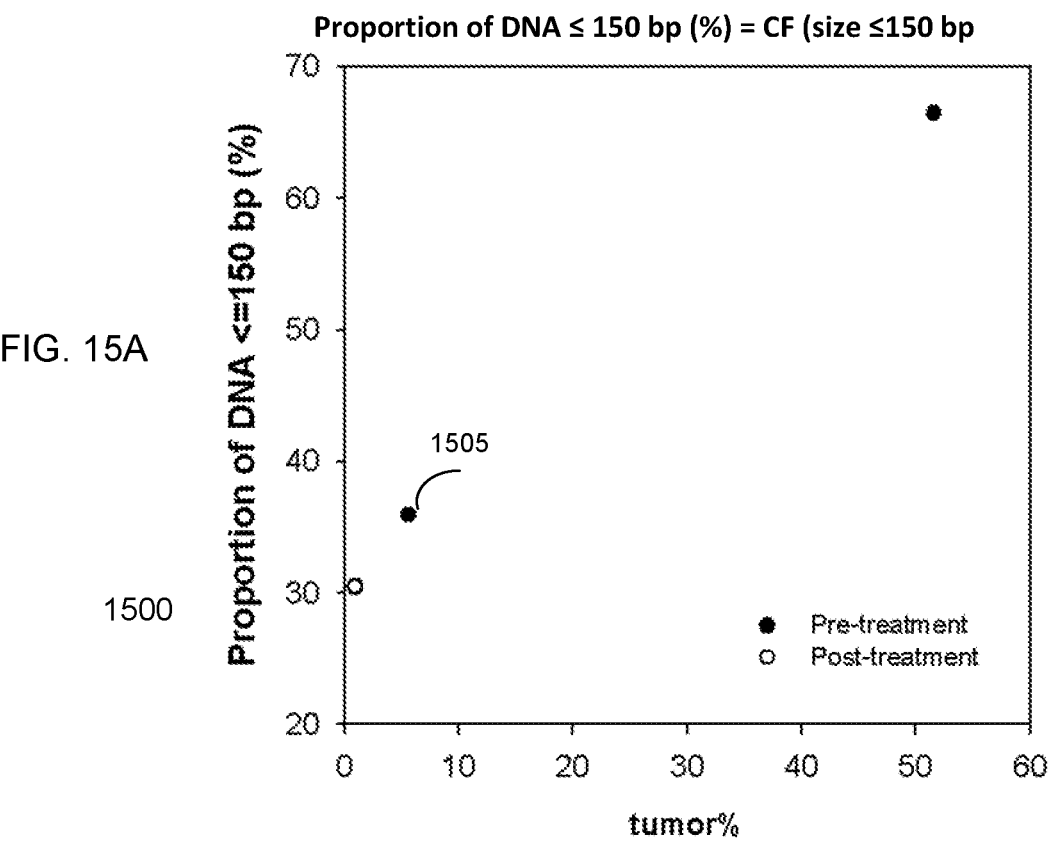
FIG. 15A is a plot 1500 showing a proportion of DNA fragments of 150 bp or below for samples having various tumor DNA percentages in plasma of two hepatocellular carcinoma (HCC) patients before and after tumor resection according to embodiments of the present invention.

FIG. 15A is a plot 1500 showing a proportion of DNA fragments of 150 bp or below for samples having various tumor DNA percentages in plasma of two HCC patients before and after tumor resection according to embodiments of the present invention. The proportion of DNA ≤150 bp is plotted against the fractional tumoral DNA concentrations for the two HCC patients before (filled circles) and after (unfilled circles) tumor resection. The two unfilled circles are very close in location to one another (effectively on top of each other). These results suggest that the analysis of the size parameter is useful for estimating the fractional tumoral DNA concentration in the plasma sample of HCC patents. There is a reduction in both the fractional tumor DNA concentration and the proportion of DNA fragments of ≤150 bp after tumor resection. The filled circle 1505 corresponds to a sample with much lower tumor DNA percentage, which is related to a smaller size of the tumor. In other words, the patient with a larger tumor has a higher proportion of short DNA which is reflected by a higher ratio of CF (≤150 bp) compared with the patient with a smaller tumor.

Figure 15B:
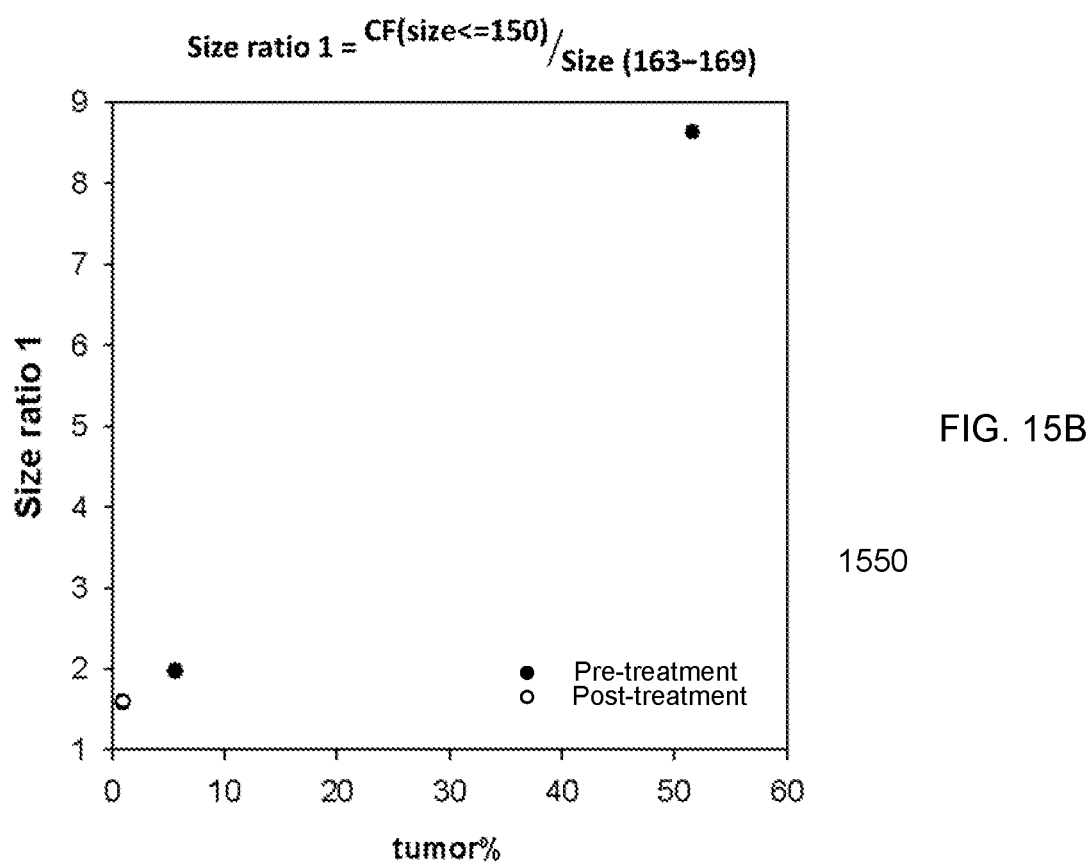
FIG. 15B is a plot 1550 showing a size ratio of the amounts of DNA fragments of ≤150 bp and DNA from 163 bp to 169 bp, which is labeled as (CF(size≤150)/size(163-169)), for two HCC patients before and after tumor resection.

FIG. 15B is a plot 1550 showing a size ratio of the amounts of DNA fragments of ≤150 bp and DNA from 163 bp to 169 bp, which is labeled as (CF(size≤150)/size(163-169)), for two HCC patients before and after tumor resection. The CF(size≤150)/size(163-169) ratio is plotted against the fractional tumoral DNA concentrations for the two HCC patients before (filled circles) and after (unfilled circles) tumor resection. The two unfilled circles are very close in location to one another. There is a reduction in both the fractional tumor DNA concentration and the size ratio after tumor resection.

Figure 16A:
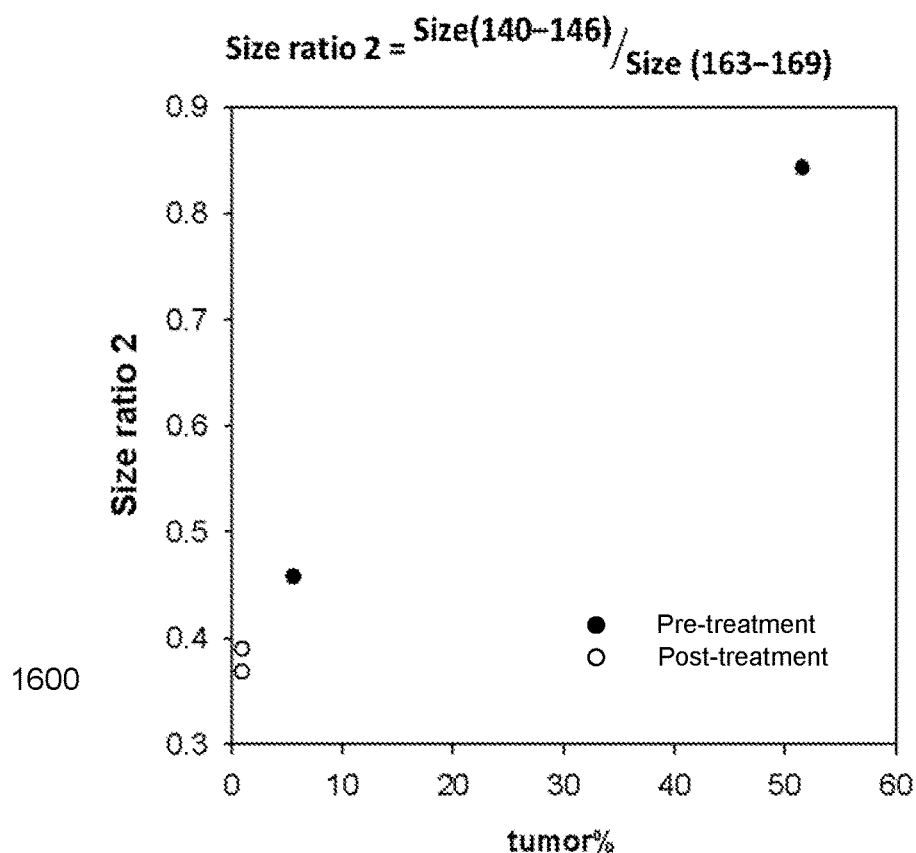
FIG. 16A is a plot 1600 showing a size ratio of the amounts of DNA fragments from 140 bp to 146 bp and DNA from 163 bp to 169 bp, which is labeled (size(140-146)/size (163-169)), for two HCC patients before and after tumor resection.

FIG. 16A is a plot 1600 showing a size ratio of the amounts of DNA fragments from 140 bp to 146 bp and DNA from 163 bp to 169 bp, which is labeled (size(140-146)/size(163-169)), for two HCC patients before and after tumor resection. The size(140-146)/size(163-169) ratio is plotted against the fractional tumoral DNA concentrations for the two HCC patients before (filled circles) and after (unfilled circles) tumor resection. There is a reduction in both the fractional tumor DNA concentration and the size ratio after tumor resection.

Figure 16B:
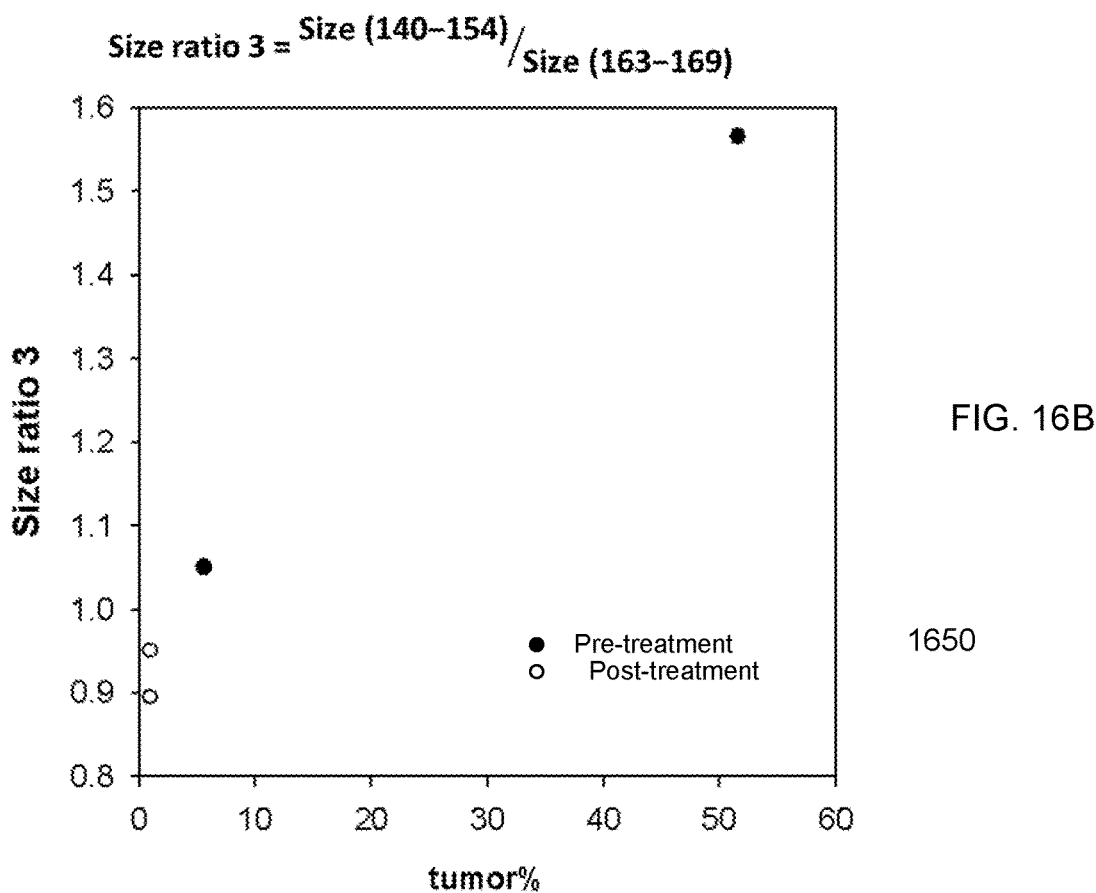
FIG. 16B is a plot 1650 showing a size ratio of the amounts of DNA fragments from 140 bp to 154 bp and DNA from 163 bp to 169 bp, which is labeled as (size(140-154)/size(163-169)), for two HCC patients before and after tumor resection.

FIG. 16B is a plot 1650 showing a size ratio of the amounts of DNA fragments from 140 bp to 154 bp and DNA from 163 bp to 169 bp, which is labeled as (size(140-154)/size(163-169)), for two HCC patients before and after tumor resection. The size(140-154)/size(163-169) ratio is plotted against the fractional tumoral DNA concentrations for the two HCC patients before (filled circles) and after (unfilled circles) tumor resection. There is a reduction in both the fractional tumor DNA concentration and the size ratio after tumor resection.

Figure 17:
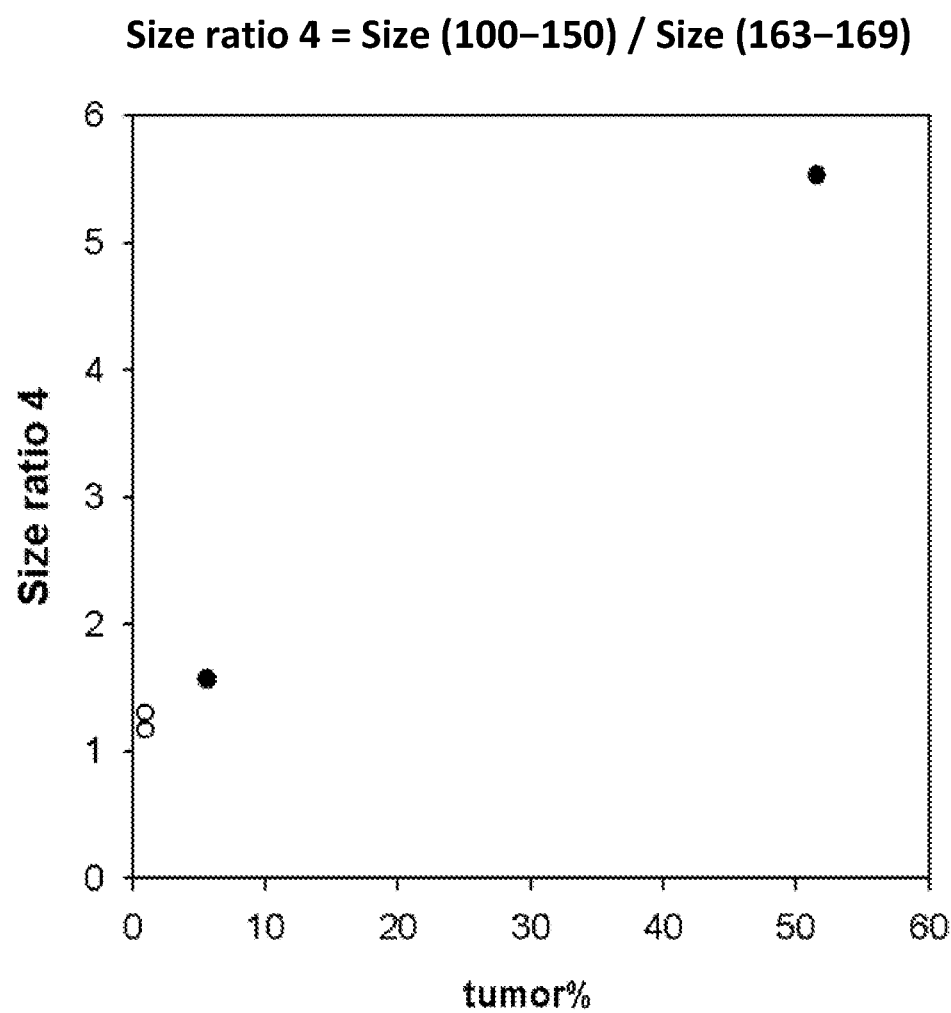
FIG. 17 is a plot 1700 showing a size ratio of the amounts of DNA fragments from 100 bp to 150 bp and DNA from 163 bp to 169 bp, which is labeled as (size(100-150)/size (163-169)), for two HCC patients before and after tumor resection.

FIG. 17 is a plot 1700 showing a size ratio of the amounts of DNA fragments from 100 bp to 150 bp and DNA from 163 bp to 169 bp, which is labeled as (size(100-150)/size(163-169)), for two HCC patients before and after tumor resection. The size(100-150)/size(163-169) ratio is plotted against the fractional tumoral DNA concentrations for the two HCC patients before (filled circles) and after (unfilled circles) tumor resection. There is a reduction in both the fractional tumor DNA concentration and the size ratio after tumor resection.

B. Size Decrease Due to Treatment

Figure 18A:
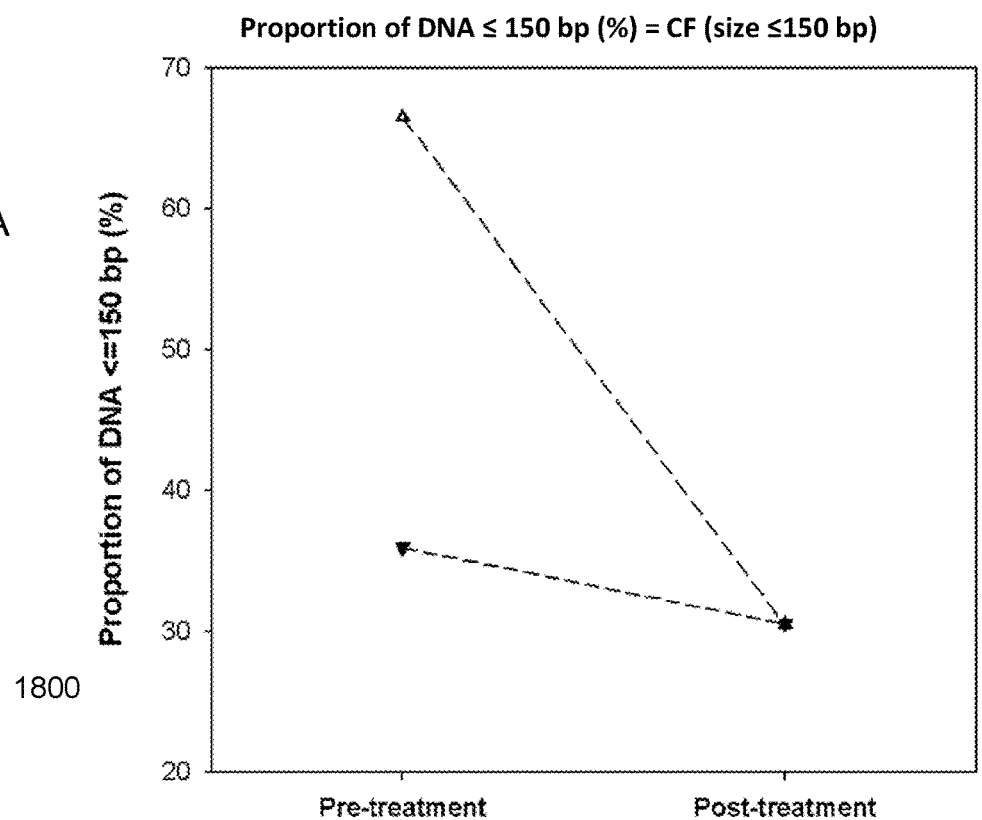
FIG. 18A is a plot 1800 showing a proportion of DNA fragments of 150 bp or below for HCC patients before and after tumor resection.

FIG. 18A is a plot 1800 showing a proportion of DNA fragments of 150 bp or below for HCC patients before and after tumor resection. The pair of samples from the same cancer patient is depicted by identical symbols connected by a dashed line. There is a general decrease in the proportion of DNA ≤150 bp for the plasma DNA in cancer patients after tumor resection.

The separation in the values of the proportion for pre-treatment and post-treatment illustrate a correlation between the existence of a tumor and the value of the size parameter. The separation in the values for pre-treatment and post-treatment can be used to determine how successful the treatment was, e.g., by comparing the proportion to a threshold, where a proportion below the threshold can indicate success. In another example, a difference between the pre-treatment and post-treatment can be compared to a threshold.

The proportion (or any other value of a size parameter) can also be used to detect an occurrence of a tumor. For example, a baseline value for a size parameter can be determined. Then, at a later time, a value for the size parameter can be measured again. If the value of the size parameter shows a significant change, then the patient may be at a higher risk of having a tumor. If the value of the size parameter does not vary much among individuals, which FIG. 18A indicates that the proportion does not (i.e., since post-treatment values are the same), then the same baseline value can be used for other patients. Thus, a baseline value does not need to be taken for each patient.

Figure 18B:
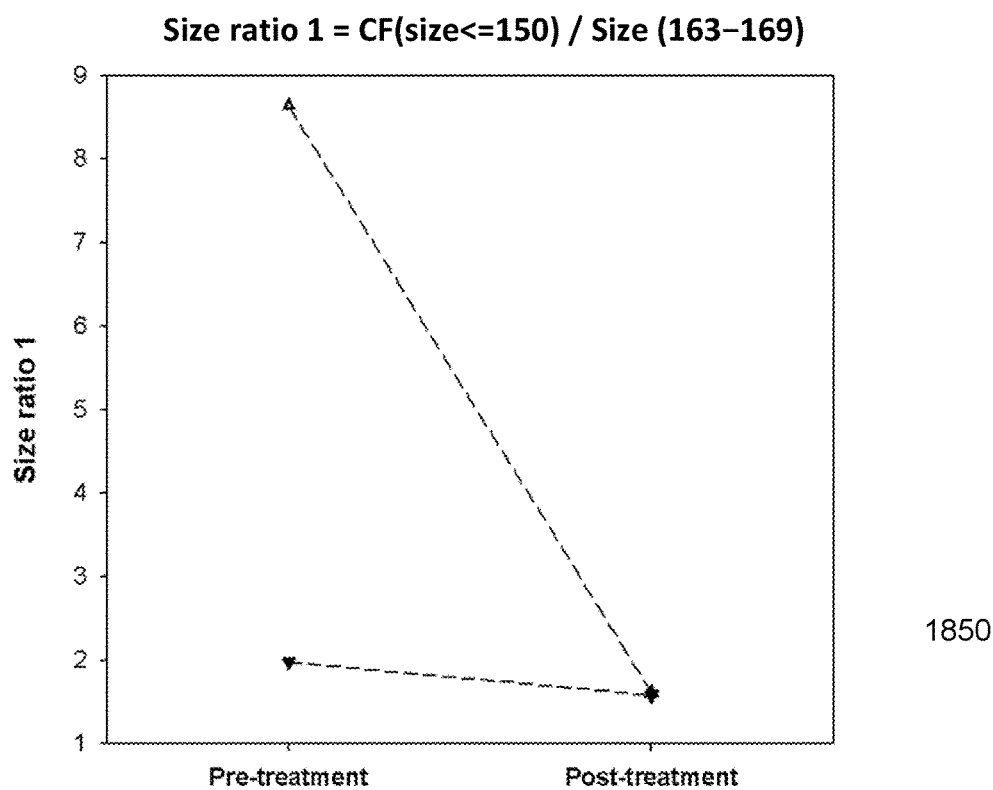
FIG. 18B is a plot 1850 showing a size ratio of the amounts of DNA fragments of ≤150 bp and DNA from 163 bp to 169 bp, which is labeled as (CF(size≤150)/size(163-169)), for HCC patients before and after tumor resection.

FIG. 18B is a plot 1850 showing a size ratio of the amounts of DNA fragments of ≤150 bp and DNA from 163 bp to 169 bp, which is labeled as (CF(size≤150)/size(163-169)), for HCC patients before and after tumor resection. The pair of samples from the same cancer patient is depicted by identical symbols connected by a dashed line. There is a decrease in this size ratio for the two cases after tumor resection.

Figure 19A:
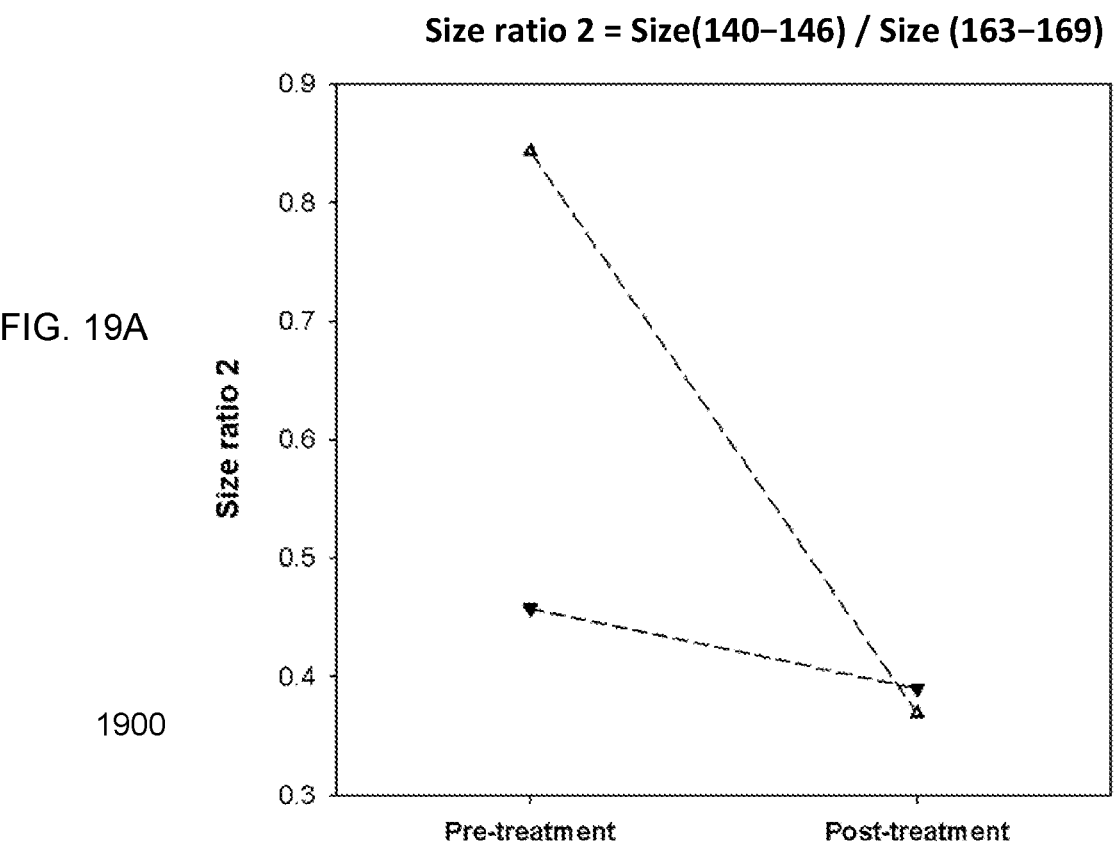
FIG. 19A is a plot 1900 showing a size ratio of the amounts of DNA fragments from 140 bp to 146 bp and DNA from 163 bp to 169 bp, which is labeled as (size(140-146)/size(163-169)), for HCC patients before and after tumor resection.

FIG. 19A is a plot 1900 showing a size ratio of the amounts of DNA fragments from 140 bp to 146 bp and DNA from 163 bp to 169 bp, which is labeled as (size(140-146)/size(163-169)), for HCC patients before and after tumor resection. The pair of samples from the same cancer patient is depicted by identical symbols connected by a dashed line. There is decrease in this size ratio for the two cases after tumor resection.

Figure 19B:
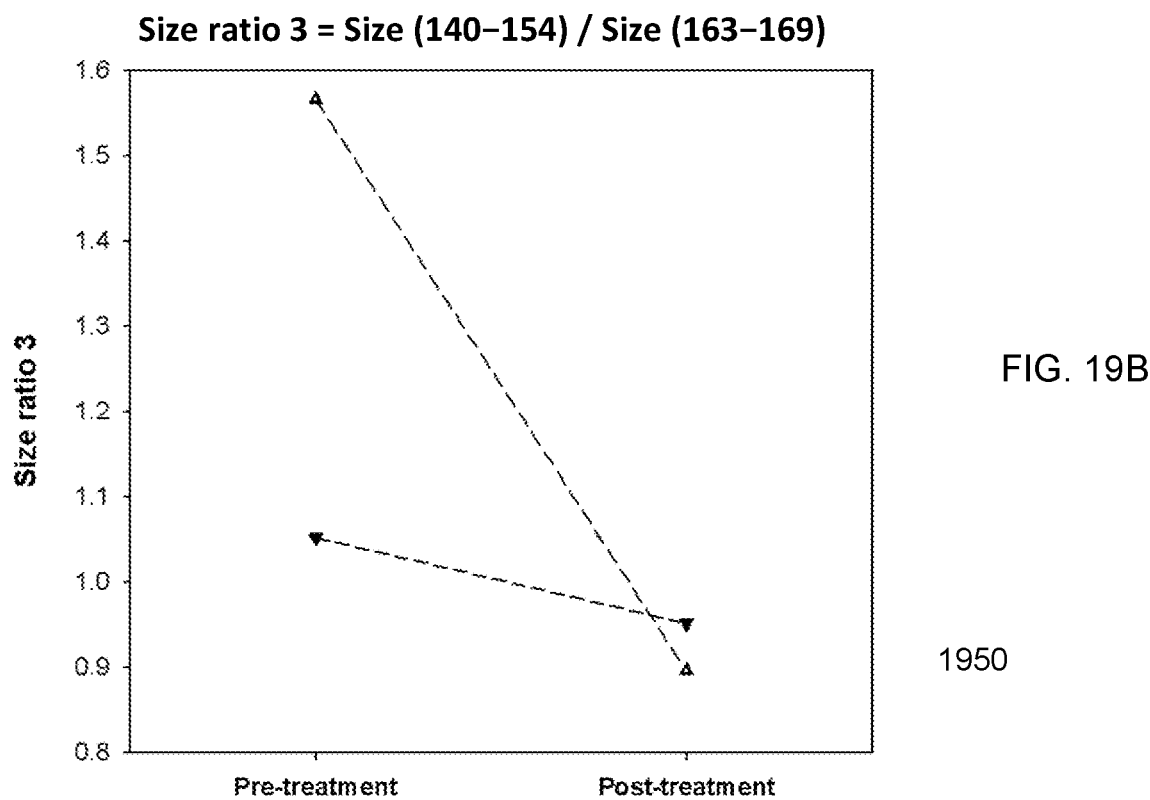
FIG. 19B is a plot 1950 showing a size ratio of the amounts of DNA fragments from 140 bp to 154 bp and DNA from 163 bp to 169 bp, which is labeled as (size(140-154)/size(163-169)), for HCC patients before and after tumor resection.

FIG. 19B is a plot 1950 showing a size ratio of the amounts of DNA fragments from 140 bp to 154 bp and DNA from 163 bp to 169 bp, which is labeled as (size(140-154)/size(163-169)), for HCC patients before and after tumor resection. The pair of samples from the same cancer patient is depicted by identical symbols connected by a dashed line. There is a decrease in this size ratio for the two cases after tumor resection.

Figure 20:
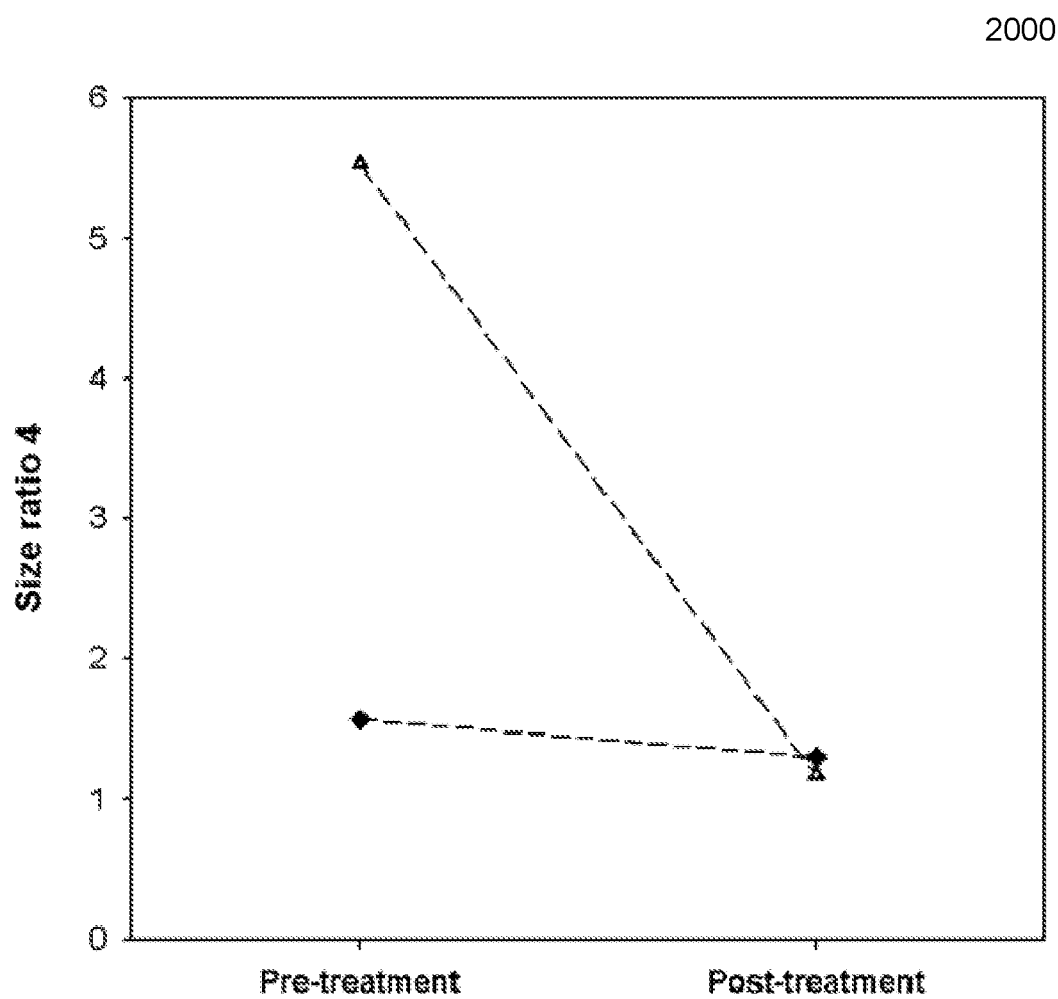
FIG. 20 is a plot 2000 showing a size ratio of the amounts of DNA fragments from 100 bp to 150 bp and DNA from 163 bp to 169 bp, which is labeled as (size(100-150)/size (163-169)), for HCC patients before and after tumor resection.

FIG. 20 is a plot 2000 showing a size ratio of the amounts of DNA fragments from 100 bp to 150 bp and DNA from 163 bp to 169 bp, which is labeled as (size(100-150)/size(163-169)), for HCC patients before and after tumor resection. The pair of samples from the same cancer patient is depicted by identical symbols connected by a dashed line. There is a decrease in this size ratio for the two cases after tumor resection.

C. Method

FIG. 21 is a flowchart illustrating a method 2100 for analyzing a biological sample of an organism to determine a classification of a level of cancer according to embodiments of the present invention. Method 2100 can analyze the biological sample of the organism (e.g., a human). The biological sample includes DNA originating from normal cells and potentially from cells associated with cancer. At least some of the DNA is cell-free in the biological sample. Aspects of methods 300 and 1300 can be used with embodiments of method 2100.

At block 2110, amounts of DNA fragments corresponding to various sizes are measured. For each size of a plurality of sizes, an amount of a plurality of DNA fragments from the biological sample corresponding to the size can be measured, as described for method 300. The plurality of DNA fragments may be chosen at random or preferentially selected from one or more predetermined regions of a genome. For example, targeted enrichment may be performed or selection of sequence reads that are from particular regions of the genome may be used, e.g., as described above.

At block 2120, a first value of a first parameter is calculated based on the amounts of DNA fragments at multiple sizes. In one aspect, the first parameter provides a statistical measure of a size profile (e.g., a histogram) of DNA fragments in the biological sample. The parameter may be referred to as a size parameter since it is determined from the sizes of the plurality of DNA fragments. Examples of parameter are provided herein. Multiple parameters may be used, as is also described herein.

At block 2130, the first value is compared to a reference value. Examples of a reference value include a normal value and a cutoff value that is a specified distance from a normal value (e.g., in units of standard deviation). The reference value may be determined from a different sample from the same organism (e.g., when the organism was known to be healthy). Thus, the reference value may correspond to a value of the first parameter determined from a sample when the organism is presumed to have no cancer. In one embodiment, the biological sample is obtained from the organism after treatment and the reference value corresponds to a value of the first parameter determined from a sample taken before treatment (e.g., illustrated above). The reference value may also be determined from samples of other healthy organisms.

At block 2140, a classification of a level of cancer in the organism is determined based on the comparison. In various embodiments, the classification may be numerical, textual, or any other indicator. The classification can provide a binary result of yes or no as to cancer, a probability or other score, which may be absolute or a relative value, e.g., relative to a previous classification of the organism at an earlier time. In one implementation, the classification is that the organism does not have cancer or that the level of cancer has decreased. In another implementation, the classification is that the organism does have cancer or that a level of cancer has increased.

As described herein, the level of cancer can include an existence of cancer, a stage of the cancer, or a size of a tumor. For example, whether the first value exceeds (e.g., greater than or less than, depending on how the first parameter is define) can be used to determine if cancer exists, or at least a likelihood (e.g., a percentage likelihood). The extent above the threshold can provide an increasing likelihood, which can lead to the use of multiple thresholds. Additionally, the extent above can correspond to a different level of cancer, e.g., more tumors or larger tumors. Thus, embodiments can diagnose, stage, prognosticate, or monitor progress of a level of cancer in the organism.

D. Determining Size Distribution for Particular Regions

As with other embodiments, the first set of DNA fragments can correspond to one or more predetermined regions of a genome of the organism. Thus, the size analysis can also be performed for select regions, e.g., specific chromosomes, arms of chromosomes, or multiple regions (bins) of the same length, e.g., 1 Mb. For example, one can focus on regions that are commonly altered in a cancer type of interest. Table 2200 of FIG. 22 shows some common chromosomal aberrations seen in various types of cancers. The gain refers to an amplification of a chromosome with one or more additional copies within a particular segment and loss refers to deletions of one or both homologous chromosome within a particular segment.

In one embodiment, additional sets of DNA fragments can be identified from the biological sample. Each set of DNA fragments can correspond to different predetermined regions, such as the regions specified in table 2200. Regions that are not associated with cancer could also be used, e.g., to determine a reference value. The amount of DNA fragments corresponding to various sizes can be determined and size value of a parameter can be determined for each additional set of DNA fragments, as described herein. Thus, a different size value can be determined for each genomic region, where there is a one-one correspondence between a set of DNA fragments and a genomic region.

Each of the size values can be compared to a respective reference value. Predetermined regions where the corresponding size value is statistically different than the respective reference value can be identified. When a reference value is a normal value, the determination of statistical difference can be made by comparing a size value to a cutoff (e.g., where the cutoff value is a specific number of standard deviations from the normal value, based on an assumed or measured statistical distribution). The respective reference values may be the same or different for different regions. For example, different regions may have different normal values for size.

In one embodiment, the number of regions statistically different than the reference value may be used to determine the classification. Thus, one can determine the number of identifying predetermined regions where the corresponding size value is statistically different than the respective reference value. The number can be compared to a threshold number of regions to determine the classification of the level of cancer in the organism. The threshold number can be determined based on a variance within normal samples and within cancer samples.

As highlighted in table 2200, different cancers are associated with different parts of the genome. Thus, which regions that statistically different can be used to determine one or more possible types of cancer when the possible types of cancer are associated with the identified regions. For example, if a size value for DNA fragments from chromosomal segment 7p is found to be significantly lower than a normal value (e.g., as determined by a cutoff value), then colorectal cancer can be identified as a likely cancer when the classification indicates that cancer exists. Note that the size value for chromosomal segment 7p may be used as a sole indicator to determine the classification, or multiple regions may be used. In one embodiment, only if an overall classification indicates cancer would the size value for chromosomal segment 7p be used to identify colorectal cancer as a likely cancer.

IX. Computer System

Figure 23:
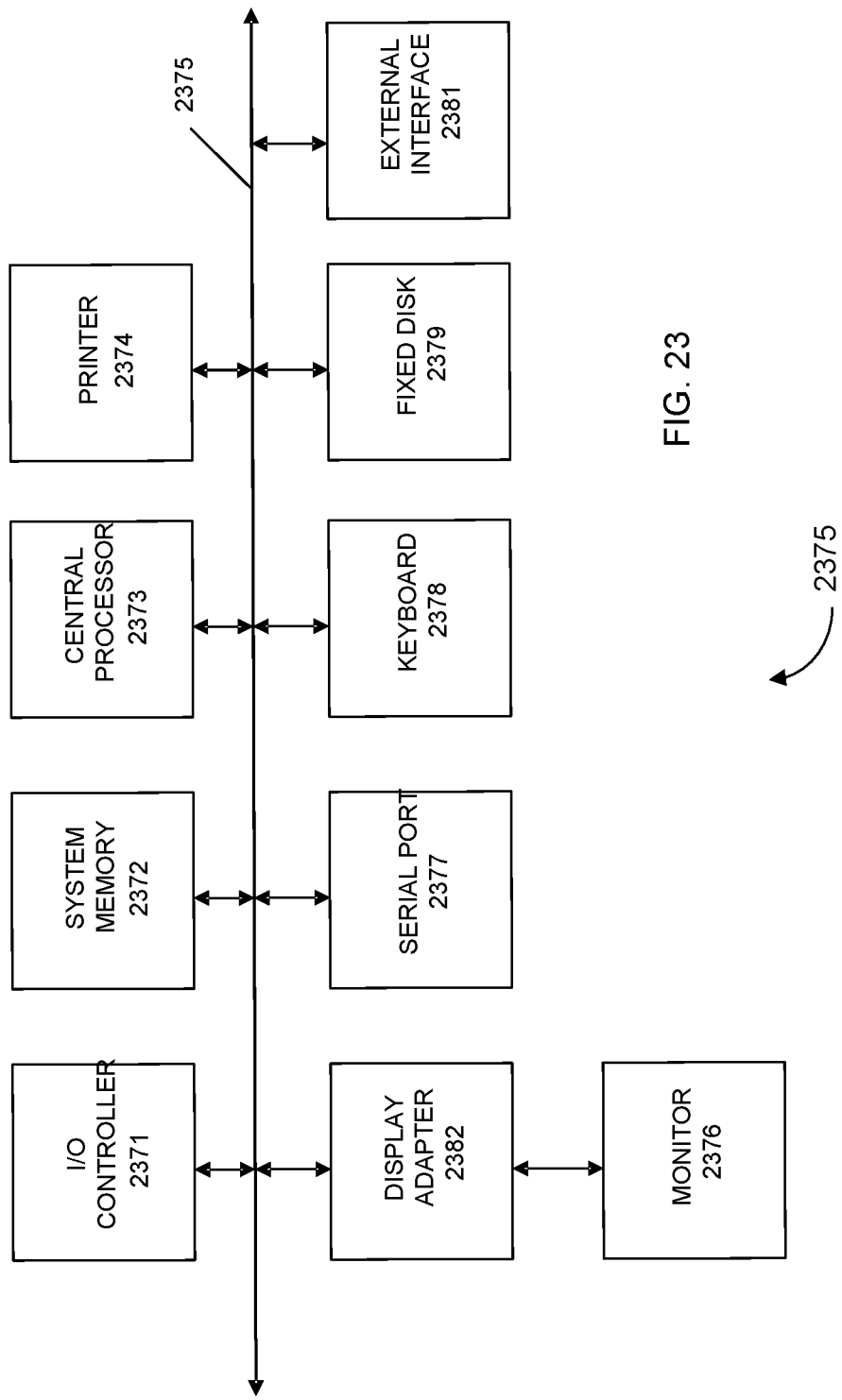
FIG. 23 shows a block diagram of an example computer system 2300 usable with system and methods according to embodiments of the present invention.

Any of the computer systems mentioned herein may utilize any suitable number of subsystems. Examples of such subsystems are shown in FIG. 23 in computer apparatus 2300. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 23 are interconnected via a system bus 2375. Additional subsystems such as a printer 2374, keyboard 2378, fixed disk 2379, monitor 2376, which is coupled to display adapter 2382, and others are shown. Peripherals and input/output (I/O) devices, which couple to I/O controller 2371, can be connected to the computer system by any number of means known in the art, such as serial port 2377. For example, serial port 2377 or external interface 2381 (e.g. Ethernet, Wi-Fi, etc.) can be used to connect computer system 2300 to a wide area network such as the Internet, a mouse input device, or a scanner. The interconnection via system bus 2375 allows the central processor 2373 to communicate with each subsystem and to control the execution of instructions from system memory 2372 or the fixed disk 2379, as well as the exchange of information between subsystems. The system memory 2372 and/or the fixed disk 2379 may embody a computer readable medium. Any of the values mentioned herein can be output from one component to another component and can be output to the user.

A computer system can include a plurality of the same components or subsystems, e.g., connected together by external interface 2381 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned above are herein incorporated by reference in their entirety for all purposes. None is admitted to be prior art.

What is claimed is:

1. A method of analyzing a biological sample of an organism, the biological sample including DNA fragments originating from normal cells and potentially from cells associated with cancer, wherein at least some of the DNA fragments are cell-free in the biological sample, the method comprising:
for each of a plurality of DNA fragments from the biological sample:
receiving one or more sequence reads obtained from a sequencing of the DNA fragment, the one or more sequence reads including both ends of the DNA fragment;
aligning the one or more sequence reads to a reference genome to obtain aligned locations for both ends of the DNA fragment; and
using the aligned locations to determine a size of the DNA fragment;
for each size of a plurality of sizes, determining an amount of a first set of the plurality of DNA fragments from the biological sample corresponding to the size using the sizes determined from the aligned locations for the first set;
calculating a first value of a first parameter based on the amounts of DNA fragments at multiple sizes, the first parameter providing a statistical measure of a size profile of DNA fragments in the biological sample;
comparing the first value to a reference value; and
determining a classification of a level of cancer in the organism based on the comparison.

2. The method of claim 1, wherein the first set of DNA fragments corresponds to one or more predetermined regions of a genome of the organism.

3. The method of claim 2, further comprising:
identifying additional sets of DNA fragments from the biological sample, wherein each set of DNA fragments corresponds to different predetermined regions;
measuring amounts of DNA fragments corresponding to the plurality of sizes;
calculating size values of the first parameter for the additional sets of DNA fragments;
comparing each of the size values to a respective reference value; and
identifying predetermined regions where the corresponding size value is statistically different than the respective reference value.

4. The method of claim 3, further comprising:
using the identified predetermined regions to determine one or more possible types of cancer, wherein the possible types of cancer are associated with the identified predetermined regions.

5. The method of claim 3, wherein determining the classification of the level of cancer in the organism based on the comparison includes:
determining a number of the predetermined regions identified where the corresponding size value is statistically different than the respective reference value; and
comparing the number to a threshold number of regions to determine the classification of the level of cancer in the organism.

6. The method of claim 3, wherein at least two of the respective reference values are different.

7. The method of claim 1, wherein the determined classification corresponds to a size of a tumor or to a number of tumors.

8. The method of claim 1, wherein the biological sample is obtained from the organism after treatment, and wherein the reference value corresponds to a value of the first parameter determined from a sample taken before treatment.

9. The method of claim 1, wherein the reference value corresponds to a value of the first parameter determined from a sample when the organism is presumed to have no cancer.

10. The method of claim 1, wherein the reference value is established from one or more biological samples obtained from one or more healthy organisms.

11. The method of claim 1, wherein the classification is that the organism does not have cancer or that the level of cancer has decreased.

12. The method of claim 1, wherein the classification is that the organism does have cancer or that the level of cancer has increased.

13. The method of claim 1, wherein the organism is a human.

14. The method of claim 1, wherein the first set of the plurality of DNA fragments is chosen randomly.

15. The method of claim 1, wherein the plurality of DNA fragments comprises greater than 100,000 DNA fragments.

16. The method of claim 1, wherein:
the classification of the level of cancer is that the cancer exists and
the organism is treated by having tumor resection performed after the classification is determined.

17. The method of claim 1, wherein the reference genome is a human reference genome.

18. A computer product comprising a non-transitory computer readable medium storing a plurality of instructions that when executed control a computer system to analyze a biological sample of an organism, the biological sample including DNA originating from normal cells and potentially from cells associated with cancer, wherein at least some of the DNA is cell-free in the biological sample, the instructions comprising:
for each of a plurality of DNA fragments from the biological sample:
receiving one or more sequence reads obtained from a sequencing of the DNA fragment, the one or more sequence reads including both ends of the DNA fragment;
aligning the one or more sequence reads to a reference genome to obtain aligned locations for both ends of the DNA fragment; and
using the aligned locations to determine a size of the DNA fragment;
for each size of a plurality of sizes, determining an amount of a first set of the plurality of DNA fragments from the biological sample corresponding to the size using the sizes determined from the aligned locations for the first set;
calculating a first value of a first parameter based on the amounts of DNA fragments at multiple sizes, the first parameter providing a statistical measure of a size profile of DNA fragments in the biological sample;
comparing the first value to a reference value; and
determining a classification of a level of cancer in the organism based on the comparison.

19. The computer product of claim 18, wherein the first set of DNA fragments corresponds to one or more predetermined regions of a genome of the organism and wherein the instructions further comprise:
identifying additional sets of DNA fragments from the biological sample, wherein each set of DNA fragments corresponds to different predetermined regions;
measuring amounts of DNA fragments corresponding to the plurality of sizes;
calculating size values of the first parameter for the additional sets of DNA fragments;
comparing each of the size values to a respective reference value; and
identifying predetermined regions where the corresponding size value is statistically different than the respective reference value.

20. The computer product of claim 19, the instructions further comprising:
using the identified predetermined regions to determine one or more possible types of cancer, wherein the possible types of cancer are associated with the identified predetermined regions.

21. The computer product of claim 19, wherein determining the classification of the level of cancer in the organism based on the comparison includes:
determining the number of identifying predetermined regions where the corresponding size value is statistically different than the respective reference value; and
comparing the number to a threshold number of regions to determine the classification of the level of cancer in the organism.

22. A computer system comprising:
the computer product of claim 18 and one or more processors.

* * * * *